United States Patent
Carpino et al.

(10) Patent No.: US 7,145,012 B2
(45) Date of Patent: Dec. 5, 2006

(54) CANNABINOID RECEPTOR LIGANDS AND USES THEREOF

(75) Inventors: Philip A. Carpino, Groton, CT (US); Robert L. Dow, Groton, CT (US)

(73) Assignee: Pfizer Inc., New York, NY (US)

( * ) Notice: Subject to any disclaimer, the term of this patent is extended or adjusted under 35 U.S.C. 154(b) by 41 days.

(21) Appl. No.: 10/823,107

(22) Filed: Apr. 12, 2004

(65) Prior Publication Data

US 2004/0214855 A1 Oct. 28, 2004

Related U.S. Application Data

(60) Provisional application No. 60/464,831, filed on Apr. 23, 2003.

(51) Int. Cl.
*C07D 471/02* (2006.01)
(52) U.S. Cl. ........................ 546/119; 514/303
(58) Field of Classification Search ................ 514/303; 546/119
See application file for complete search history.

(56) References Cited

U.S. PATENT DOCUMENTS

| | | | |
|---|---|---|---|
| 3,340,269 A | 9/1967 | Blatter | 260/294.7 |
| 3,365,459 A | 1/1968 | Blatter | 260/296 |
| 3,423,414 A | 1/1969 | Blatter | 260/296 |
| 3,526,633 A | 9/1970 | Gadekar et al. | 260/295 |
| 4,490,541 A | 12/1984 | Ellingsfeld et al. | 548/370 |
| 4,925,846 A | 5/1990 | Deacon et al. | |
| 4,944,790 A | 7/1990 | Moser et al. | |
| 5,134,142 A | 7/1992 | Matsuo et al. | |
| 5,462,960 A | 10/1995 | Barth et al. | |
| 5,596,106 A | 1/1997 | Cullinan et al. | |
| 5,624,941 A | 4/1997 | Barth et al. | |
| 5,744,491 A | 4/1998 | Boigegrain et al. | |
| 5,744,493 A | 4/1998 | Boigegrain et al. | |
| 5,747,524 A | 5/1998 | Cullinan et al. | |
| 5,925,768 A | 7/1999 | Barth et al. | |
| 6,028,084 A | 2/2000 | Barth et al. | |
| 6,100,259 A | 8/2000 | Xiang et al. | |
| 6,344,474 B1 | 2/2002 | Maruani et al. | |
| 6,355,631 B1 | 3/2002 | Achard et al. | |
| 6,432,984 B1 | 8/2002 | Barth et al. | |
| 6,476,060 B1 | 11/2002 | Lange et al. | |
| 6,479,479 B1 | 11/2002 | Achard et al. | |
| 6,509,367 B1 | 1/2003 | Martin et al. | |
| 6,518,264 B1 | 2/2003 | Achard et al. | |
| 6,566,356 B1 | 5/2003 | Achard et al. | |
| 2001/0027193 A1 | 10/2001 | Achard et al. | |
| 2001/0053788 A1 | 12/2001 | Lange et al. | |
| 2002/0019383 A1 | 2/2002 | Achard et al. | |
| 2002/0019421 A1 | 2/2002 | Biberman et al. | |
| 2002/0035102 A1 | 3/2002 | Achard et al. | |
| 2002/0091114 A1 | 7/2002 | Plot-Grosjean et al. | |
| 2002/0119972 A1 | 8/2002 | Leftheris et al. | |
| 2002/0128302 A1 | 9/2002 | Maruani et al. | |
| 2002/0188007 A1 | 12/2002 | Barth et al. | |
| 2003/0003145 A1 | 1/2003 | Abramovici et al. | |
| 2003/0055033 A1 | 3/2003 | Achard et al. | |
| 2003/0114495 A1 | 6/2003 | Finke et al. | |
| 2003/0139386 A1 | 7/2003 | Cote et al. | |
| 2003/0199536 A1 | 10/2003 | Thomas et al. | |
| 2004/0072833 A1 | 4/2004 | Nakai et al. | |
| 2004/0077650 A1 | 4/2004 | Dow | |
| 2004/0092520 A1 | 5/2004 | Griffith | |
| 2004/0122074 A1 | 6/2004 | Dow et al. | 514/397 |
| 2004/0157838 A1 | 8/2004 | Griffith | 514/227.8 |
| 2004/0157839 A1 | 8/2004 | Griffith | 514/227.8 |
| 2004/0214837 A1 | 10/2004 | Griffith et al. | 514/262.1 |
| 2004/0214838 A1 | 10/2004 | Carpino et al. | 514/262.1 |
| 2004/0214856 A1 | 10/2004 | Carpino et al. | 514/303 |
| 2004/0224970 A1 | 11/2004 | Smith et al. | |

FOREIGN PATENT DOCUMENTS

| | | |
|---|---|---|
| DE | 4208535 | 3/1992 |
| EP | 293220 B1 | 8/1994 |
| EP | 1162196 | 12/2000 |

(Continued)

OTHER PUBLICATIONS

Barth, F et al 'The developent of cannabinid antagonists' PubMed ID 10469889 (1999).*

(Continued)

*Primary Examiner*—Amelia A. Owens
(74) *Attorney, Agent, or Firm*—Gregg C. Benson; Arlene K. Musser

(57) ABSTRACT

Compounds of Formula (I) and (II) that act as cannabinoid receptor ligands and their uses in the treatment of diseases linked to the mediation of the cannabinoid receptors in animals are described herein

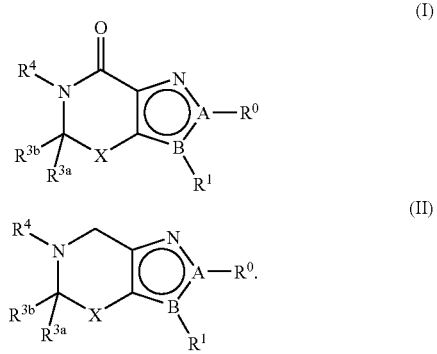

17 Claims, No Drawings

FOREIGN PATENT DOCUMENTS

| | | |
|---|---|---|
| EP | 1354884 | 10/2003 |
| WO | WO 9501980 | 6/1994 |
| WO | WO 96/02248 A1 | 2/1996 |
| WO | WO 9946267 | 9/1999 |
| WO | WO 0063208 | 4/2000 |
| WO | WO 00/15609 A1 | 5/2000 |
| WO | WO 01/24798 A1 | 4/2001 |
| WO | WO 01/028557 A1 | 4/2001 |
| WO | WO 01/029007 A1 | 4/2001 |
| WO | WO 01/032629 A1 | 5/2001 |
| WO | WO 01/032663 A2 | 5/2001 |
| WO | WO 01/58450 A2 | 8/2001 |
| WO | WO 0158869 | 8/2001 |
| WO | WO 01/85092 A2 | 11/2001 |
| WO | WO 02053565 | 7/2002 |
| WO | WO 03007945 | 7/2002 |
| WO | WO 03027114 | 9/2002 |
| WO | WO 02/076949 A1 | 10/2002 |
| WO | WO 03/006007 A1 | 1/2003 |
| WO | WO 03/007887 A2 | 1/2003 |
| WO | WO 03/018060 A1 | 3/2003 |
| WO | WO 03/020217 A2 | 3/2003 |
| WO | WO 03/020314 A1 | 3/2003 |
| WO | WO 03/026647 A1 | 4/2003 |
| WO | WO 03/026648 A1 | 4/2003 |
| WO | WO 03/027069 A1 | 4/2003 |
| WO | WO 03/027076 A2 | 4/2003 |
| WO | WO 03/027114 A1 | 4/2003 |
| WO | WO 03/040107 A1 | 5/2003 |
| WO | WO 03/051850 A1 | 6/2003 |
| WO | WO 03/051851 A1 | 6/2003 |
| WO | WO 03/075660 A1 | 9/2003 |
| WO | WO 03/077847 A2 | 9/2003 |
| WO | WO 03/078413 A1 | 9/2003 |
| WO | WO 03/082190 A2 | 10/2003 |
| WO | WO 03/082191 A2 | 10/2003 |
| WO | WO 03/082256 A2 | 10/2003 |
| WO | WO 03/082833 A1 | 10/2003 |
| WO | WO 03/084943 A2 | 10/2003 |
| WO | WO 03/086288 A2 | 10/2003 |
| WO | WO 03/087037 A1 | 10/2003 |
| WO | WO 03095455 | 11/2003 |
| WO | WO 04/012617 A2 | 2/2004 |

OTHER PUBLICATIONS

Duplantier, AJ et al '7-oxo-4,5,7-tetrahydro-1H-pyrazolo[3,4-c]pyridines as Novel Inhibitors of Human Eosinophil Phosphodiesterase' CA 129:49198 (1998).*

Ciba Ltd. '1H- and 2H-Pyraxolo[3,4-c]pyridine derivatives' CA 65:12344 (1965).*

Duplantier, AJ 'Preparation of tetrahydropyrazolo[3,4-c]pyridines as inhibitors of phosphodiesteras IV or the production of tumor necrosis factor' CA 122:239696 (1995).*

Black, SC, Cannabinoid receptor antagonists and obesity, PMID:15134279 (2004).*

Grigg, R., et al., *Tetrahedron Letters*, "A Catalytic Hydrogenation Route to Azomethine Imines", vol. 31, vol. 31, pp. 2767-2770 (1990).

Kanyonyo, M., et al., *Bioorganic & Medicinal Chemistry Letters*, vol. 9, pp. 2233-2236 (1999).

Pertwee, R., *Exp. Opin. Invest. Drugs*, "Cannabinoid Receptor Ligands: Clinical and Neuropharmacological Considerations, Relevant to Future Drug Discovery and Development", vol. 9(7), pp. 1553-1571 (2000).

Tzavara, E.T., et al., "The CB1 Receptor Antagonist SR141716A selectively increases monoaminergic neurotransmission in the medial prefrontal cortex: Implications for Therapeutic Actions," *J Pharmacol*, 138, 544-553 (2003).

Racz, I., et al., "A Critical Role for the Cannabinoid CB1 Receptors in Alcohol Dependence and Stress-Stimulated Ethanol Drinking," *J Neurosci*, 23(6), 2453-2458 (2003).

Croci, T., et al., "Role of Cannabinoid CB1 Receptors and Tumor Necrosis Factor-$\alpha$ in the gut and systemic anti-inflammatory activity of SR 141716 (Rimonabant) in rodents," *Brit J Pharmacol*, 140, 115-122 (2003).

DaSilva, G.E., et al., "Potentiation of Penile Erection and Yawning Responses to Apomorphine by Cannabinoid Receptor Antagonists in Rats," *Neurosci Let*, 349, 49-52 (2003).

Wang, L., et al., "Endocannabinoid Signaling via Cannabinoid Receptor 1 is Involved in Ethanol Preference and its Age-Dependent Decline in Mice," *PNAS*, 100(3), 1393-1398 (2003).

Ruiu, S., et al., "Synthesis and Characterization of NESS 0327: A Novel Putative Antagonist of the CB1 Cannabinoid Receptor," *J Pharmacol Exp Therap*, 306, 363-370 (2003).

Howlett, A.C., et al., "International Union of Pharmacology. XXVII. Classification of Cannabinoid Receptors," *Pharmacol Rev*, 54, 161-202 (2002).

Gomez, R., et al., "A Peripheral Mechanism for CB1 Cannabinoid Receptor-Dependent Modulation of Feeding," *J. Neurosci*, 22(21), 9612-9617 (2002).

Wiley, J.L., et al., "Novel Pyrazole Cannabinoids: Insights into CB1 Receptor Recognition and Activation," *J Pharmacol Exp Therap*, 296(3), 1013-1022 (2001).

Lellemand, F., et al., "Effects of CB1 Cannabinoid Receptor Blockade on Ethanol Preference After Chronic Ethanol Administration," *Alcohol Clin Exp Res*, 25(9), 1317-1323 (2001).

Pertwee, R.G., "Cannabinoids and the Gastronintestinal Tract," *Gut*, 48, 859-867 (2001).

Pertwee, R.G., "Cannabinoid Receptor Ligands: Clinical and Neuropharmacological Considerations, Relevant to Future Drug Discovery and Development," *Exp. Opin. Invest. Drugs*, 9(7), 1573-1571 (2000).

Hungund, B.L and B.S. Basavarajappa, "Are Anadamide and Cannabinoid Receptors involved in Ethanol Tolerance? A Review of the Evidence," *Alcohol & Alcoholism*. 35(2) 126-133, (2000).

Freedland, C.S., et al., "Effects of SR141716A, a Central Cannabinoid Receptor Antagonist, on Food-maintained Responding," *Pharmacol Biochem Behav*, 67, 265-270 (2000).

Lan, R., et al., "Structure-Activity Relationships of Pyrazole Derivatives as Cannabinoid Receptor Antagonists" *J. Med. Che.m*, 42, 769-776 (1999).

Pertwee, R.G., "Pharmacology of Cannabinoid Receptor Ligands" *Curr Med Chem*, 6, 635-664 (1999).

Basavarajappa, B.S., et al., "Chronic Ethanol Administration Down-regulates Cannabinoid Receptors in Mouse Brain Synaptic Plasma Membrane," *Brain Res*, 793, 212-218 (1998).

Thomas, B.F., et al., "Comparative Receptor Binding Analyses of Cannabinoid Agonists and Antagonists," *J Pharmacol Exp Therap*, 285, 285-292 (1998).

Colombo, G., et al., "Appetite Suppression and Weight Loss after the Cannabinoid Antagonist SR141716," *Life Sci.*, 63, PL113-PL117 (1998).

Simiand, J., et al., "SR141716, a CB1 Cannabinoid Receptor Antagonist, Selectively Reduces Sweet Food Intake in Marmose," *Behav. Pharmacol.*, 9, 179-181 (1998).

Chaperon, F., et al., "Involvement of Central Cannabinoid (CB1) Receptors in the Establishment of Place Conditioning in Rats," *Psychopharmacology*, 135, 324-332 (1998).

Arnone, M., et al., "Selective Inhibition of Sucrose and Ethanol Intake by SR141716, an Antagonist of Central Cannabinoid (CB1) Receptors," *Psychopharmacol*, 132, 104-106 (1997).

Savontaus, E., et al., "Anti-Obesity Effect of MPV-1743 A III, a Novel Imidazoline Derivative, in Genetic Obesity," *Eur J Pharmacol*, 328, 207-215 (1997).

Sanudo-Pena, M.C., et al., "Endogenous Cannabinoids as an Aversive or Counter-rewarding System in the Rat," *Neurosci Let*, 223, 125-128 (1997).

Gifford, A.N., et al., "Electrically Evoked Acetylcholine Release from Hippocampal Silices is Inhibited by the Cannabinoid Receptor Agonist, WIN 55212-2 and is Potentiated by the Cannabinoid Antagonist, SR 141716A," *J Pharmacol Exp Ther*, 277, 1431-1436 (1996).

Compton, D.R., et al., "In Vivo Characterization of a Specific Cannabinoid Receptor Antagonist (SR141716A); Inhibition of Delta-9-Tetrahydrocannabinol-Induced Responses and Apparent Agonist Activity," *J Pharmacol Exp Ther*, 277, 586-594 (1996).

Mansbach, R.S., et al., "Effects of the Cannabinoid CB1 Receptor Antagonist SR141716A on the Behavior of Pigeons and Rats," *Psychopharmacology*, 124, 315-322 (1996).

Lichtman, A.H., et al., "Delta-9-Tetrahydrocannabinol Impairs Spatial Memory through a Cannabinoid Receptor Mechanism," *Psychopharmacology*, 126, 125-131 (1996).

Perio, A., et al., "Central Mediation of the Cannabinoid Cue: Activity of a Selective CB1 Antagonist, SR141716A," *Behavioral Parmacology*, 7, 65-71 (1996).

Rinaldi-Carmona, M., et al., "Biochemical and Pharmacological Characteriszation of SR141716A, The First Potent and Selective Brain Cannabinoid Receptor Antagonist," *Life Sci*, 56, 1941-1947 (1995).

Pertwee, R., et al., "AM630, A Competititve Cannabinoid Receptor Antagonist," *Life Sci*, 56, 1949-1955 (1995).

Rinaldi-Carmona, M., et al., "SR141716A, a Patent and Selective Antagonist of the Brain Cannabinoid Receptor," *FEBS Letters*, 350, 240-244 (1994).

Dutta, A., et al., "The Synthesis and Pharmacological Evaluation of the Cannabinoid Antagonist SR 141716A", *Med. Chem. Rev.* 5, 54-62 (1994).

Drummond, J., et al., "Evaluation and Synthesis of Aminohydroxyisoxazoles and Pyrazoles as Potential Glycine Agonists," *J. Med. Chem*, 32, 2116-2128 (1989).

Murray, W., et al., "A Simple Regioselective Synthesis of Ethyl 1,5-Diarylpyrazole-3-carboxylates" *J. Heterocyclic Chem*, 26, 1389 (1989).

Dewey, W.L. "Cannabinoid Pharmacology," *Pharmacological Reviews*, 38(2)m 151-178 (1986).

Tewari, R.S., et al., "1,3-Dipolar Cycloaddition and Nucleophylic Substitution Reactions of C-Acetyl and C-Ethoxycarbonyl Derivative of Hydrazidoyl Bromides" *Tetrahedron*, 39(1) 129-136 (1983).

Birkofer, L. and K. Richtzenhain, "Silyl-Derivate von Pyrazol, Isoxazol und 1,2,3-Triazol" *Chem. Ber.* 112, 2829-2836 (1979).

Franke, H. et al., "Polare Cycloadditionen von elektronenreichen Mehrfach-bindungssystemen an 1,3,4-oxadiazolium-Salze: Synthese von 3aH-[1,3,4]Oxadiazolo[3,2-a]chinolinen" *Chem. Ber.* 112, 3623-3636 (1979).

Sucrow, W., et al., "Bimolekulare Cyclisierung von 2-(1-Methylhydrazino)maleinsaure-dimethylester" *Chem. Ber.* 112, 1712-1718 (1979).

Barth, F., et al., *Current Medicinal Chemistry*, "The Development of Cannabinoid Antagonists", vol. 6, pp. 748-755 (1999).

Duplantier, A., et al., *J. Med. Chem*, "7-Oxo-4,5,6,7-tetrahydro-1H-pyrazolo[3,4,-c]pyridines as Novel Inhibitors of Human Eosinophil Phosphodiesterase", vol. 41, pp. 2268-2277 (1998).

Muccioli, et al., *Current Medicinal Chemistry*, "Current Knowledge on the Antagonists and Inverse Agonists of Cannabinoid Receptors", vol. 12, pp. 1361-1394 (2005).

Smith, et al., *IDRUGS*, "Recent Advances in the Research and Development of CB1 Antagonists", vol. 8(1) pp. 53-66 (2005).

* cited by examiner

CANNABINOID RECEPTOR LIGANDS AND USES THEREOF

This application claims the benefit of U.S. Provisional Application No. 60/464,831 filed on Apr. 23, 2003 and incorporated herein by reference in its entirety.

FIELD OF THE INVENTION

The present invention relates to bicyclic pyrazolyl and imidazolyl compounds as cannabinoid receptor ligands, in particular CB1 receptor antagonists, and uses thereof for treating diseases, conditions and/or disorders modulated by cannabinoid receptor antagonists.

BACKGROUND

Obesity is a major public health concern because of its increasing prevalence and associated health risks. Obesity and overweight are generally defined by body mass index (BMI), which is correlated with total body fat and estimates the relative risk of disease. BMI is calculated by weight in kilograms divided by height in meters squared ($kg/m^2$). Overweight is typically defined as a BMI of 25–29.9 $kg/m^2$, and obesity is typically defined as a BMI of 30 $kg/m^2$. See, e.g., National Heart, Lung, and Blood Institute, Clinical Guidelines on the Identification, Evaluation, and Treatment of Overweight and Obesity in Adults, The Evidence Report, Washington, D.C.: U.S. Department of Health and Human Services, NIH publication no. 98-4083 (1998).

The increase in obesity is of concern because of the excessive health risks associated with obesity, including coronary heart disease, strokes, hypertension, type 2 diabetes mellitus, dyslipidemia, sleep apnea, osteoarthritis, gall bladder disease, depression, and certain forms of cancer (e.g., endometrial, breast, prostate, and colon). The negative health consequences of obesity make it the second leading cause of preventable death in the United States and impart a significant economic and psychosocial effect on society. See, McGinnis M, Foege W H., "Actual Causes of Death in the United States," *JAMA*, 270, 2207–12 (1993).

Obesity is now recognized as a chronic disease that requires treatment to reduce its associated health risks. Although weight loss is an important treatment outcome, one of the main goals of obesity management is to improve cardiovascular and metabolic values to reduce obesity-related morbidity and mortality. It has been shown that 5–10% loss of body weight can substantially improve metabolic values, such as blood glucose, blood pressure, and lipid concentrations. Hence, it is believed that a 5–10% intentional reduction in body weight may reduce morbidity and mortality.

Currently available prescription drugs for managing obesity generally reduce weight by inducing satiety or decreasing dietary fat absorption. Satiety is achieved by increasing synaptic levels of norepinephrine, serotonin, or both. For example, stimulation of serotonin receptor subtypes 1B, 1D, and 2C and 1- and 2-adrenergic receptors decreases food intake by regulating satiety. See, Bray G A, "The New Era of Drug Treatment. Pharmacologic Treatment of Obesity: Symposium Overview," *Obes Res.*, 3(suppl 4), 415s–7s (1995). Adrenergic agents (e.g., diethylpropion, benzphetamine, phendimetrazine, mazindol, and phentermine) act by modulating central norepinephrine and dopamine receptors through the promotion of catecholamine release. Older adrenergic weight-loss drugs (e.g., amphetamine, methamphetamine, and phenmetrazine), which strongly engage in dopamine pathways, are no longer recommended because of the risk of their abuse. Fenfluramine and dexfenfluramine, both serotonergic agents used to regulate appetite, are no longer available for use.

More recently, CB1 cannabinoid receptor antagonists/inverse agonists have been suggested as potential appetite suppressants. See, e.g., Arnone, M., et al., "Selective Inhibition of Sucrose and Ethanol Intake by SR141716, an Antagonist of Central Cannabinoid (CB1) Receptors," *Psychopharmacol*, 132, 104–106 (1997); Colombo, G., et al., "Appetite Suppression and Weight Loss after the Cannabinoid Antagonist SR141716," *Life Sci.*, 63, PL113–PL117 (1998); Simiand, J., et al., "SR141716, a CB1 Cannabinoid Receptor Antagonist, Selectively Reduces Sweet Food Intake in Marmose," *Behav. Pharmacol.*, 9, 179–181 (1998); and Chaperon, F., et al., "Involvement of Central Cannabinoid (CB1) Receptors in the Establishment of Place Conditioning in Rats," *Psychopharmacology*, 135, 324–332 (1998). For a review of cannabinoid CB1 and CB2 receptor modulators, see Pertwee, R. G., "Cannabinoid Receptor Ligands: Clinical and Neuropharmacological Considerations, Relevant to Future Drug Discovery and Development," *Exp. Opin. Invest. Drugs*, 9(7), 1553–1571 (2000).

Although investigations are on-going, there still exists a need for a more effective and safe therapeutic treatment for reducing or preventing weight-gain.

In addition to obesity, there also exists an unmet need for treatment of alcohol abuse. Alcoholism affects approximately 10.9 million men and 4.4 million women in the United States. Approximately 100,000 deaths per year have been attributed to alcohol abuse or dependence. Health risks associated with alcoholism include impaired motor control and decision making, cancer, liver disease, birth defects, heart disease, drug/drug interactions, pancreatitis and interpersonal problems. Studies have suggested that endogenous cannabinoid tone plays a critical role in the control of ethanol intake. The endogenous CB1 receptor antagonist SR-141716A has been shown to block voluntary ethanol intake in rats and mice. See, Arnone, M., et al., "Selective Inhibition of Sucrose and Ethanol Intake by SR141716, an Antagonist of Central Cannabinoid (CB1) Receptors," *Psychopharmacol*, 132, 104–106 (1997). For a review, see Hungund, B. L and B. S. Basavarajappa, "Are Anadamide and Cannabinoid Receptors involved in Ethanol Tolerance? A Review of the Evidence," *Alcohol & Alcoholism*. 35(2) 126–133, 2000.

Current treatments for alcohol abuse or dependence generally suffer from non-compliance or potential hepatotoxicity; therefore, there is a high unmet need for more effective treatment of alcohol abuse/dependence.

SUMMARY

The present invention provides compounds of Formula (I) or (II) that act as cannabinoid receptor ligands (in particular, CB1 receptor antagonists)

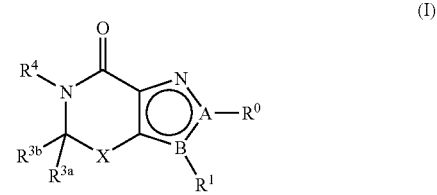

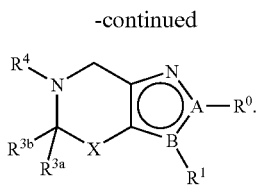

(II)

wherein

A is nitrogen and B is carbon, or A is carbon and B is nitrogen;

$R^0$ is an aryl optionally substituted with one or more substituents, or a heteroaryl optionally substituted with one or more substituents (preferably, $R^0$ is a substituted phenyl, more preferably a phenyl substituted with one to three substituents independently selected from the group consisting of halo (preferably, chloro or fluoro), $(C_1-C_4)$alkoxy, $(C_1-C_4)$alkyl, halo-substituted $(C_1-C_4)$alkyl (preferably fluoro-substituted alkyl), and cyano, most preferably, $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl);

$R^1$ is aryl optionally substituted with one or more substituents, heteroaryl optionally substituted with one or more substituents, —CH=CH—$R^{1a}$, or —CH$_2$CH$_2$—$R^{1a}$, where $R^{1a}$ is hydrogen or a chemical moiety selected from $(C_1-C_8)$ alkyl, 3- to 8-membered partially or fully saturated carbocyclic ring(s), 3- to 6-membered partially or fully saturated heterocycle, aryl, heteroaryl, where the chemical moiety is optionally substituted with one or more substituents;

X is a bond or —C($R^{2a}$)($R^{2b}$), where $R^{2a}$ and $R^{2b}$ are each independently hydrogen, $(C_1-C_4)$alkyl, or halo-substituted $(C_1-C_4)$alkyl (preferably, $R^{2a}$ and $R^{2b}$ are both hydrogen);

$R^{3a}$ and $R^{3b}$ are each independently hydrogen, $(C_1-C_4)$ alkyl, or halo-substituted $(C_1-C_4)$alkyl; and $R^4$ is a chemical moiety selected from the group consisting of $(C_1-C_8)$alkyl, aryl, heteroaryl, aryl$(C_1-C_4)$alkyl, a 3- to 8-membered partially or fully saturated carbocyclic ring(s), heteroaryl$(C_1-C_3)$alkyl, 5-6 membered lactone, 5- to 6-membered lactam, and a 3- to 8-membered partially or fully saturated heterocycle, where said chemical moiety is optionally substituted with one or more substituents;

a pharmaceutically acceptable salt thereof, a prodrug of the compound or the salt, or a solvate or hydrate of the compound, the salt or the prodrug.

In a preferred embodiment of the present invention, a compound of Formula (III) or (IV) is provided.

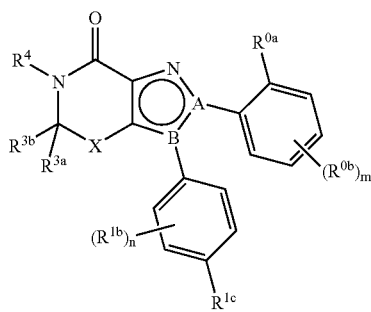

(III)

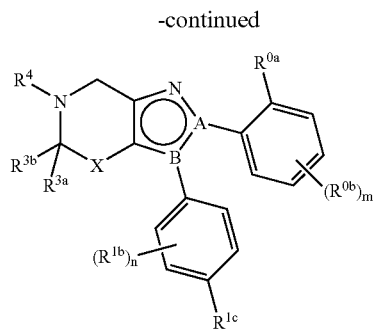

(IV)

wherein

A, B, X, $R^{2a}$, $R^{2b}$, $R^{3a}$, $R^{3b}$ and $R^4$ are as defined above; $R^{0a}$, $R^{0b}$, $R^{1b}$, and $R^{1c}$ are each independently halo, $(C_1-C_4)$alkoxy, $(C_1-C_4)$alkoxy, $(C_1-C_4)$alkyl, halo-substituted $(C_1-C_4)$alkyl, or cyano;

n and m are each independently 0, 1 or 2;

a pharmaceutically acceptable salt thereof, a prodrug of the compound or the salt, or a solvate or hydrate of the compound, the salt or the prodrug.

In preferred embodiments of the present invention, $R^4$ is a chemical moiety selected from the group consisting of $(C_1-C_8)$alkyl, aryl$(C_1-C_4)$alkyl, and 3- to 8-membered partially or fully saturated carbocyclic ring(s), where said chemical moiety is optionally substituted with one or more substituent.

More preferably, $R^4$ is $(C_1-C_8)$alkyl, halo-substituted $(C_1-C_8)$alkyl, cyclopentyl, cyclohexyl, piperidin-1-yl, pyrrolidin-1-yl, or morpholin-1-yl.

Preferably, $R^0$ and $R^1$ are each independently a phenyl substituted with 1 to 3 substituents independently selected from the group consisting of halo, $(C_1-C_4)$alkoxy, $(C_1-C_4)$ alkyl, halo-substituted $(C_1-C_4)$alkyl, and cyano;

More preferably, $R^0$ and $R^1$ are each independently a phenyl substituted with 1 to 2 substituents independently selected from the group consisting of chloro, fluoro, $(C_1-C_4)$ alkoxy, $(C_1-C_4)$alkyl, fluoro-substituted $(C_1-C_4)$alkyl), and cyano;

Most preferably, $R^0$ is 2-chlorophenyl, 2-fluorophenyl, 2,4-dichlorophenyl, 2-fluoro-4-chlorophenyl, 2-chloro-4-fluorophenyl, or 2,4-difluorophenyl; and $R^1$ is 4-chlorophenyl, 4-cyanophenyl or 4-fluorophenyl.

Preferred compounds of Formula (I) where A is nitrogen, B is carbon and X is a bond include: 2-(2-chloro-phenyl)-5-isopropyl-3-(3,4,5-trifluoro-phenyl)-4,5-dihydro-2H-pyrrolo[3,4-c]pyrazol-6-one; 2,3-bis-(2-chloro-phenyl)-5-isopropyl-4,5-dihydro-2H-pyrrolo[3,4-c]pyrazol-6-one; 2-(2-chloro-phenyl)-5-isopropyl-3-(4-methoxymethyl-phenyl)-4,5-dihydro-2H-pyrrolo[3,4-c]pyrazol-6-one; 2-(2-chloro-phenyl)-3-(2-fluoro-phenyl)-5-isopropyl-4,5-dihydro-2H-pyrrolo[3,4-c]pyrazol-6-one; 2-(2-chloro-phenyl)-5-isopropyl-3-(6-methoxy-pyridin-3-yl)-4,5-dihydro-2H-pyrrolo[3,4-c]pyrazol-6-one; 3-(3-chloro-4-fluoro-phenyl)-2-(2-chloro-phenyl)-5-isopropyl-4,5-dihydro-2H-pyrrolo[3,4-c]pyrazol-6-one; 2-(2-chloro-phenyl)-3-(4-fluoro-3-methyl-phenyl)-5-isopropyl-4,5-dihydro-2H-pyrrolo[3,4-c]pyrazol-6-one; 3-(4-chloro-phenyl)-2-(2-chloro-phenyl)-5-isopropyl-4,5-dihydro-2H-pyrrolo[3,4-c]pyrazol-6-one; 3-(4-chloro-phenyl)-2-(2-chloro-phenyl)-5-isopropyl-4-methyl-4,5-dihydro-2H-pyrrolo[3,4-c]pyrazol-6-one; 4-benzyl-3-(4-chloro-phenyl)-2-(2-chloro-phenyl)-5-isopropyl-4,5-dihydro-2H-pyrrolo[3,4-c]pyrazol-6-one; 5-tert-butyl-3-

(4-chloro-phenyl)-2-(2-chloro-phenyl)-4,5-dihydro-2H-pyrrolo[3,4-c]pyrazol-6-one; 3-(4-chloro-phenyl)-2-(2-chloro-phenyl)-5-cyclobutyl-4,5-dihydro-2H-pyrrolo[3,4-c]pyrazol-6-one; 3-(4-chloro-phenyl)-2-(2-chloro-phenyl)-5-cyclopentyl-4,5-dihydro-2H-pyrrolo[3,4-c]pyrazol-6-one; 3-(4-chloro-phenyl)-2-(2-chloro-phenyl)-5-cyclohexyl-4,5-dihydro-2H-pyrrolo[3,4-c]pyrazol-6-one; 3-(4-chloro-phenyl)-2-(2,4-dichloro-phenyl)-5-isopropyl-4,5-dihydro-2H-pyrrolo[3,4-c]pyrazol-6-one; 5-tert-butyl-3-(4-chloro-phenyl)-2-(2,4-dichloro-phenyl)-4,5-dihydro-2H-pyrrolo[3,4-c]pyrazol-6-one; 3-(4-chloro-phenyl)-5-cyclopentyl-2-(2,4-dichloro-phenyl)-4,5-diydro-2H-pyrrolo[3,4-c]pyrazol-6-one; 3-(2-chloro-phenyl)-2-(4-chloro-phenyl)-5-isopropyl-4,5-dihydro-2H-pyrrolo[3,4-c]pyrazol-6-one; 3-(2-chloro-phenyl)-2-(4-chloro-phenyl)-5-cyclopentyl-4,5-dihydro-2H-pyrrolo[3,4-c]pyrazol-6-one; 3-(2-chloro-phenyl)-2-(4-chloro-phenyl)-5-cyclohexyl-4,5-dihydro-2H-pyrrolo[3,4-c]pyrazol-6-one; 5-bicyclo[2.2.1]hept-2-yl-3-(2-chloro-phenyl)-2-(4-chloro-phenyl)-4,5-dihydro-2H-pyrrolo[3,4-c]pyrazol-6-one; 2-(4-chloro-phenyl)-5-cyclopentyl-3-(2-fluoro-phenyl)-4,5-dihydro-2H-pyrrolo[3,4-c]pyrazol-6-one; and 2-(4-chloro-phenyl)-5-cyclohexyl-3-(2-fluoro-phenyl)-4,5-dihydro-2H-pyrrolo[3,4-c]pyrazol-6-one; a pharmaceutically acceptable salt thereof, or a solvate or hydrate of said compound or said salt.

More preferred compounds include: 3-(4-Chloro-phenyl)-2-(2-chloro-phenyl)-5-isopropyl-4,5-dihydro-2H-pyrrolo[3,4-c]pyrazol-6-one; 3-(4-Chloro-phenyl)-2-(2-chloro-phenyl)-5-(2,2,2-trifluoro-ethyl )-4,5-dihydro-2H-pyrrolo[3,4-c]pyrazol-6-one; and 4-[2-(2-Chloro-phenyl)-5-isopropyl-6-oxo-2,4,5,6-tetrahydro-pyrrolo[3,4-c]pyrazol-3-yl]-benzonitrile; a pharmaceutically acceptable salt thereof, a solvate or hydrate of the compound or the salt.

Preferred compounds of Formula (I) where A is nitrogen, B is carbon and X is —C($R^{2a}$)$R^{2b}$— include: 3-(4-chloro-phenyl)-2-(2-chloro-phenyl)-6-isopropyl-2,4,5,6-tetrahydro-pyrazolo[3,4-c]pyridin-7-one; 3-(4-chloro-phenyl)-2-(2-chloro-phenyl)-6-(2,2,2-trifluoro-ethyl)-2,4,5,6-tetrahydro-pyrazolo[3,4-c]pyridin-7-one; 3-(4-chloro-phenyl)-2-(2-chloro-phenyl)-6-(2,2-difluoro-ethyl)-2,4,5,6-tetrahydro-pyrazolo[3,4-c]pyridin-7-one; and 3-(4-chloro-phenyl)-2-(2-chloro-phenyl)-6-(2-fluoro-ethyl)-2,4,5,6-tetrahydro-pyrazolo[3,4-c]pyridin-7-one; a pharmaceutically acceptable salt thereof, or a solvate or hydrate of the compound or the salt.

Preferred compounds of Formula (I) where A is carbon, B is nitrogen and X is a bond include: 2-(4-chloro-phenyl)-5-cyclopentyl-1-(2-fluoro-phenyl)-5,6-dihydro-1H-pyrrolo[3,4-d]imidazol-4-one; 2-(4-chloro-phenyl)-5-cyclopentyl-1-(2,4-dichloro-phenyl)-5,6-dihydro-1H-pyrrolo[3,4-d]imidazol-4-one; 2-(4-chloro-phenyl)-5-cyclohexyl-1-(2,4-dichloro-phenyl)-5,6-dihydro-1H-pyrrolo[3,4-d]imidazol-4-one; 2-(4-chloro-phenyl)-1-(2,4-dichloro-phenyl)-5-(2,2,2-trifluoro-ethyl)-5,6-dihydro-1H-pyrrolo[3,4-d]imidazol-4-one; 2-(4-chloro-phenyl)-1-(2-chloro-phenyl)-5-isopropyl-5,6-dihydro-1H-pyrrolo[3,4-d]imidazol-4-one; 2-(4-chloro-phenyl)-1-(2-chloro-phenyl)-5-cyclopentyl-5,6-dihydro-1H-pyrrolo[3,4-d]imidazol-4-one; 2-(4-chloro-phenyl)-1-(2-chloro-phenyl)-5-cyclohexyl-5,6-dihydro-1H-pyrrolo[3,4-d]imidazol-4-one; 2-(2-chloro-phenyl)-1-(4-chloro-phenyl)-5-cyclohexyl-5,6-dihydro-1H-pyrrolo[3,4-d]imidazol-4-one; 2-(4-chloro-phenyl)-5-cyclohexylmethyl-1-(2-fluoro-phenyl)-5,6-dihydro-1H-pyrrolo[3,4-d]imidazol-4-one; 5-cyclopentyl-2-(4-fluoro-phenyl)-1-(2-fluoro-phenyl)-5,6-dihydro-1H-pyrrolo[3,4-d]imidazol-4-one; 1-(2-chloro-phenyl)-5-cyclopentyl-2-(4-fluoro-phenyl)-5,6-dihydro-1H-pyrrolo[3,4-d]imidazol-4-one; 2-(2-chloro-phenyl)-1-(4-chloro-phenyl)-5-cyclopentyl-5,6-dihydro-1H-pyrrolo[3,4-d]imidazol-4-one; 2-(2-chloro-phenyl)-1-(4-chloro-phenyl)-5-cyclohexyl-5,6-dihydro-1H-pyrrolo[3,4-d]imidazol-4-one; and 1-(4-chloro-phenyl)-5-cyclohexyl-2-(2,4-dichloro-phenyl)-5,6-dihydro-1H-pyrrolo[3,4-d]imidazol-4-one; a pharmaceutically acceptable salt thereof, or a solvate or hydrate of the compound or the salt.

A more preferred compound is 2-(4-chloro-phenyl)-5-cyclopentyl-1-(2-fluoro-phenyl)-5,6-dihydro-1H-pyrrolo[3,4-d]imidazol-4-one; a pharmaceutically acceptable salt thereof, or a solvate or hydrate of the compound or the salt.

A preferred compound of Formula (I) where A is carbon, B is nitrogen and X is —C($R^{2a}$)$R^{2b}$— is 2-(4-chloro-phenyl)-1-(2-chloro-phenyl)-5-cyclopentyl-1,5,6,7-tetrahydro-imidazo[4,5-c]pyridin-4-one; a pharmaceutically acceptable salt thereof, or a solvate or hydrate of the compound or the salt.

Preferred compounds of Formula (I) where $R^1$ is —CH═CH—$R^{1a}$ include: 2-(2-chloro-phenyl)-3-[2-(4-chloro-phenyl)-vinyl]-5-isopropyl-4,5-dihydro-2H-pyrrolo[3,4-c]pyrazol-6-one; 2-(2-chloro-phenyl)-5-isopropyl-3-vinyl-4,5-dihydro-2H-pyrrolo[3,4-c]pyrazol-6-one; 2-(2-chloro-phenyl)-3-[2-(4-chloro-phenyl)-vinyl]-5-(2,2,2-trifluoro-ethyl)-4,5-dihydro-2H-pyrrolo[3,4-c]pyrazol-6-one; 2-(2-chloro-phenyl)-3-[2-(4-chloro-phenyl)-vinyl]-5-(2,2-difluoro-ethyl)-4,5-dihydro-2H-pyrrolo[3,4-c]pyrazol-6-one; and 2-(2-chloro-phenyl)-3-[2-(4-chloro-phenyl)-vinyl]-5-(2-fluoro-ethyl)-4,5-dihydro-2H-pyrrolo[3,4-c]pyrazol-6-one; a pharmaceutically acceptable salt thereof, or a solvate or hydrate of the compound or the salt.

Preferred compounds of Formula (II) include: 2-(4-chloro-phenyl)-5-cyclohexyl-3-(2-fluoro-phenyl)-2,4,5,6-tetrahydro-pyrrolo[3,4-c]pyrazole; 3-(4-chloro-phenyl)-5-cyclopentyl-2-(2,4-dichloro-phenyl)-2,4,5,6-tetrahydro-pyrrolo[3,4-c]pyrazole; and 3-(4-chloro-phenyl)-2-(2-chloro-phenyl)-5-isopropyl-2,4,5,6-tetrahydro-pyrrolo[3,4-c]pyrazole; a pharmaceutically acceptable salt thereof, or a solvate or hydrate of the compound or the salt.

Some of the compounds described herein may contain at least one chiral center; consequently, those skilled in the art will appreciate that all stereoisomers (e.g., enantiomers and diastereoisomers) of the compounds illustrated and discussed herein are within the scope of the present invention. In addition, tautomeric forms of the compounds are also within the scope of the present invention. Those skilled in the art will recognize that chemical moieties such as an alpha-amino ether or an alpha-chloro amine may be too unstable to isolate; therefore, such moieties do not form a part of this invention.

Compounds of the present invention have been shown to be useful cannabinoid receptor ligands (in particular, CB1 receptor antagonists). Accordingly, another aspect of the present invention is a pharmaceutical composition that comprises (1) a compound of the present invention, and (2) a pharmaceutically acceptable excipient, diluent, or carrier. Preferably, the composition comprises a therapeutically effective amount of a compound of the present invention. The composition may also contain at least one additional pharmaceutical agent (described herein). Preferred agents include nicotine receptor partial agonists, opioid antagonists (e.g., naltrexone and nalmefene), dopaminergic agents (e.g., apomorphine), attention deficit disorder (ADD including attention deficit hyperactivity disorder (ADHD)) agents (e.g., Ritalin™, Strattera™, Concerta™ and Adderall™), and anti-obesity agents (described herein below).

In yet another embodiment of the present invention, a method for treating a disease, condition or disorder modulated by a cannabinoid receptor (preferably, a CB1 receptor) antagonists in animals that includes the step of administering to an animal in need of such treatment a therapeutically effective amount of a compound of the present invention (or a pharmaceutical composition thereof).

Diseases, conditions, and/or disorders modulated by cannabinoid receptor antagonists include eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD/ADHD), Parkinson's disease, and type II diabetes. In a preferred embodiment, the method is used in the treatment of weight loss, obesity, bulimia, ADD/ADHD, Parkinson's disease, dementia, alcoholism, and/or tobacco abuse.

Compounds of the present invention may be administered in combination with other pharmaceutical agents. Preferred pharmaceutical agents include nicotine receptor partial agonists, opioid antagonists (e.g., naltrexone (including naltrexone depot), antabuse, and nalmefene), dopaminergic agents (e.g., apomorphine), ADD/ADHD agents (e.g., methylphenidate hydrochloride (e.g., Ritalin™ and Concerta™), atomoxetine (e.g., Strattera™), and amphetamines (e.g., Adderall™)) and anti-obesity agents, such as apo-B/MTP inhibitors, 11β-hydroxy steroid dehydrogenase-1 (11β-HSD type 1) inhibitors, peptide $YY_{3-36}$ or analogs thereof, MCR-4 agonists, CCK-A agonists, monoamine reuptake inhibitors, sympathomimetic agents, $\beta_3$ adrenergic receptor agonists, dopamine receptor agonists, melanocyte-stimulating hormone receptor analogs, 5-HT2c receptor agonists, melanin concentrating hormone receptor antagonists, leptin, leptin analogs, leptin receptor agonists, galanin receptor antagonists, lipase inhibitors, bombesin receptor agonists, neuropeptide-Y receptor antagonists (e.g., NPY Y5 receptor antagonists such as those described herein below), thyromimetic agents, dehydroepiandrosterone or analogs thereof, glucocorticoid receptor antagonists, orexin receptor antagonists, glucagon-like peptide-1 receptor agonists, ciliary neurotrophic factors, human agouti-related protein antagonists, ghrelin receptor antagonists, histamine 3 receptor antagonists or inverse agonists, and neuromedin U receptor agonists, and the like.

The combination therapy may be administered as (a) a single pharmaceutical composition which comprises a compound of the present invention, at least one additional pharmaceutical agent described herein and a pharmaceutically acceptable excipient, diluent, or carrier; or (b) two separate pharmaceutical compositions comprising (i) a first composition comprising a compound of the present invention and a pharmaceutically acceptable excipient, diluent, or carrier, and (ii) a second composition comprising at least one additional pharmaceutical agent described herein and a pharmaceutically acceptable excipient, diluent, or carrier. The pharmaceutical compositions may be administered simultaneously or sequentially and in any order.

In yet another aspect of the present invention, a pharmaceutical kit is provided for use by a consumer to treat diseases, conditions or disorders modulated by cannabinoid receptor antagonists in an animal. The kit comprises a) a suitable dosage form comprising a compound of the present invention; and b) instructions describing a method of using the dosage form to treat diseases, conditions or disorders that are modulated by cannabinoid receptor (in particular, the CB1 receptor) antagonists.

In yet another embodiment of the present invention is a pharmaceutical kit comprising: a) a first dosage form comprising (i) a compound of the present invention and (ii) a pharmaceutically acceptable carrier, excipient or diluent; b) a second dosage form comprising (i) an additional pharmaceutical agent described herein, and (ii) a pharmaceutically acceptable carrier, excipient or diluent; and c) a container.

Definitions

As used herein, the term "alkyl" refers to a hydrocarbon radical of the general formula $C_nH_{2n+1}$. The alkane radical may be straight or branched. For example, the term "$(C_1-C_6)$alkyl" refers to a monovalent, straight, or branched aliphatic group containing 1 to 6 carbon atoms (e.g., methyl, ethyl, n-propyl, i-propyl, n-butyl, i-butyl, s-butyl, t-butyl, n-pentyl, 1-methylbutyl, 2-methylbutyl, 3-methylbutyl, neopentyl, 3,3-dimethylpropyl, hexyl, 2-methylpentyl, and the like). Similarly, the alkyl portion (i.e., alkyl moiety) of an alkoxy, acyl (e.g., alkanoyl), alkylamino, dialkylamino, and alkylthio group have the same definition as above. When indicated as being "optionally substituted", the alkane radical or alkyl moiety may be unsubstituted or substituted with one or more substituents (generally, one to three substituents except in the case of halogen substituents such as perchloro or perfluoroalkyls) independently selected from the group of substituents listed below in the definition for "substituted." "Halo-substituted alkyl" refers to an alkyl group substituted with one or more halogen atoms (e.g., fluoromethyl, difluoromethyl, trifluoromethyl, perfluoroethyl, and the like). When substituted, the alkane radicals or alkyl moieties are preferably substituted with 1 to 3 fluoro substituents, or 1 or 2 substituents independently selected from $(C_1-C_3)$alkyl, $(C_3-C_6)$cycloalkyl, $(C_2-C_3)$alkenyl, aryl, heteroaryl, 3- to 6-membered heterocycle, chloro, cyano, hydroxy, $(C_1-C_3)$alkoxy, aryloxy, amino, $(C_1-C_6)$alkyl amino, di-$(C_1-C_4)$alkyl amino, aminocarboxylate (i.e., $(C_1-C_3)$alkyl-O—C(O)—NH—), hydroxy$(C_2-C_3)$alkylamino, or keto (oxo), and more preferably, 1 to 3 fluoro groups, or 1 substituent selected from $(C_1-C_3)$alkyl, $(C_3-C_6)$cycloalkyl, $(C_6)$aryl, 6-membered-heteroaryl, 3- to 6-membered heterocycle, $(C_1-C_3)$alkoxy, $(C_1-C_4)$alkyl amino or di-$(C_1-C_2)$alkyl amino.

The terms "partially or fully saturated carbocyclic ring" (also referred to as "partially or fully saturated cycloalkyl") refers to nonaromatic rings that are either partially or fully hydrogenated and may exist as a single ring, bicyclic ring or a spiral ring. Unless specified otherwise, the carbocyclic ring is generally a 3- to 8-membered ring. For example, partially or fully saturated carbocyclic rings (or cycloalkyl) include groups such as cyclopropyl, cyclopropenyl, cyclobutyl, cyclobutenyl, cyclopentyl, cyclopentenyl, cyclopentadienyl, cyclohexyl, cyclohexenyl, cyclohexadienyl, norbornyl (bicyclo[2.2.1]heptyl), norbornenyl, bicyclo[2.2.2]octyl, and the like. When designated as being "optionally substituted", the partially saturated or fully saturated cycloalkyl group may be unsubstituted or substituted with one or more substituents (typically, one to three substituents) independently selected from the group of substituents listed below in the definition for "substituted." A substituted carbocyclic ring also includes groups wherein the carbocyclic ring is fused to a phenyl ring (e.g., indanyl). The carbocyclic group may be attached to the chemical entity or moiety by any one of the carbon atoms within the carbocyclic ring system. When substituted, the carbocyclic group is preferably substituted with 1 or 2 substituents independently selected from $(C_1-C_3)$alkyl, $(C_2-C_3)$alkenyl, $(C_1-C_6)$alkylidenyl, aryl, heteroaryl, 3-to 6-membered heterocycle, chloro, fluoro, cyano, hydroxy, $(C_1-C_3)$alkoxy, aryloxy, amino, $(C_1-C_6)$alkyl amino, di-$(C_1-C_4)$alkyl amino, aminocarboxylate (i.e., $(C_1-C_3)$alkyl-O—C(O)—NH—), hydroxy$(C_2-C_3)$alkylamino, or keto (oxo), and more preferably 1 or 2 from substituents independently selected from $(C_1-C_2)$alkyl, 3- to 6-membered heterocycle, fluoro, $(C_1-C_3)$alkoxy, $(C_1-C_4)$alkyl amino or di-$(C_1-C_2)$alkyl amino. Similarly, any cycloalkyl portion of a group (e.g., cycloalkylalkyl, cycloalkylamino, etc.) has the same definition as above.

The term "partially saturated or fully saturated heterocyclic ring" (also referred to as "partially saturated or fully saturated heterocycle") refers to nonaromatic rings that are either partially or fully hydrogenated and may exist as a single ring, bicyclic ring or a spiral ring. Unless specified otherwise, the heterocyclic ring is generally a 3- to 6-membered ring containing 1 to 3 heteroatoms (preferably 1 or 2 heteroatoms) independently selected from sulfur, oxygen and/or nitrogen. Partially saturated or fully saturated heterocyclic rings include groups such as epoxy, aziridinyl, tetrahydrofuranyl, dihydrofuranyl, dihydropyridinyl, pyrrolidinyl, N-methylpyrrolidinyl, imidazolidinyl, imidazolinyl, piperidinyl, piperazinyl, pyrazolidinyl, 2H-pyranyl, 4H-pyranyl, 2H-chromenyl, oxazinyl, morpholino, thiomorpholino, tetrahydrothienyl, tetrahydrothienyl 1,1-dioxide, and the like. When indicated as being "optionally substituted", the partially saturated or fully saturated heterocycle group may be unsubstituted or substituted with one or more substituents (typically, one to three substituents) independently selected from the group of substituents listed below in the definition for "substituted." A substituted heterocyclic ring includes groups wherein the heterocyclic ring is fused to an aryl or heteroaryl ring (e.g., 2,3-dihydrobenzofuranyl, 2,3-dihydroindolyl, 2,3-dihydrobenzothiophenyl, 2,3-dihydrobenzothiazolyl, etc.). When substituted, the heterocycle group is preferably substituted with 1 or 2 substituents independently selected from $(C_1-C_3)$alkyl, $(C_3-C_6)$cycloalkyl, $(C_2-C_4)$alkenyl, aryl, heteroaryl, 3- to 6-membered heterocycle, chloro, fluoro, cyano, hydroxy, $(C_1-C_3)$alkoxy, aryloxy, amino, $(C_1-C_6)$alkyl amino, di-$(C_1-C_3)$alkyl amino, aminocarboxylate (i.e., $(C_1-C_3)$alkyl-O—C(O)—NH—), or keto (oxo), and more preferably with 1 or 2 substituents independently selected from $(C_1-C_3)$alkyl, $(C_3-C_6)$cycloalkyl, $(C_6)$aryl, 6-membered-heteroaryl, 3- to 6-membered heterocycle, or fluoro. The heterocyclic group may be attached to the chemical entity or moiety by any one of the ring atoms within the heterocyclic ring system. Similarly, any heterocycle portion of a group (e.g., heterocycle-substituted alkyl, heterocycle carbonyl, etc.) has the same definition as above.

The term "aryl" or "aromatic carbocyclic ring" refers to aromatic moieties having a single (e.g., phenyl) or a fused ring system (e.g., naphthalene, anthracene, phenanthrene, etc.). A typical aryl group is a 6- to 10-membered aromatic carbocyclic ring(s). When indicated as being "optionally substituted", the aryl groups may be unsubstituted or substituted with one or more substituents (preferably no more than three substituents) independently selected from the group of substituents listed below in the definition for "substituted." Substituted aryl groups include a chain of aromatic moieties (e.g., biphenyl, terphenyl, phenylnaphthalyl, etc.). When substituted, the aromatic moieties are preferably substituted with 1 or 2 substituents independently selected from $(C_1-C_4)$alkyl, $(C_2-C_3)$alkenyl, aryl, heteroaryl, 3- to 6-membered heterocycle, bromo, chloro, fluoro, iodo, cyano, hydroxy, $(C_1-C_4)$alkoxy, aryloxy, amino, $(C_1-C_6)$alkyl amino, di-$(C_1-C_3)$alkyl amino, or aminocarboxylate (i.e., $(C_1-C_3)$alkyl-O—C(O)—NH—), and more preferably, 1 or 2 substituents independently selected from $(C_1-C_4)$alkyl, chloro, fluoro, cyano, hydroxy, or $(C_1-C_4)$alkoxy. The aryl group may be attached to the chemical entity or moiety by any one of the carbon atoms within the aromatic ring system. Similarly, the aryl portion (i.e., aromatic moiety) of an aroyl or aroyloxy (i.e., (aryl)-C(O)—O—) has the same definition as above.

The term "heteroaryl" or "heteroaromatic ring" refers to aromatic moieties containing at least one heteratom (e.g., oxygen, sulfur, nitrogen or combinations thereof) within a 5- to 10-membered aromatic ring system (e.g., pyrrolyl, pyridyl, pyrazolyl, indolyl, indazolyl, thienyl, furanyl, benzofuranyl, oxazolyl, imidazolyl, tetrazolyl, triazinyl, pyrimidyl, pyrazinyl, thiazolyl, purinyl, benzimidazolyl, quinolinyl, isoquinolinyl, benzothiophenyl, benzoxazolyl, etc.). The heteroaromatic moiety may consist of a single or fused ring system. A typical single heteroaryl ring is a 5- to 6-membered ring containing one to three heteroatoms independently selected from oxygen, sulfur and nitrogen and a typical fused heteroaryl ring system is a 9- to 10-membered ring system containing one to four heteroatoms independently selected from oxygen, sulfur and nitrogen. When indicated as being "optionally substituted", the heteroaryl groups may be unsubstituted or substituted with one or more substituents (preferably no more than three substituents) independently selected from the group of substituents listed below in the definition for "substituted." When substituted, the heteroaromatic moieties are preferably substituted with 1 or 2 substituents independently selected from $(C_1-C_4)$alkyl, $(C_2-C_3)$alkenyl, aryl, heteroaryl, 3- to 6-membered heterocycle, bromo, chloro, fluoro, iodo, cyano, hydroxy, $(C_1-C_4)$alkoxy, aryloxy, amino, $(C_1-C_6)$alkyl amino, di-$(C_1-C_3)$alkyl amino, or aminocarboxylate (i.e., $(C_1-C_3)$alkyl-O—C(O)—NH—), and more preferably, 1 or 2 substituents independently selected from $(C_1-C_4)$alkyl, chloro, fluoro, cyano, hydroxy, $(C_1-C_4)$alkoxy, $(C_1-C_4)$alkyl amino or di-$(C_1-C_2)$alkyl amino. The heteroaryl group may be attached to the chemical entity or moiety by any one of the atoms within the aromatic ring system (e.g., imidazol-1-yl, imidazol-2-yl, imidazol-4-yl, imidazol-5-yl, pyrid-2-yl, pyrid-3-yl, pyrid-4-yl, pyrid-5-yl, or pyrid-6-yl). Similarly, the heteroaryl portion (i.e., heteroaromatic moiety) of a heteroaroyl or heteroaroyloxy (i.e., (heteroaryl)-C(O)—O—) has the same definition as above.

The term "acyl" refers to hydrogen, alkyl, partially saturated or fully saturated cycloalkyl, partially saturated or fully saturated heterocycle, aryl, and heteroaryl substituted carbonyl groups. For example, acyl includes groups such as $(C_1-C_6)$alkanoyl (e.g., formyl, acetyl, propionyl, butyryl, valeryl, caproyl, t-butylacetyl, etc.), $(C_3-C_6)$cycloalkylcarbonyl (e.g., cyclopropylcarbonyl, cyclobutylcarbonyl, cyclopentylcarbonyl, cyclohexylcarbonyl, etc.), heterocyclic carbonyl (e.g., pyrrolidinylcarbonyl, pyrrolid-2-one-5-carbonyl, piperidinylcarbonyl, piperazinylcarbonyl, tetrahydrofuranylcarbonyl, etc.), aroyl (e.g., benzoyl) and heteroaroyl (e.g., thiophenyl-2-carbonyl, thiophenyl-3-carbonyl, furanyl-2-carbonyl, furanyl-3-carbonyl, 1H-pyrroyl-2-carbonyl, 1H-pyrroyl-3-carbonyl, benzo[b]thiophenyl-2-carbonyl, etc.). In addition, the alkyl, cycloalkyl, heterocycle, aryl and heteroaryl portion of the acyl group may be any one of the groups described in the respective definitions above. When indicated as being "optionally substituted", the acyl group may be unsubstituted or optionally substituted with one or more substituents (typically, one to three substituents) independently selected from the group of substituents listed below in the definition for "substituted" or the alkyl, cycloalkyl, heterocycle, aryl and heteroaryl portion of the acyl group may be substituted as described above in the preferred and more preferred list of substituents, respectively.

The term "substituted" specifically envisions and allows for one or more substitutions that are common in the art. However, it is generally understood by those skilled in the art that the substituents should be selected so as to not adversely affect the pharmacological characteristics of the compound or adversely interfere with the use of the medicament. Suitable substituents for any of the groups defined above include $(C_1-C_6)$alkyl, $(C_3-C_7)$cycloalkyl, $(C_2-C_6)$alkenyl, $(C_1-C_6)$alkylidenyl, aryl, heteroaryl, 3- to 6-membered heterocycle, halo (e.g., chloro, bromo, iodo and fluoro), cyano, hydroxy, $(C_1-C_6)$alkoxy, aryloxy, sulfhydryl (mercapto), $(C_1-C_6)$alkylthio, arylthio, amino, mono- or di-$(C_1-C_6)$alkyl amino, quaternary ammonium salts, amino $(C_1-C_6)$alkoxy, aminocarboxylate (i.e., $(C_1-C_6)$alkyl-O—C(O)—NH—), hydroxy$(C_2-C_6)$alkylamino, amino$(C_1-C_6)$alkylthio, cyanoamino, nitro, $(C_1-C_6)$carbamyl, keto (oxo), acyl, $(C_1-C_6)$alkyl-$CO_2$—, glycolyl, glycyl, hydrazino, guanyl, sulfamyl, sulfonyl, sulfinyl, thio$(C_1-C_6)$alkyl-C(O)—, thio$(C_1-C_6)$alkyl-$CO_2$—, and combinations thereof. In the case of substituted combinations, such as "substituted aryl $(C_1-C_6)$alkyl", either the aryl or the alkyl group may be substituted, or both the aryl and the alkyl groups may be substituted with one or more substituents (typically, one to three substituents except in the case of perhalo substitutions). An aryl or heteroaryl substituted carbocyclic or heterocyclic group may be a fused ring (e.g., indanyl, dihydrobenzofuranyl, dihydroindolyl, etc.).

The term "solvate" refers to a molecular complex of a compound represented by Formula (I) or (II) (including prodrugs and pharmaceutically acceptable salts thereof) with one or more solvent molecules. Such solvent molecules are those commonly used in the pharmaceutical art, which are known to be innocuous to the recipient, e.g., water, ethanol, and the like. The term "hydrate" refers to the complex where the solvent molecule is water.

The term "protecting group" or "Pg" refers to a substituent that is commonly employed to block or protect a particular functionality while reacting other functional groups on the compound. For example, an "amino-protecting group" is a substituent attached to an amino group that blocks or protects the amino functionality in the compound. Suitable amino-protecting groups include acetyl, trifluoroacetyl, t-butoxycarbonyl (BOC), benzyloxycarbonyl (CBz) and 9-fluorenylmethylenoxycarbonyl (Fmoc). Similarly, a "hydroxy-protecting group" refers to a substituent of a hydroxy group that blocks or protects the hydroxy functionality. Suitable protecting groups include acetyl and silyl. A "carboxy-protecting group" refers to a substituent of the carboxy group that blocks or protects the carboxy functionality. Common carboxy-protecting groups include —$CH_2CH_2SO_2Ph$, cyanoethyl, 2-(trimethylsilyl)ethyl, 2-(trimethylsilyl)ethoxymethyl, 2-(p-toluenesulfonyl)ethyl, 2-(p-nitrophenylsulfenyl)ethyl, 2-(diphenylphosphino)-ethyl, nitroethyl and the like. For a general description of protecting groups and their use, see T. W. Greene, *Protective Groups in Organic Synthesis,* John Wiley & Sons, New York, 1991.

The phrase "therapeutically effective amount" means an amount of a compound of the present invention that (i) treats or prevents the particular disease, condition, or disorder, (ii) attenuates, ameliorates, or eliminates one or more symptoms of the particular disease, condition, or disorder, or (iii) prevents or delays the onset of one or more symptoms of the particular disease, condition, or disorder described herein.

The term "animal" refers to humans (male or female), companion animals (e.g., dogs, cats and horses), food-source animals, zoo animals, marine animals, birds and other similar animal species. "Edible animals" refers to food-source animals such as cows, pigs, sheep and poultry. The phrase "pharmaceutically acceptable" indicates that the substance or composition must be compatible chemically and/or toxicologically, with the other ingredients comprising a formulation, and/or the mammal being treated therewith.

The terms "treating", "treat", or "treatment" embrace both preventative, i.e., prophylactic, and palliative treatment.

The terms "modulated by a cannabinoid receptor" or "modulation of a cannabinoid receptor" refers to the activation or deactivation of a cannabinoid receptor. For example, a ligand may act as an agonist, partial agonist, inverse agonist, antagonist, or partial antagonist.

The term "antagonist" includes both full antagonists and partial antagonists, as well as inverse agonists.

The term "CB-1 receptor" refers to the G-protein coupled type 1 cannabinoid receptor.

The term "compounds of the present invention" (unless specifically identified otherwise) refer to compounds of Formulae (I), (II), (III), and (IV), prodrugs thereof, pharmaceutically acceptable salts of the compounds, and/or prodrugs, and hydrates or solvates of the compounds, salts, and/or prodrugs, as well as, all stereoisomers (including diastereoisomers and enantiomers), tautomers and isotopically labeled compounds.

As used herein, structures drawn with circles within a ring designate aromaticity. For example, the following chemical moiety designates a pyrazole ring when A is a nitrogen and B is a carbon; and the chemical moiety designates an imidazole when A is a carbon and B is a nitrogen.

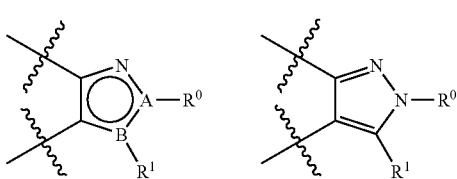

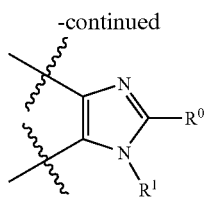

DETAILED DESCRIPTION

The present invention provides compounds and pharmaceutical formulations thereof that are useful in the treatment of diseases, conditions and/or disorders modulated by cannabinoid receptor antagonists.

Compounds of the present invention may be synthesized by synthetic routes that include processes analogous to those well-known in the chemical arts, particularly in light of the description contained herein. The starting materials are generally available from commercial sources such as Aldrich Chemicals (Milwaukee, Wis.) or are readily prepared using methods well known to those skilled in the art (e.g., prepared by methods generally described in Louis F. Fieser and Mary Fieser, *Reagents for Organic Synthesis*, v. 1–19, Wiley, N.Y. (1967–1999 ed.), or *Beilsteins Handbuch der organischen Chemie*, 4, Aufl. ed. Springer-Verlag, Berlin, including supplements (also available via the Beilstein online database)).

For illustrative purposes, the reaction schemes depicted below provide potential routes for synthesizing the compounds of the present invention as well as key intermediates. For a more detailed description of the individual reaction steps, see the Examples section below. Those skilled in the art will appreciate that other synthetic routes may be used to synthesize the inventive compounds. Although specific starting materials and reagents are depicted in the schemes and discussed below, other starting materials and reagents can be easily substituted to provide a variety of derivatives and/or reaction conditions. In addition, many of the compounds prepared by the methods described below can be further modified in light of this disclosure using conventional chemistry well known to those skilled in the art.

In the preparation of compounds of the present invention, protection of remote functionality (e.g., primary or secondary amine) of intermediates may be necessary. The need for such protection will vary depending on the nature of the remote functionality and the conditions of the preparation methods. Suitable amino-protecting groups (NH-Pg) include acetyl, trifluoroacetyl, t-butoxycarbonyl (BOC), benzyloxycarbonyl (CBz) and 9-fluorenylmethyleneoxycarbonyl (Fmoc). The need for such protection is readily determined by one skilled in the art. For a general description of protecting groups and their use, see T. W. Greene, *Protective Groups in Organic Synthesis*, John Wiley & Sons, New York, 1991.

Scheme I outlines the general procedures one could use to provide compounds of the present invention where A is nitrogen, B is carbon, X is a bond and $R^{3a}$ and $R^{3b}$ are both hydrogen.

Scheme I

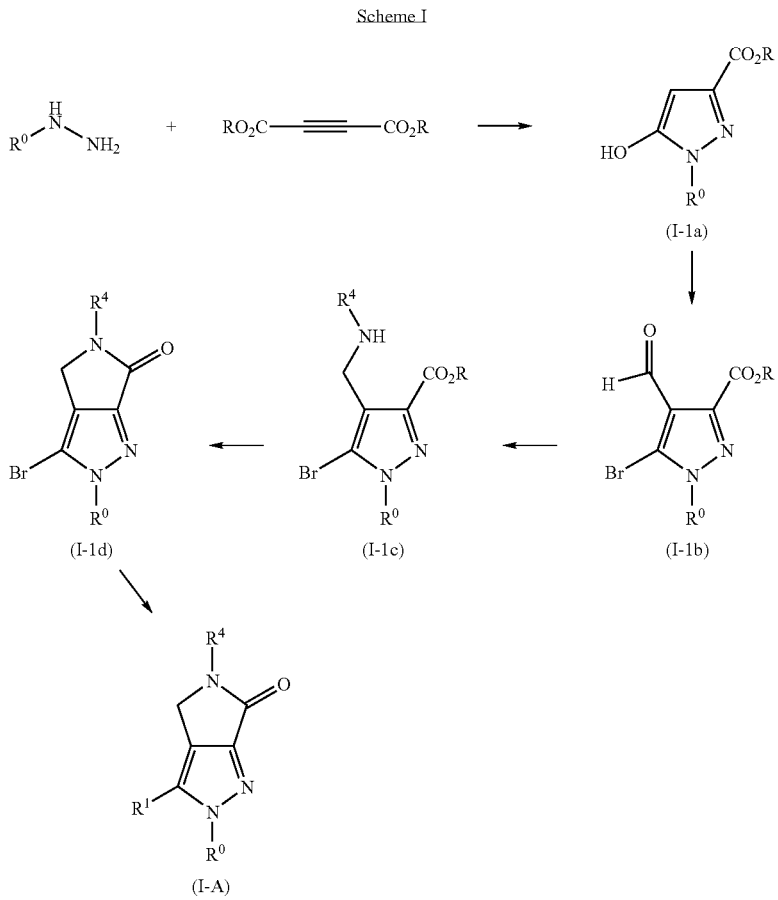

The pyrazole intermediate I-1a may be prepared by cyclizing the desired hydrazine with acetylene dicarboxylate in the presence of a weak base (e.g., alkali metal carbonate, such as potassium carbonate) in a protic solvent (e.g., ethanol) under refluxing conditions. Intermediate I-1b may then be produced by treating the pyrazole intermediate I-1a with phosphorus oxybromide in the presence of dimethylformamide (DMF) in an aprotic solvent (e.g., 1,2-dichloroethane) with heat. The amino group ($R^4$—NH) may then be introduced into the molecule by treating the formyl compound I-1b with the desired amine ($R^4$—NH) in the presence of sodium triacetoxy-borohydride and a weak acid (e.g., acetic acid). A variety of suitable amine compounds are available commercially or easily synthesized using procedures well documented in the literature. The lactam may then be formed by hydrolyzing the pendant ester group and condensing the pendant amino group with the carboxylic acid function to form the amide linkage. The lactam formation may be accomplished using procedures well known to those skilled in the art. For example, the carboxylate ester intermediate I-1c may be hydrolyzed using a strong base (e.g., alkali metal hydroxide) in a polar solvent (e.g., ethanol) with heat. The amide linkage can then be formed by treating the resulting carboxylic acid with 1-propanephosphoric acid cyclic anhydride in the presence of a nonreactive base (e.g., triethylamine). Finally, the $R^1$ group is introduced into the molecule by displacing the bromo group with the desired $R^1$ group. This may be accomplished by treating the bromo intermediate I-1d with either the desired boronic acid ($R^1$—B(OH)$_2$) or tin reagent ($R^1$SnR$_3$) in the presence of cesium fluoride and tetrakis(triphenylphosphine)palladium(0) in a polar solvent (1,2-dimethoxyethane) at elevated temperatures (e.g., 100° C.).

Alternatively, compounds of the present invention where A is nitrogen, B is carbon and X is a bond, may be prepared using the procedures outlined below in Scheme II. Scheme II also illustrates the introduction of a vinyl moiety at the $R^1$ position which can be further modified by reducing the olefin functionality.

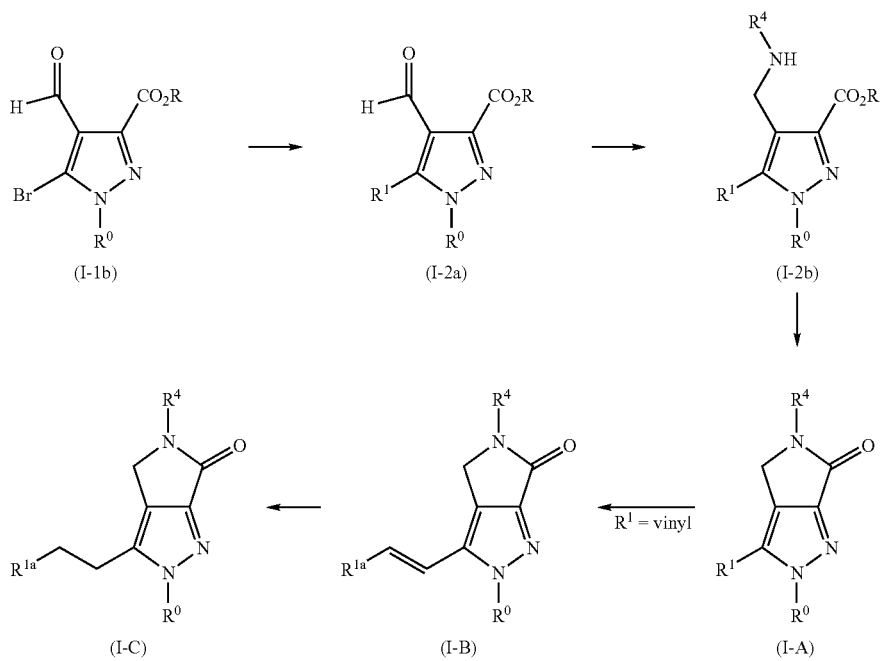

Scheme II

In Scheme II, the $R^1$ moiety is introduced earlier in the synthetic scheme. Using the same basic procedures described above for the displacement of the bromo group in intermediate I-1d, intermediate I-1b may be treated with the appropriate boronic acid or tin reagent to produce intermediate I-2a. The desired amine functionality may then be introduced, followed by hydrolysis to the corresponding carboxylic acid, and then cyclization to the lactam using the same general procedures discussed above in Scheme I. When $R^1$ of Compound I-A is a vinyl group, the compound may be further modified by reacting the vinyl group with the desired aryl halide (e.g., bromide or iodide) or heteroaryl halide (e.g., bromide or iodide) in the presence of palladium acetate. Compound I-B may be further modified by reducing the double bond in the pendant group ($R^{1a}$—CH=CH—) of Compound I-B using standard reduction procedures, such as those described in *J. Amer. Chem Soc.*, 91, 5769 (1969). For example, Compound I-B is refluxed in 2-ethoxyethanol in the presence of p-toluenesulfonylhydrazine.

Scheme III below illustrates the preparation of compounds of the present invention where A is a nitrogen, B is carbon and X is —(C($R^{2a}$)($R^{2b}$))—.

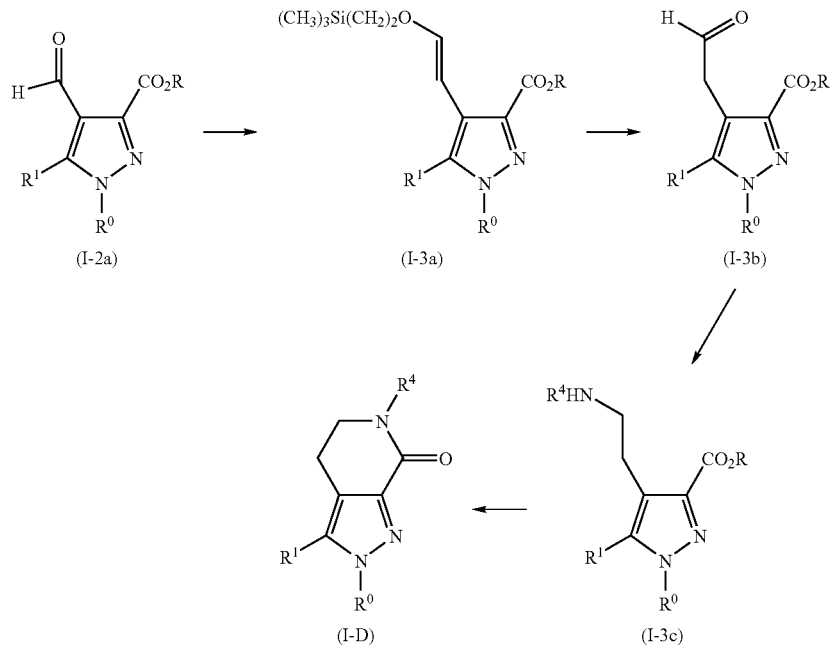

An extra methylene is introduced in the molecule by first reacting intermediate I-2a with (2-(trimethylsilyl)ethoxymethyl)triphenyl-phosphonium chloride in the presence of sodium hydride to form the siloxy intermediate I-3a. The siloxy group may then be removed by treating intermediate I-3a with a strong acid (e.g., conc. hydrofluoric acid). The desired amino functionality may then be introduced by treating intermediate I-3b with the appropriate amine ($R^4NH_2$) using procedures discussed above (e.g, treatment with sodium triacetoxyborohydride and acetic acid, in 1,2-dichloroethane). Cyclization to the lactam may be accomplished by first hydrolyzing the ester to the carboxylic acid and then cyclizing to the lactam using procedures analogous to those discussed above (e.g., (1) treatment with KOH, EtOH, heat, then acidification; and (2) treatment with 1-propanephosphoric acid cyclic anhydride and triethylamine in dichloromethane).

Scheme IV provides an alternative route for the synthesis of compounds of the present invention where A is nitrogen, B is carbon and X is a bond.

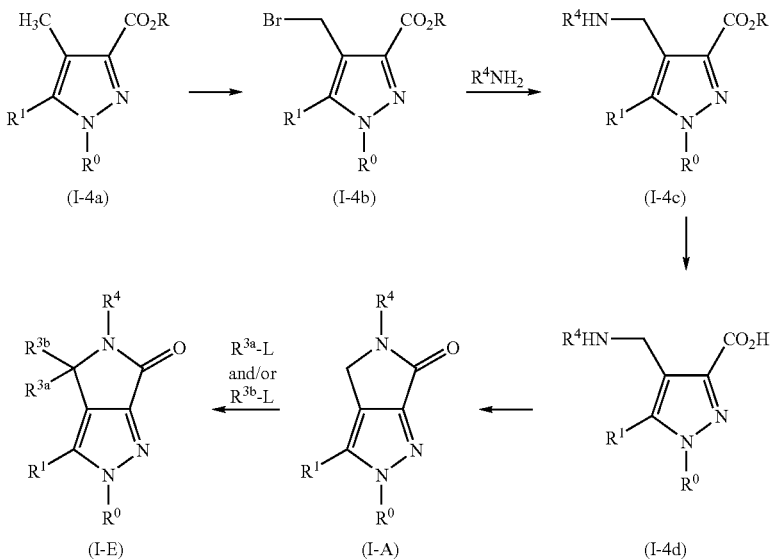

Starting material I-4a may be prepared using procedures described by Barth, et al., in European Application EP656354. The halo group (e.g., bromo) may be introduced onto the pendant methyl group using procedures analogous to those described by Barth, et al., in PCT application WO97/19063. For example, starting material I-4a may be treated with 2,2'-azobisisobutyronitrile (AIBN) in carbon tetrachloride at elevated temperatures. The bromo group in I-4b may then be displaced with the desired amino functionality using the same general procedures discussed above. The compound I-A can be formed by first hydrolyzing the ester group of I-4c, followed by formation of the amide linkage using the general procedures discussed earlier. Compound I-A may be further modified by attaching one or two pendant groups on the carbon adjacent to the lactam nitrogen by treating Compound I-A with the desired reagents ($R^{2a}$-L and/or $R^{2a}$-L, where L is a leaving group, such a halo group (e.g., bromo)) in the presence of potassium hexamethyldisilazide (KHMDSi) as described in *Tet. Lett.* (1998), 39, 2319–2320.

Scheme V illustrates a synthetic route for the preparation of compounds of the present invention where A is carbon, B is nitrogen and X is a bond, as well as the introduction of $R^{3a}$ and/or $R^{3b}$.

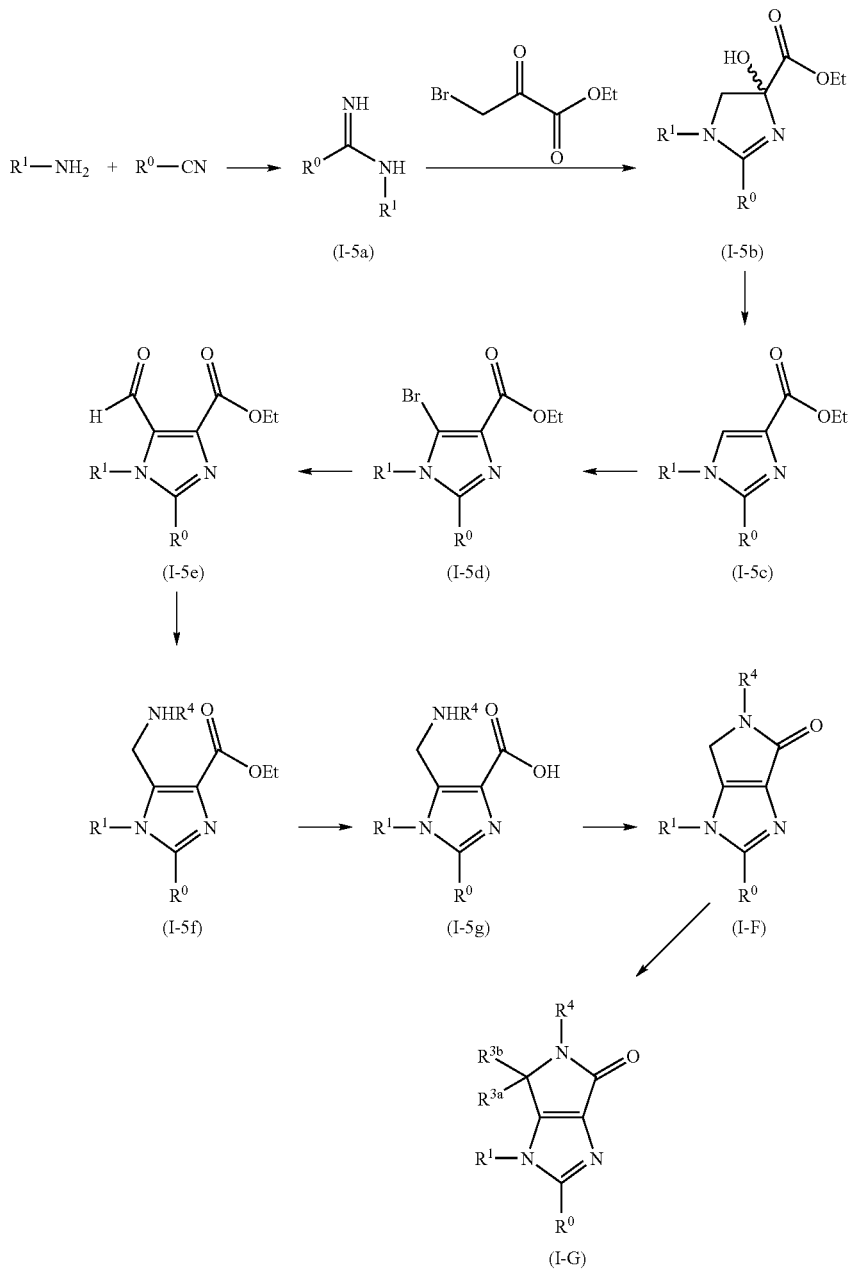

Intermediate I-5a is prepared by treating the appropriate amine having the desired $R^1$ group with trimethylaluminum under inert atmospheric conditions followed by condensation with the appropriate cyanide having the desired $R^0$ group. Suitable amines include substituted phenyl amines (e.g., 4-chlorophenyl amine, 4-fluorophenyl amine, 4-bromophenyl amine, 4-iodophenyl amine, 4-cyanophenyl amine, and the like) pyridin-2-yl amine, pyridin-3-yl amine, pyridin-4-yl amine, substituted pyridinyl amines (e.g., 2-dimethylaminopyridin-5-yl amine, 2-methoxypyridin-5-yl amine, 5-chloropyridin-2-yl amine, 5-methylpyridin-2-yl, 5-methoxypyridin-2-yl amine, 3-chloropyridin-4-yl; amine, 2-N-morpholinylpyridin-5-yl, and the like), and other commercially available or easily synthesized substituted or unsubstituted aryl and heteroaryl amines. Suitable cyano compounds include substituted benzonitriles (e.g., 2-chlorobenzonitrile, 2-fluorobenzonitrile, 2-methoxybenzonitrile, 2-methylbenzonitrile, 2,4-dichlorobenzonitrile, 2,4-difluorobenzonitrile, 2-chloro-4-fluorobenzonitrile, 2-chloro-4-methylbenzonitrile, 2,4-dimethoxybenzonitrile, 2-methyl-4-chlorobenzonitrile, and the like), cyano-substituted pyridines (e.g., 4-cyano-3-chloropyridine) and other commercially available or easily synthesized substituted or unsubstituted aryl or heteroaryl nitriles.

Intermediate I-5a may then be condensed with a 3-bromo-2-oxo-propionic acid ester to produce the cyclized 4-hydroxy-4,5-dihydro-1H-imidazole ester I-5b using procedures analogous to those described by Khanna, I. K., et al., in *J. Med. Chem.*, 40, 1634 (1997). For example, the amidine intermediate I-5a is refluxed in a polar solvent (e.g., isopropanol) in the presence of a mild base (e.g., sodium bicarbonate). Generally, the reaction (i.e., cyclization followed by dehydration) procedes directly to the desired imidazole ester intermediate I-5c. In some instances, it may be necessary to dehydrate the initial carbinol condensation product I-5b with an acid catalyst (e.g., toluene sulfonic acid in refluxing toluene) to provide the desired imidazole ester I-5c.

The imidazole ester I-5c is prepared from the 4-hydroxy-4,5-dihydro intermediate I-5b using standard dehydration procedures well-known to those skilled in the art. For example, intermediate I-5b may be treated with p-toluenesulfonic acid monohydrate in refluxing toluene. Alternatively, intermediate I-5b may be treated with methanesulfonyl chloride in the presence of a base (e.g., triethylamine). The bromo group may be introduced into intermediate I-5c by treating with bromine following a procedure described in *J. Het Chem*, 34(3), 765–771 (1997). The bromo group of I-5c may then be converted to a formyl group to produce intermediate I-5d by first treating intermediate I-5c with a strong base (e.g., n-butyl lithium) followed by treatment with DMF. The amino functionality may then be introduced using procedures analogous to those discussed earlier for the pyrazole compounds. For example, intermediate I-5d may be reacted with the desired amine ($R^4$—$NH_2$) in the presence of $NaBH(OAc)_3$ to produce intermediate I-5e. The amino intermediate I-5e may then be cyclized to form the lactam by first hydrolyzing the ester group to its corresponding carboxylic acid followed by the formation of the amide linkage using procedures analogous to those discussed above for the pyrazole derivatives. Compound I-F may be further modified by attaching pendant $R^{3a}$ and/or $R^{3b}$ groups using procedures analogous to those discussed above. For example, treatment of Compound I-F with the desired reagents ($R^{2a}$-L and/or $R^{2a}$-L, where L is a leaving group, such a halo group (e.g., bromo)) in the presence of a base such as KHMDSi.

Scheme VI illustrates the preparation of compounds of the present invention where A is carbon, B is nitrogen (imidazole) and X is —$C(R^{2a})(R^{2b})$—.

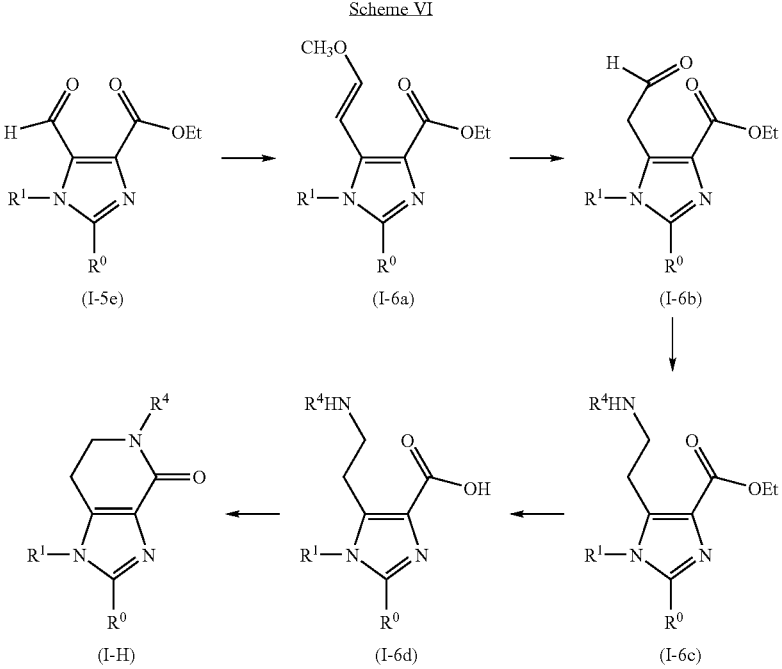

Scheme VI

The imidazole compound I-H may be prepared using procedures analogous to those discussed above for the preparation of the pyrazole derivative (I-D). An extra methylene is introduced in the molecule by first reacting intermediate I-5e with the ylid formed from lithium hexamethyldisilazide and (methoxymethyl)triphenylphosphonium chloride to produce the vinyl ether I-6a. The vinyl ether is converted to the corresponding aldehyde by heating the vinyl ether intermediate in an acidic environment. The amino functionality ($R^4$—NH) may then be introduced and the lactam ring formed using procedures analogous to those discussed above. As discussed above, the lactam may be formed by first hydrolyzing the ester, followed by formation of the amide linkage to produce Compound I-H.

Compounds of Formula I wherein $R^4$ is an optionally substituted piperidinyl or pyrrolidinyl group can be prepared as shown in Scheme VII.

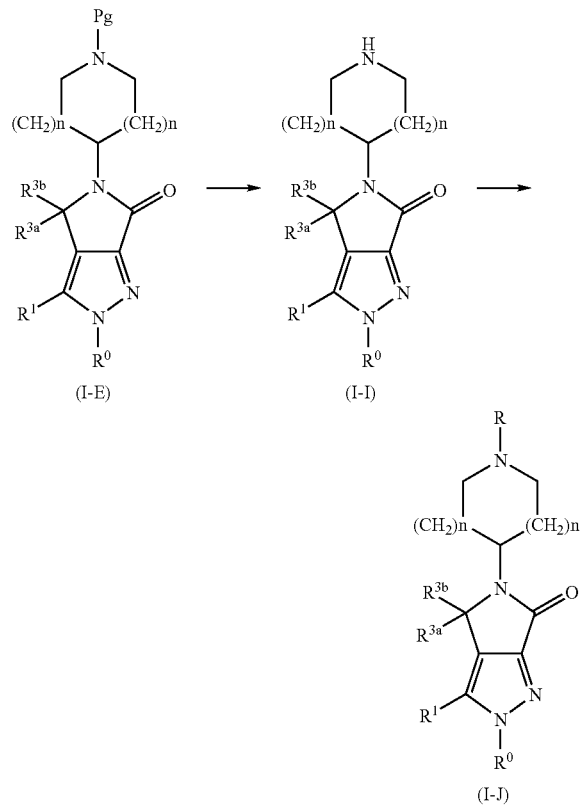

Removal of the protecting group in Compound I-E can be accomplished by methods known in the art to give bicyclic amino derivatives such as I-I which can be subsequently reacted with alkyl halides in the presence of a suitable base such as potassium carbonate in a solvent such as DMF or treated with acid chlorides or sulfonyl chlorides in the presence of a base such as triethylamine in a non-polar solvent such as $CH_2Cl_2$ to give compounds such as I-J. Compound I-E can also be reacted with an aldehyde or ketone derivative in the presence of a reducing agent such as $NaBH(OAc)_3$ as previously described to produce intermediate I-J.

Compounds of formulae II-A and II-B can be prepared as shown in Scheme VII.

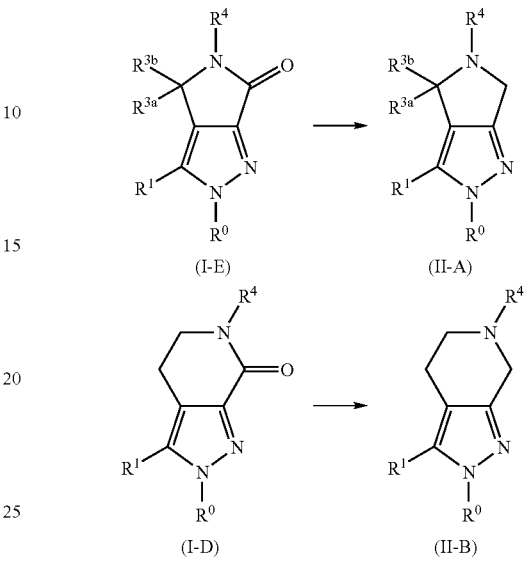

The pyrazole compound I-E is treated with a suitable reducing agent such as lithium aluminum hydride or borane ($BH_3$) in a polar, aprotic solvent such as THF at temperatures ranging from about 0° C. to about 100° C. to give compounds such as II-A. Compound II-B can be prepared from I-D using a similar reduction procedure. The imidazole compounds of formula II (A is carbon and B is nitrogen) may be prepared using analogous procedures.

Conventional methods and/or techniques of separation and purification known to one of ordinary skill in the art can be used to isolate the compounds of the present invention, as well as the various intermediates related thereto. Such techniques will be well known to one of ordinary skill in the art and may include, for example, all types of chromatography (high pressure liquid chromatography (HPLC), column chromatography using common adsorbents such as silica gel, and thin-layer chromatography), recrystallization, and differential (i.e., liquid-liquid) extraction techniques.

The compounds of the present invention may be isolated and used per se or in the form of its pharmaceutically acceptable salt, solvate and/or hydrate. The term "salts" refers to inorganic and organic salts of a compound of the present invention. These salts can be prepared in situ during the final isolation and purification of a compound, or by separately reacting the compound, or prodrug with a suitable organic or inorganic acid or base and isolating the salt thus formed. Representative salts include the hydrobromide, hydrochloride, hydroiodide, sulfate, bisulfate, nitrate, acetate, trifluoroacetate, oxalate, besylate, palmitiate, pamoate, malonate, stearate, laurate, malate, borate, benzoate, lactate, phosphate, hexafluorophosphate, benzene sulfonate, tosylate, formate, citrate, maleate, fumarate, succinate, tartrate, naphthylate, mesylate, glucoheptonate, lactobionate, and laurylsulphonate salts, and the like. These may include cations based on the alkali and alkaline earth metals, such as sodium, lithium, potassium, calcium, magnesium, and the like, as well as non-toxic ammonium, quaternary ammonium, and amine cations including, but not limited to, ammonium, tetramethylammonium, tetraethylammonium, methylamine, dimethylamine, trimethylamine, triethylamine, ethylamine, and the like. See, e.g., Berge, et al., *J. Pharm. Sci.*, 66, 1–19 (1977).

The term "prodrug" means a compound that is transformed in vivo to yield a compound of Formula (I) or a pharmaceutically acceptable salt, hydrate or solvate of the compound. The transformation may occur by various mechanisms, such as through hydrolysis in blood. A discussion of the use of prodrugs is provided by T. Higuchi and W. Stella, "Pro-drugs as Novel Delivery Systems," Vol. 14 of the A.C.S. Symposium Series, and in Bioreversible Carriers in Drug Design, ed. Edward B. Roche, American Pharmaceutical Association and Pergamon Press, 1987.

For example, if a compound of the present invention contains a carboxylic acid functional group, a prodrug can comprise an ester formed by the replacement of the hydrogen atom of the acid group with a group such as $(C_1-C_8)$ alkyl, $(C_2-C_{12})$alkanoyloxymethyl, 1-(alkanoyloxy)ethyl having from 4 to 9 carbon atoms, 1-methyl-1-(alkanoyloxy)-ethyl having from 5 to 10 carbon atoms, alkoxycarbonyloxymethyl having from 3 to 6 carbon atoms, 1-(alkoxycarbonyloxy)ethyl having from 4 to 7 carbon atoms, 1-methyl-1-(alkoxycarbonyloxy)ethyl having from 5 to 8 carbon atoms, N-(alkoxycarbonyl)aminomethyl having from 3 to 9 carbon atoms, 1-(N-(alkoxycarbonyl)amino)ethyl having from 4 to 10 carbon atoms, 3-phthalidyl, 4-crotonolactonyl, gamma-butyrolacton-4-yl, di-N,N-$(C_1-C_2)$alkylamino$(C_2-C_3)$alkyl (such as β-dimethylaminoethyl), carbamoyl-$(C_1-C_2)$alkyl, N,N-di$(C_1-C_2)$alkylcarbamoyl-$(C_1-C_2)$alkyl and piperidino-, pyrrolidino- or morpholino$(C_2-C_3)$alkyl.

Similarly, if a compound of the present invention contains an alcohol functional group, a prodrug can be formed by the replacement of the hydrogen atom of the alcohol group with a group such as $(C_1-C_6)$alkanoyloxymethyl, 1-(($C_1-C_6$) alkanoyloxy)ethyl, 1-methyl-1-(($C_1-C_6$)alkanoyloxy)ethyl, $(C_1-C_6)$alkoxycarbonyloxymethyl, N-$(C_1-C_6)$alkoxycarbonylaminomethyl, succinoyl, $(C_1-C_6)$alkanoyl, α-amino $(C_1-C_4)$alkanoyl, arylacyl and α-aminoacyl, or α-aminoacyl-α-aminoacyl, where each α-aminoacyl group is independently selected from the naturally occurring L-amino acids, P(O)(OH)$_2$, P(O)(O$(C_1-C_6)$alkyl)$_2$ or glycosyl (the radical resulting from the removal of a hydroxyl group of the hemiacetal form of a carbohydrate).

If a compound of the present invention incorporates an amine functional group, a prodrug can be formed by the replacement of a hydrogen atom in the amine group with a group such as R-carbonyl, RO-carbonyl, NRR'-carbonyl where R and R' are each independently $(C_1-C_{10})$alkyl, $(C_3-C_7)$cycloalkyl, benzyl, or R-carbonyl is a natural α-aminoacyl or natural α-aminoacyl-natural α-aminoacyl, —C(OH)C(O)OY' wherein Y' is H, $(C_1-C_6)$alkyl or benzyl, —C(OY$_0$)Y$_1$ wherein Y$_0$ is $(C_1-C_4)$ alkyl and Y$_1$ is $(C_1-C_6)$ alkyl, carboxy$(C_1-C_6)$alkyl, amino$(C_1-C_4)$alkyl or mono-N- or di-N,N-$(C_1-C_6)$alkylaminoalkyl, —C(Y$_2$)Y$_3$ wherein Y$_2$ is H or methyl and Y$_3$ is mono-N- or di-N,N-$(C_1-C_6)$ alkylamino, morpholino, piperidin-1-yl or pyrrolidin-1-yl.

The compounds of the present invention may contain asymmetric or chiral centers, and, therefore, exist in different stereoisomeric forms. It is intended that all stereoisomeric forms of the compounds of the present invention as well as mixtures thereof, including racemic mixtures, form part of the present invention. In addition, the present invention embraces all geometric and positional isomers. For example, if a compound of the present invention incorporates a double bond or a fused ring, both the cis- and trans-forms, as well as mixtures, are embraced within the scope of the invention.

Diastereomeric mixtures can be separated into their individual diastereoisomers on the basis of their physical chemical differences by methods well known to those skilled in the art, such as by chromatography and/or fractional crystallization. Enantiomers can be separated by converting the enantiomeric mixture into a diastereomeric mixture by reaction with an appropriate optically active compound (e.g., chiral auxiliary such as a chiral alcohol or Mosher's acid chloride), separating the diastereoisomers and converting (e.g., hydrolyzing) the individual diastereoisomers to the corresponding pure enantiomers. Also, some of the compounds of the present invention may be atropisomers (e.g., substituted biaryls) and are considered as part of this invention. Enantiomers can also be separated by use of a chiral HPLC column.

The compounds of the present invention may exist in unsolvated as well as solvated forms with pharmaceutically acceptable solvents such as water, ethanol, and the like, and it is intended that the invention embrace both solvated and unsolvated forms.

It is also possible that the intermediates and compounds of the present invention may exist in different tautomeric forms, and all such forms are embraced within the scope of the invention. The term "tautomer" or "tautomeric form" refers to structural isomers of different energies which are interconvertible via a low energy barrier. For example, proton tautomers (also known as prototropic tautomers) include interconversions via migration of a proton, such as keto-enol and imine-enamine isomerizations. A specific example of a proton tautomer is the imidazole moiety where the proton may migrate between the two ring nitrogens. Valence tautomers include interconversions by reorganization of some of the bonding electrons.

The present invention also embraces isotopically-labeled compounds of the present invention which are identical to those recited herein, but for the fact that one or more atoms are replaced by an atom having an atomic mass or mass number different from the atomic mass or mass number usually found in nature. Examples of isotopes that can be incorporated into compounds of the invention include isotopes of hydrogen, carbon, nitrogen, oxygen, phosphorus, sulfur, fluorine, iodine, and chlorine, such as $^2$H, $^3$H, $^{11}$C, $^{13}$C, $^{14}$C, $^{13}$N, $^{15}$N, $^{15}$O, $^{17}$O, $^{18}$O, $^{31}$P, $^{32}$P, $^{35}$S, $^{18}$F, $^{123}$I, $^{125}$I and $^{36}$Cl, respectively.

Certain isotopically-labeled compounds of the present invention (e.g., those labeled with $^3$H and $^{14}$C) are useful in compound and/or substrate tissue distribution assays. Tritiated (i.e., $^3$H) and carbon-14 (i.e., $^{14}$C) isotopes are particularly preferred for their ease of preparation and detectability. Further, substitution with heavier isotopes such as deuterium (i.e., $^2$H) may afford certain therapeutic advantages resulting from greater metabolic stability (e.g., increased in vivo half-life or reduced dosage requirements) and hence may be preferred in some circumstances. Positron emitting isotopes such as $^{15}$O, $^{13}$N, $^{11}$C, and $^{18}$F are useful for positron emission tomography (PET) studies to examine substrate receptor occupancy. Isotopically labeled compounds of the present invention can generally be prepared by following procedures analogous to those disclosed in the Schemes and/or in the Examples herein below, by substituting an isotopically labeled reagent for a non-isotopically labeled reagent.

Compounds of the present invention are useful for treating diseases, conditions and/or disorders modulated by cannabinoid receptor antagonists; therefore, another embodiment of the present invention is a pharmaceutical composition comprising a therapeutically effective amount of a compound of the present invention and a pharmaceutically acceptable excipient, diluent or carrier.

A typical formulation is prepared by mixing a compound of the present invention and a carrier, diluent or excipient. Suitable carriers, diluents and excipients are well known to those skilled in the art and include materials such as carbohydrates, waxes, water soluble and/or swellable polymers, hydrophilic or hydrophobic materials, gelatin, oils, solvents, water, and the like. The particular carrier, diluent or excipient used will depend upon the means and purpose for which the compound of the present invention is being applied. Solvents are generally selected based on solvents recognized by persons skilled in the art as safe (GRAS) to be administered to a mammal. In general, safe solvents are non-toxic aqueous solvents such as water and other non-toxic solvents that are soluble or miscible in water. Suitable aqueous solvents include water, ethanol, propylene glycol, polyethylene glycols (e.g., PEG400, PEG300), etc. and mixtures thereof. The formulations may also include one or more buffers, stabilizing agents, surfactants, wetting agents, lubricating agents, emulsifiers, suspending agents, preservatives, antioxidants, opaquing agents, glidants, processing aids, colorants, sweeteners, perfuming agents, flavoring agents and other known additives to provide an elegant presentation of the drug (i.e., a compound of the present invention or pharmaceutical composition thereof) or aid in the manufacturing of the pharmaceutical product (i.e., medicament).

The formulations may be prepared using conventional dissolution and mixing procedures. For example, the bulk drug substance (i.e., compound of the present invention or stabilized form of the compound (e.g., complex with a cyclodextrin derivative or other known complexation agent)) is dissolved in a suitable solvent in the presence of one or more of the excipients described above. The compound of the present invention is typically formulated into pharmaceutical dosage forms to provide an easily controllable dosage of the drug and to give the patient an elegant and easily handleable product.

The pharmaceutical composition (or formulation) for application may be packaged in a variety of ways depending upon the method used for administering the drug. Generally, an article for distribution includes a container having deposited therein the pharmaceutical formulation in an appropriate form. Suitable containers are well-known to those skilled in the art and include materials such as bottles (plastic and glass), sachets, ampoules, plastic bags, metal cylinders, and the like. The container may also include a tamper-proof assemblage to prevent indiscreet access to the contents of the package. In addition, the container has deposited thereon a label that describes the contents of the container. The label may also include appropriate warnings.

The present invention further provides a method of treating diseases, conditions and/or disorders modulated by cannabinoid receptor antagonists in an animal that includes administering to an animal in need of such treatment a therapeutically effective amount of a compound of the present invention or a pharmaceutical composition comprising an effective amount of a compound of the present invention and a pharmaceutically acceptable excipient, diluent, or carrier. The method is particularly useful for treating diseases, conditions and/or disorders modulated by cannabinoid receptor (in particular, CB1 receptor) antagonists.

Preliminary investigations have indicated that the following diseases, conditions, and/or disorders are modulated by cannabinoid receptor antagonists: eating disorders (e.g., binge eating disorder, anorexia, and bulimia), weight loss or control (e.g., reduction in calorie or food intake, and/or appetite suppression), obesity, depression, atypical depression, bipolar disorders, psychoses, schizophrenia, behavioral addictions, suppression of reward-related behaviors (e.g., conditioned place avoidance, such as suppression of cocaine- and morphine-induced conditioned place preference), substance abuse, addictive disorders, impulsivity, alcoholism (e.g., alcohol abuse, addiction and/or dependence including treatment for abstinence, craving reduction and relapse prevention of alcohol intake), tobacco abuse (e.g., smoking addiction, cessation and/or dependence including treatment for craving reduction and relapse prevention of tobacco smoking), dementia (including memory loss, Alzheimer's disease, dementia of aging, vascular dementia, mild cognitive impairment, age-related cognitive decline, and mild neurocognitive disorder), sexual dysfunction in males (e.g., erectile difficulty), seizure disorders, epilepsy, inflammation, gastrointestinal disorders (e.g., dysfunction of gastrointestinal motility or intestinal propulsion), attention deficit disorder (ADD including attention deficit hyperactivity disorder (ADHD)), Parkinson's disease, and type II diabetes.

Accordingly, the compounds of the present invention described herein are useful in treating diseases, conditions, or disorders that are modulated by cannabinoid receptor antagonists. Consequently, the compounds of the present invention (including the compositions and processes used therein) may be used in the manufacture of a medicament for the therapeutic applications described herein.

Other diseases, conditions and/or disorders for which cannabinoid receptor antagonists may be effective include: premenstrual syndrome or late luteal phase syndrome, migraines, panic disorder, anxiety, post-traumatic syndrome, social phobia, cognitive impairment in non-demented individuals, non-amnestic mild cognitive impairment, post operative cognitive decline, disorders associated with impulsive behaviours (such as, disruptive behaviour disorders (e.g., anxiety/depression, executive function improvement, tic disorders, conduct disorder and/or oppositional defiant disorder), adult personality disorders (e.g., borderline personality disorder and antisocial personality disorder), diseases associated with impulsive behaviours (e.g., substance abuse, paraphilias and self-mutilation), and impulse control disorders (e.g., intermittene explosive disorder, kleptomania, pyromania, pathological gambling, and trichotillomania)), obsessive compulsive disorder, chronic fatigue syndrome, sexual dysfunction in males (e.g., premature ejaculation), sexual dysfunction in females, disorders of sleep (e.g., sleep apnea), autism, mutism, neurodengenerative movement disorders, spinal cord injury, damage of the central nervous system (e.g., trauma), stroke, neurodegenerative diseases or toxic or infective CNS diseases (e.g., encephalitis or meningitis), cardiovascular disorders (e.g., thrombosis), and diabetes.

The compounds of the present invention can be administered to a patient at dosage levels in the range of from about 0.7 mg to about 7,000 mg per day. For a normal adult human having a body weight of about 70 kg, a dosage in the range of from about 0.01 mg to about 100 mg per kilogram body weight is typically sufficient. However, some variability in the general dosage range may be required depending upon the age and weight of the subject being treated, the intended route of administration, the particular compound being administered and the like. The determination of dosage ranges and optimal dosages for a particular patient is well within the ability of one of ordinary skill in the art having the benefit of the instant disclosure. It is also noted that the compounds of the present invention can be used in sustained release, controlled release, and delayed release formulations, which forms are also well known to one of ordinary skill in the art.

The compounds of this invention may also be used in conjunction with other pharmaceutical agents for the treatment of the diseases, conditions and/or disorders described herein. Therefore, methods of treatment that include administering compounds of the present invention in combination with other pharmaceutical agents are also provided. Suitable pharmaceutical agents that may be used in combination with the compounds of the present invention include anti-obesity agents such as apolipoprotein-B secretion/microsomal triglyceride transfer protein (apo-B/MTP) inhibitors, 11β-hydroxy steroid dehydrogenase-1 (11β-HSD type 1) inhibitors, peptide $YY_{3-36}$ or analogs thereof, MCR-4 agonists, cholecystokinin-A (CCK-A) agonists, monoamine reuptake inhibitors (such as sibutramine), sympathomimetic agents, β3 adrenergic receptor agonists, dopamine agonists (such as bromocriptine), melanocyte-stimulating hormone receptor analogs, 5HT2c agonists, melanin concentrating hormone antagonists, leptin (the OB protein), leptin analogs, leptin receptor agonists, galanin antagonists, lipase inhibitors (such as tetrahydrolipstatin, i.e. orlistat), anorectic agents (such as a bombesin agonist), neuropeptide-Y antagonists (e.g., NPY Y5 receptor antagonists, such as the spiro compounds described in U.S. Pat. Nos. 6,566,367; 6,649,624; 6,638,942; 6,605,720; 6,495,559; 6,462,053; 6,388,077; 6,335,345; and 6,326,375; US Publication Nos. 2002/0151456 and 2003/036652; and PCT Publication Nos. WO 03/010175. WO 03/082190 and WO 02/048152), thyromimetic agents, dehydroepiandrosterone or an analog thereof, glucocorticoid receptor agonists or antagonists, orexin receptor antagonists, glucagon-like peptide-1 receptor agonists, ciliary neurotrophic factors (such as Axokine™ available from Regeneron Pharmaceuticals, Inc., Tarrytown, N.Y. and Procter & Gamble Company, Cincinnati, Ohio), human agouti-related proteins (AGRP), ghrelin receptor antagonists, histamine 3 receptor antagonists or inverse agonists, neuromedin U receptor agonists and the like. Other anti-obesity agents, including the preferred agents set forth hereinbelow, are well known, or will be readily apparent in light of the instant disclosure, to one of ordinary skill in the art.

Especially preferred are anti-obesity agents selected from the group consisting of orlistat, sibutramine, bromocriptine, ephedrine, leptin, pseudoephedrine, $PYY_{3-36}$ or an analog thereof, and 2-oxo-N-(5-phenylpyrazinyl)spiro-[isobenzofuran-1(3H), 4'-piperidine]-1'-carboxamide. Preferably, compounds of the present invention and combination therapies are administered in conjunction with exercise and a sensible diet.

Representative anti-obesity agents for use in the combinations, pharmaceutical compositions, and methods of the invention can be prepared using methods known to one of ordinary skill in the art, for example, sibutramine can be prepared as described in U.S. Pat. No. 4,929,629; bromocriptine can be prepared as described in U.S. Pat. Nos. 3,752,814 and 3,752,888; orlistat can be prepared as described in U.S. Pat. Nos. 5,274,143; 5,420,305; 5,540, 917; and 5,643,874; $PYY_{3-36}$ (including analogs) can be prepared as described in US Publication No. 2002/0141985 and WO 03/027637; and the NPY Y5 receptor antagonist 2-oxo-N-(5-phenyl-pyrazinyl)spiro[isobenzofuran-1(3H), 4'-piperidine]-1'-carboxamide can be prepared as described in US Publication No. 2002/0151456. Other useful NPY Y5 receptor antagonists include those described in PCT Publication No. 03/082190, such as 3-oxo-N-(5-phenyl-2-pyrazinyl)-spiro[isobenzofuran-1(3H), 4'-piperidine]-1'-carboxamide; 3-oxo-N-(7-trifluoromethylpyrido[3,2-b]pyridin-2-yl)-spiro-[isobenzofuran-1(3H), 4'-piperidine]-1'-carboxamide; N-[5-(3-fluorophenyl)-2-pyrimidinyl]-3-oxospiro-isobenzofuran-1(3H),[4'-piperidine]-1'-carboxamide; trans-3'-oxo-N-(5-phenyl-2-pyrimidinyl)]spiro[cyclohexane-1,1'(3'H)-isobenzofuran]-4-carboxamide; trans-3'-oxo-N-[1-(3-quinolyl)-4-imidazolyl]spiro[cyclohexane-1,1'(3'H)-isobenzofuran]-4-carboxamide; trans-3-oxo-N-(5-phenyl-2-pyrazinyl)spiro[4-azaiso-benzofuran-1(3H), 1'-cyclohexane]-4'-carboxamide; trans-N-[5-(3-fluorophenyl)-2-pyrimidinyl]-3-oxospiro[5-azaisobenzofuran-1(3H), 1'-cyclohexane]-4'-carboxamide; trans-N-[5-(2-fluorophenyl)-2-pyrimidinyl]-3-oxospiro[5-azaisobenzofuran-1(3H), 1'-cyclohexane]-4'-carboxamide; trans-N-[1-(3,5-difluorophenyl)-4-imidazolyl]-3-oxospiro[7-azaisobenzofuran-1(3H), 1'-cyclohexane]-4'-carboxamide; trans-3-oxo-N-(1-phenyl-4-pyrazolyl)spiro[4-azaisobenzofuran-1(3H), 1'-cyclohexane]-4'-carboxamide; trans-N-[1-(2-fluorophenyl)-3-pyrazolyl]-3-oxospiro[6-azaisobenzofuran-1(3H), 1'-cyclohexane]-4'-carboxamide; trans-3-oxo-N-(1-phenyl-3-pyrazolyl)spiro[6-azaisobenzofuran-1(3H), 1'-cyclohexane]-4'-carboxamide; trans-3-oxo-N-(2-phenyl-1,2,3-triazol-4-yl)spiro[6-azaisobenzofuran-1(3H), 1'-cyclohexane]-4'-carboxamide; and pharmaceutically acceptable salts and esters thereof. All of the above recited U.S. patents and publications are incorporated herein by reference.

Other suitable pharmaceutical agents that may be administered in combination with the compounds of the present invention include agents designed to treat tobacco abuse (e.g., nicotine receptor partial agonists, bupropion hypochloride (also known under the tradename Zyban™) and nicotine replacement therapies), agents to treat erectile dysfunction (e.g., dopaminergic agents, such as apomorphine), ADD/ADHD agents (e.g., Ritalin™, Strattera™, Concerta™ and Adderall™), and agents to treat alcoholism, such as opioid antagonists (e.g., naltrexone (also known under the tradename ReVia™) and nalmefene), disulfiram (also known under the tradename Antabuse™), and acamprosate (also known under the tradename Campral™)). In addition, agents for reducing alcohol withdrawal symptoms may also be co-administered, such as benzodiazepines, beta-blockers, clonidine, carbamazepine, pregabalin, and gabapentin (Neurontin™). Treatment for alcoholism is preferably administered in combination with behavioral therapy including such components as motivational enhancement therapy, cognitive behavioral therapy, and referral to self-help groups, including Alcohol Anonymous (AA).

Other pharmaceutical agents that may be useful include antihypertensive agents; anti-inflammatory agents (e.g., COX-2 inhibitors); antidepressants (e.g., fluoxetine hydrochloride (Prozac™)); cognitive improvement agents (e.g., donepezil hydrochloride (Aircept™) and other acetylcholinesterase inhibitors); neuroprotective agents (e.g., memantine); antipsychotic medications (e.g., ziprasidone (Geodon™), risperidone (Risperdal™), and olanzapine (Zyprexa™)); insulin and insulin analogs (e.g., LysPro insulin); GLP-1 (7-37) (insulinotropin) and GLP-1 (7-36)-$NH_2$; sulfonylureas and analogs thereof: chlorpropamide, glibenclamide, tolbutamide, tolazamide, acetohexamide, Glypizide®, glimepiride, repaglinide, meglitinide; biguanides: metformin, phenformin, buformin; α2-antagonists and imidazolines: midaglizole, isaglidole, deriglidole, idazoxan, efaroxan, fluparoxan; other insulin secretagogues: linogliride, A-4166; glitazones: ciglitazone, Actose® (pioglitazone), englitazone, troglitazone, darglitazone, Avandia®

(BRL49653); fatty acid oxidation inhibitors: clomoxir, etomoxir; α-glucosidase inhibitors: acarbose, miglitol, emiglitate, voglibose, MDL-25,637, camiglibose, MDL-73,945; β-agonists: BRL 35135, BRL 37344, RO 16-8714, ICI D7114, CL 316,243; phosphodiesterase inhibitors: L-386, 398; lipid-lowering agents: benfluorex: fenfluramine; vanadate and vanadium complexes (e.g., Naglivan®) and peroxovanadium complexes; amylin antagonists; glucagon antagonists; gluconeogenesis inhibitors; somatostatin analogs; antilipolytic agents: nicotinic acid, acipimox, WAG 994, pramlintide (Symlin™), AC 2993, nateglinide, aldose reductase inhibitors (e.g., zopolrestat), glycogen phosphorylase inhibitors, sorbitol dehydrogenase inhibitors, sodium-hydrogen exchanger type 1 (NHE-1) inhibitors and/or cholesterol biosynthesis inhibitors or cholesterol absorption inhibitors, especially a HMG-CoA reductase inhibitor, or a HMG-COA synthase inhibitor, or a HMG-CoA reductase or synthase gene expression inhibitor, a CETP inhibitor, a bile acid sequesterant, a fibrate, an ACAT inhibitor, a squalene synthetase inhibitor, an anti-oxidant or niacin. The compounds of the present invention may also be administered in combination with a naturally occurring compound that acts to lower plasma cholesterol levels. Such naturally occurring compounds are commonly called nutraceuticals and include, for example, garlic extract, *Hoodia* plant extracts, and niacin.

The dosage of the additional pharmaceutical agent is generally dependent upon a number of factors including the health of the subject being treated, the extent of treatment desired, the nature and kind of concurrent therapy, if any, and the frequency of treatment and the nature of the effect desired. In general, the dosage range of the additional pharmaceutical agent is in the range of from about 0.001 mg to about 100 mg per kilogram body weight of the individual per day, preferably from about 0.1 mg to about 10 mg per kilogram body weight of the individual per day. However, some variability in the general dosage range may also be required depending upon the age and weight of the subject being treated, the intended route of administration, the particular anti-obesity agent being administered and the like. The determination of dosage ranges and optimal dosages for a particular patient is also well within the ability of one of ordinary skill in the art having the benefit of the instant disclosure.

According to the methods of the invention, a compound of the present invention or a combination of a compound of the present invention and at least one additional pharmaceutical agent is administered to a subject in need of such treatment, preferably in the form of a pharmaceutical composition. In the combination aspect of the invention, the compound of the present invention and at least one other pharmaceutical agent (e.g., anti-obesity agent, nicotine receptor partial agonist, dopaminergic agent, or opioid antagonist) may be administered either separately or in the pharmaceutical composition comprising both. It is generally preferred that such administration be oral. However, if the subject being treated is unable to swallow, or oral administration is otherwise impaired or undesirable, parenteral or transdermal administration may be appropriate.

According to the methods of the invention, when a combination of a compound of the present invention and at least one other pharmaceutical agent are administered together, such administration can be sequential in time or simultaneous with the simultaneous method being generally preferred. For sequential administration, a compound of the present invention and the additional pharmaceutical agent can be administered in any order. It is generally preferred that such administration be oral. It is especially preferred that such administration be oral and simultaneous. When a compound of the present invention and the additional pharmaceutical agent are administered sequentially, the administration of each can be by the same or by different methods.

According to the methods of the invention, a compound of the present invention or a combination of a compound of the present invention and at least one additional pharmaceutical agent (referred to herein as a "combination") is preferably administered in the form of a pharmaceutical composition. Accordingly, a compound of the present invention or a combination can be administered to a patient separately or together in any conventional oral, rectal, transdermal, parenteral, (for example, intravenous, intramuscular, or subcutaneous) intracisternal, intravaginal, intraperitoneal, intravesical, local (for example, powder, ointment or drop), or buccal, or nasal, dosage form.

Compositions suitable for parenteral injection generally include pharmaceutically acceptable sterile aqueous or non-aqueous solutions, dispersions, suspensions, or emulsions, and sterile powders for reconstitution into sterile injectable solutions or dispersions. Suitable aqueous and nonaqueous carriers or diluents (including solvents and vehicles) include water, ethanol, polyols (propylene glycol, polyethylene glycol, glycerol, and the like), suitable mixtures thereof, vegetable oils (such as olive oil) and injectable organic esters such as ethyl oleate. Proper fluidity can be maintained, for example, by the use of a coating such as lecithin, by the maintenance of the required particle size in the case of dispersions, and by the use of surfactants.

These compositions may also contain excipients such as preserving, wetting, emulsifying, and dispersing agents. Prevention of microorganism contamination of the compositions can be accomplished with various antibacterial and antifungal agents, for example, parabens, chlorobutanol, phenol, sorbic acid, and the like. It may also be desirable to include isotonic agents, for example, sugars, sodium chloride, and the like. Prolonged absorption of injectable pharmaceutical compositions can be brought about by the use of agents capable of delaying absorption, for example, aluminum monostearate and gelatin.

Solid dosage forms for oral administration include capsules, tablets, powders, and granules. In such solid dosage forms, a compound of the present invention or a combination is admixed with at least one inert excipient, diluent or carrier. Suitable excipients, diluents or carriers include materials such as sodium citrate or dicalcium phosphate or (a) fillers or extenders (e.g., starches, lactose, sucrose, mannitol, silicic acid and the like); (b) binders (e.g., carboxymethylcellulose, alginates, gelatin, polyvinylpyrrolidone, sucrose, acacia and the like); (c) humectants (e.g., glycerol and the like); (d) disintegrating agents (e.g., agar-agar, calcium carbonate, potato or tapioca starch, alginic acid, certain complex silicates, sodium carbonate and the like); (e) solution retarders (e.g., paraffin and the like); (f) absorption accelerators (e.g., quaternary ammonium compounds and the like); (g) wetting agents (e.g., cetyl alcohol, glycerol monostearate and the like); (h) adsorbents (e.g., kaolin, bentonite and the like); and/or (i) lubricants (e.g., talc, calcium stearate, magnesium stearate, solid polyethylene glycols, sodium lauryl sulfate and the like). In the case of capsules and tablets, the dosage forms may also comprise buffering agents. Solid compositions of a similar type may also be used as fillers in soft or hard filled gelatin capsules using such excipients as lactose or milk sugar, as well as high molecular weight polyethylene glycols, and the like.

Solid dosage forms such as tablets, dragees, capsules, and granules can be prepared with coatings and shells, such as enteric coatings and others well known in the art. They may also contain opacifying agents, and can also be of such composition that they release the compound of the present invention and/or the additional pharmaceutical agent in a delayed manner. Examples of embedding compositions that can be used are polymeric substances and waxes. The drug can also be in micro-encapsulated form, if appropriate, with one or more of the above-mentioned excipients.

Liquid dosage forms for oral administration include pharmaceutically acceptable emulsions, solutions, suspensions, syrups, and elixirs. In addition to the compound of the present invention or the combination, the liquid dosage form may contain inert diluents commonly used in the art, such as water or other solvents, solubilizing agents and emulsifiers, as for example, ethyl alcohol, isopropyl alcohol, ethyl carbonate, ethyl acetate, benzyl alcohol, benzyl benzoate, propylene glycol, 1,3-butylene glycol, dimethylformamide, oils (e.g., cottonseed oil, groundnut oil, corn germ oil, olive oil, castor oil, sesame seed oil and the like), glycerol, tetrahydrofurfuryl alcohol, polyethylene glycols and fatty acid esters of sorbitan, or mixtures of these substances, and the like.

Besides such inert diluents, the composition can also include excipients, such as wetting agents, emulsifying and suspending agents, sweetening, flavoring, and perfuming agents.

Suspensions, in addition to the compound of the present invention or the combination, may further comprise carriers such as suspending agents, e.g., ethoxylated isostearyl alcohols, polyoxyethylene sorbitol and sorbitan esters, microcrystalline cellulose, aluminum metahydroxide, bentonite, agar-agar, and tragacanth, or mixtures of these substances, and the like.

Compositions for rectal or vaginal administration preferably comprise suppositories, which can be prepared by mixing a compound of the present invention or a combination with suitable non-irritating excipients or carriers, such as cocoa butter, polyethylene glycol or a suppository wax which are solid at ordinary room temperature but liquid at body temperature and therefore melt in the rectum or vaginal cavity thereby releasing the active component(s).

Dosage forms for topical administration of the compounds of the present invention and combinations of the compounds of the present invention with anti-obesity agents may comprise ointments, powders, sprays and inhalants. The drugs are admixed under sterile condition with a pharmaceutically acceptable excipient, diluent or carrier, and any preservatives, buffers, or propellants that may be required. Ophthalmic formulations, eye ointments, powders, and solutions are also intended to be included within the scope of the present invention.

The following paragraphs describe exemplary formulations, dosages, etc. useful for non-human animals. The administration of the compounds of the present invention and combinations of the compounds of the present invention with anti-obesity agents can be effected orally or non-orally (e.g., by injection).

An amount of a compound of the present invention or combination of a compound of the present invention with an anti-obesity agent is administered such that an effective dose is received. Generally, a daily dose that is administered orally to an animal is between about 0.01 and about 1,000 mg/kg of body weight, preferably between about 0.01 and about 300 mg/kg of body weight.

Conveniently, a compound of the present invention (or combination) can be carried in the drinking water so that a therapeutic dosage of the compound is ingested with the daily water supply. The compound can be directly metered into drinking water, preferably in the form of a liquid, water-soluble concentrate (such as an aqueous solution of a water-soluble salt).

Conveniently, a compound of the present invention (or combination) can also be added directly to the feed, as such, or in the form of an animal feed supplement, also referred to as a premix or concentrate. A premix or concentrate of the compound in an excipient, diluent or carrier is more commonly employed for the inclusion of the agent in the feed. Suitable carriers are liquid or solid, as desired, such as water, various meals such as alfalfa meal, soybean meal, cottonseed oil meal, linseed oil meal, corncob meal and corn meal, molasses, urea, bone meal, and mineral mixes such as are commonly employed in poultry feeds. A particularly effective carrier is the respective animal feed itself; that is, a small portion of such feed. The carrier facilitates uniform distribution of the compound in the finished feed with which the premix is blended. Preferably, the compound is thoroughly blended into the premix and, subsequently, the feed. In this respect, the compound may be dispersed or dissolved in a suitable oily vehicle such as soybean oil, corn oil, cottonseed oil, and the like, or in a volatile organic solvent and then blended with the carrier. It will be appreciated that the proportions of compound in the concentrate are capable of wide variation since the amount of the compound in the finished feed may be adjusted by blending the appropriate proportion of premix with the feed to obtain a desired level of compound.

High potency concentrates may be blended by the feed manufacturer with proteinaceous carrier such as soybean oil meal and other meals, as described above, to produce concentrated supplements, which are suitable for direct feeding to animals. In such instances, the animals are permitted to consume the usual diet. Alternatively, such concentrated supplements may be added directly to the feed to produce a nutritionally balanced, finished feed containing a therapeutically effective level of a compound of the present invention. The mixtures are thoroughly blended by standard procedures, such as in a twin shell blender, to ensure homogeneity.

If the supplement is used as a top dressing for the feed, it likewise helps to ensure uniformity of distribution of the compound across the top of the dressed feed.

Drinking water and feed effective for increasing lean meat deposition and for improving lean meat to fat ratio are generally prepared by mixing a compound of the present invention with a sufficient amount of animal feed to provide from about $10^{-3}$ to about 500 ppm of the compound in the feed or water.

The preferred medicated swine, cattle, sheep and goat feed generally contain from about 1 to about 400 grams of a compound of the present invention (or combination) per ton of feed, the optimum amount for these animals usually being about 50 to about 300 grams per ton of feed.

The preferred poultry and domestic pet feeds usually contain about 1 to about 400 grams and preferably about 10 to about 400 grams of a compound of the present invention (or combination) per ton of feed.

For parenteral administration in animals, the compounds of the present invention (or combination) may be prepared in the form of a paste or a pellet and administered as an implant, usually under the skin of the head or ear of the animal in which increase in lean meat deposition and improvement in lean meat to fat ratio is sought.

In general, parenteral administration involves injection of a sufficient amount of a compound of the present invention (or combination) to provide the animal with about 0.01 to about 20 mg/kg/day of body weight of the drug. The preferred dosage for poultry, swine, cattle, sheep, goats and domestic pets is in the range of from about 0.05 to about 10 mg/kg/day of body weight of drug.

Paste formulations can be prepared by dispersing the drug in a pharmaceutically acceptable oil such as peanut oil, sesame oil, corn oil or the like.

Pellets containing an effective amount of a compound of the present invention, pharmaceutical composition, or combination can be prepared by admixing a compound of the present invention or combination with a diluent such as carbowax, carnuba wax, and the like, and a lubricant, such as magnesium or calcium stearate, can be added to improve the pelleting process.

It is, of course, recognized that more than one pellet may be administered to an animal to achieve the desired dose level which will provide the increase in lean meat deposition and improvement in lean meat to fat ratio desired. Moreover, implants may also be made periodically during the animal treatment period in order to maintain the proper drug level in the animal's body.

The present invention has several advantageous veterinary features. For the pet owner or veterinarian who wishes to increase leanness and/or trim unwanted fat from pet animals, the instant invention provides the means by which this may be accomplished. For poultry, beef and swine breeders, utilization of the method of the present invention yields leaner animals that command higher sale prices from the meat industry.

Embodiments of the present invention are illustrated by the following Examples. It is to be understood, however, that the embodiments of the invention are not limited to the specific details of these Examples, as other variations thereof will be known, or apparent in light of the instant disclosure, to one of ordinary skill in the art.

EXAMPLES

Unless specified otherwise, starting materials are generally available from commercial sources such as Aldrich Chemicals Co. (Milwaukee, Wis.), Lancaster Synthesis, Inc. (Windham, N.H.), Acros Organics (Fairlawn, N.J.), Maybridge Chemical Company, Ltd. (Cornwall, England), Tyger Scientific (Princeton, N.J.), and AstraZeneca Pharmaceuticals (London, England).

The acronyms listed below have the following corresponding meanings:
LiN(TMS)$_2$—lithium hexamethyldisilazide
PS-DIEA—polystyrene-bound diisopropylethylamine
AIBN—2,2'-azobisisobutyronitrile
HOAt—1-hydroxy-7-azabenzotriazole
EDC—1-(3-dimethylaminopropyl)-3-ethylcarbodiimide hydrochloride General Experimental Procedures NMR spectra were recorded on a Varian Unity™ 400 or 500 (available from Varian Inc., Palo Alto, Calif.) at room temperature at 400 and 500 MHz $^1$H, respectively. Chemical shifts are expressed in parts per million (δ) relative to residual solvent as an internal reference. The peak shapes are denoted as follows: s, singlet; d, doublet; t, triplet; q, quartet; m, multiplet; br s, broad singlet; v br s, very broad singlet; br m, broad multiplet; 2s, two singlets. In some cases only representative $^1$H NMR peaks are given.

Mass spectra were recorded by direct flow analysis using positive and negative atmospheric pressure chemical ionization (APcI) scan modes. A Waters APcI/MS model ZMD mass spectrometer equipped with Gilson 215 liquid handling system was used to carry out the experiments Mass spectrometry analysis was also obtained by RP-HPLC gradient method for chromatographic separation. Molecular weight identification was recorded by positive and negative electrospray ionization (ESI) scan modes. A Waters/Micromass ESI/MS model ZMD or LCZ mass spectrometer equipped with Gilson 215 liquid handling system and HP 1100 DAD was used to carry out the experiments.

Where the intensity of chlorine or bromine-containing ions are described, the expected intensity ratio was observed (approximately 3:1 for $^{35}$Cl/$^{37}$Cl-containing ions and 1:1 for $^{79}$Br/$^{81}$Br-containing ions) and only the lower mass ion is given. MS peaks are reported for all examples.

Optical rotations were determined on a PerkinElmer™ 241 polarimeter (available from PerkinElmer Inc., Wellesley, Mass.) using the sodium D line (λ=589 nm) at the indicated temperature and are reported as follows $[\alpha]_D^{temp}$, concentration (c=g/100 ml), and solvent.

Column chromatography was performed with either Baker™ silica gel (40 μm; J. T. Baker, Phillipsburg, N.J.) or Silica Gel 50 (EM Sciences™, Gibbstown, N.J.) in glass columns or in Biotage™ columns (ISC, Inc., Shelton, Conn.) under low nitrogen pressure. Radial chromatography was performed using a Chromatotron™ (Harrison Research).

Preparation of Key Intermediates

Preparation of Intermediate 1-(2-Chloro-phenyl)-5-hydroxy-1H-pyrazole-3-carboxylic acid ethyl ester (I-1a)

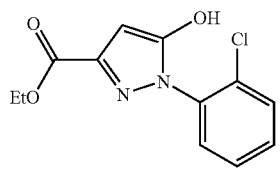

I-1a

To a stirred solution of 2-chlorophenylhydrazine hydrochloride (22.4 g) and potassium carbonate (34.5 g) in ethanol (250 ml) was added diethyl acetylenedicarboxylate (20 ml) and the resulting mixture was heated at reflux for 18 hours. The reaction mixture was cooled, 6 N hydrochloric acid (75 ml) and water (500 ml) were added sequentially. The reaction mixture was extracted with ethyl acetate, the organic layer washed with water, brine, dried (Na$_2$SO$_4$) and concentrated in vacuo. The resulting gum was stirred with isopropyl ether (250 ml) to afford the title compound (I-1a) as a tan solid, (23 g) after filtering and drying in vacuo.

Preparation of Intermediate 5-Bromo-1-(2-chloro-phenyl)-4-formyl-1H-pyrazole-3-carboxylic acid ethyl ester (I-1b)

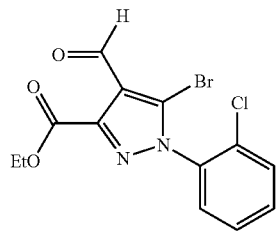

I-1b

To a stirred solution of 1-(2-chloro-phenyl)-5-hydroxy-1H-pyrazole-3-carboxylic acid ethyl ester I-1a (18.2 g) and phosphorus oxybromide (39 g) in 1,2-dichloroethane (200 ml) was added dimethylformamide (10.5 ml) over a 15-min period. The resulting mixture was heated at reflux for 3 hours, cooled, then an additional portion of phosphorus oxybromide (98 g) was added and refluxing was continued for 20 hours. The black reaction mixture was cooled, poured over ice (150 g) and stirred for 30 minutes. The mixture was extracted with dichloromethane (2×), the combined organic layers dried over magnesium sulfate and concentrated in vacuo to afford a dark oil. The oil was passed through a 200 g plug of silica gel, elueting with 30% hexanes:dichloromethane to afford the title compound (I-1b) as a yellow solid, 8.3 g.

Preparation of Intermediate 5-Bromo-1-(2-chloro-phenyl)-4-(isopropylamino-methyl)-1H-pyrazole-3-carboxylic acid ethyl ester (I-1c)

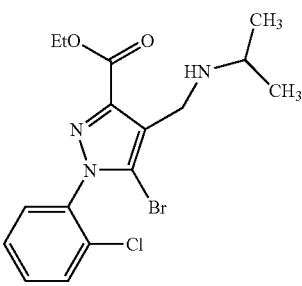

To a stirred solution of 5-bromo-1-(2-chloro-phenyl)-4-formyl-1H-pyrazole-3-carboxylic acid ethyl ester (2 g), isopropylamine (0.95 ml) and acetic acid (0.4 ml) in 1,2-dichloroethane (16 ml) was added sodium triacetoxyborohydride (1.8 g) and the resulting slurry was stirred for 18 hours. The reaction was diluted into ethyl acetate, washed with saturated aqueous sodium bicarbonate, brine, dried (Na$_2$SO$_4$) and concentrated in vacuo to afford the title compound (I-1c) as a golden oil, 2.5 g.

Preparation of Intermediate 3-Bromo-2-(2-chloro-phenyl)-5-isopropyl-4,5-dihydro-2H-pyrrolo[3,4-c]pyrazol-6-one (I-1d)

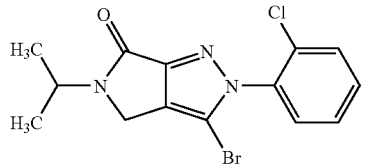

A solution of 5-bromo-1-(2-chloro-phenyl)-4-(isopropylamino-methyl)-1H-pyrazole-3-carboxylic acid ethyl ester (2.2 g) and 1 N aqueous sodium hydroxide (33 ml) in ethanol (55 ml) was heated at 50° C. for 2 hours. The reaction was cooled, acidified to pH~2 with concentrated hydrochloric acid and concentrated to a solid in vacuo. The solids were slurried with ethanol (50 ml), filtered and the filtrate was concentrated in vacuo to afford a white solid, 2.1 g.

To a stirred solution of the above solid (2.0 g), triethylamine (3 ml) in dichloromethane (22 ml) was added 1-propanephosphoric acid cyclic anhydride (5 ml of 50% solution in ethyl acetate) and the resulting solution was stirred for 20 hours. The reaction was diluted in ethyl acetate, washed with 1 N hydrochloride acid, saturated aqueous sodium bicarbonate, brine and dried (Na$_2$SO$_4$) to afford the title compound (I-1d) as a tan solid, 2.0 g.

Preparation of Intermediate 5-(4-Chloro-phenyl)-1-(2-chloro-phenyl)-4-[2-(2-trimethylsilanyl-ethoxy)-vinyl]-1H-pyrazole-3-carboxylic acid ethyl ester (I-3a)

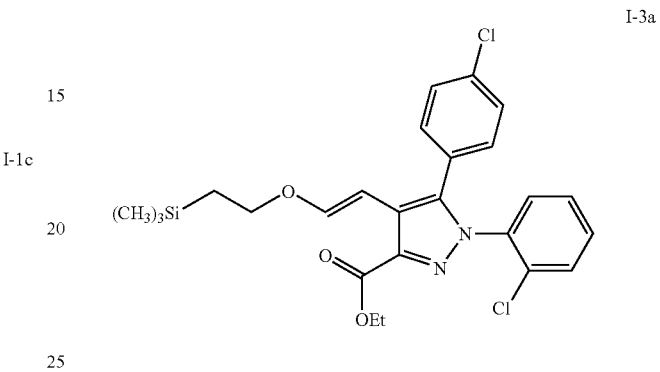

A slurry of sodium hydride (45 mg of 60% in oil) in dimethyl sulfoxide (2 ml) was stirred at 75° C. for 45 minutes, cooled to room temperature, then (2-(trimethylsilyl)-ethoxymethyl)triphenylphosphonium chloride (480 mg) was added in one portion to produce a red solution. After 10 minutes, a solution of 5-(4-chloro-phenyl)-1-(2-chloro-phenyl)-4-formyl-1H-pyrazole-3-carboxylic acid ethyl ester (218 mg) in dimethylsulfoxide (1 ml) was added dropwise and the resulting solution was stirred for 1 hour. Saturated aqueous ammonium chloride was added and the reaction mixture was partitioned between diethyl ether and water. The organic phase was dried (Na$_2$SO$_4$) and concentrated in vacuo to afford a purple oil. Silica gel chromatography (30% ethyl acetate/hexanes) afforded the title compound (I-3a) as a golden oil, 210 mg.

Preparation of Intermediate 5-(4-Chloro-phenyl)-1-(2-chloro-phenyl)-4-(2-oxo-ethyl)-1H-pyrazole-3-carboxylic acid ethyl ester (I-3b)

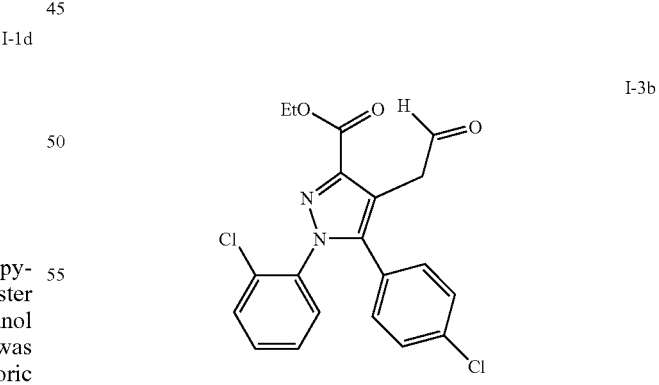

A solution of 5-(4-chloro-phenyl)-1-(2-chloro-phenyl)-4-[2-(2-trimethylsilanyl-ethoxy)-vinyl]-1H-pyrazole-3-carboxylic acid ethyl ester I-3a (210 mg) in 95:5 acetonitrile:conc. hydrofluoric acid (3 ml) was stirred for 2 hours. The reaction was partitioned between saturated aqueous sodium hydrogen carbonate and ethyl acetate. The organic phase was washed with brine, dried (Na$_2$SO$_4$) and concentrated in vacuo to afford the title compound (I-3b), which was taken directly on to the next reaction.

Preparation of Intermediate 1-(2-Chloro-phenyl)-5-(4-chloro-phenyl)-4-methyl-1H-pyrazole-3-carboxylic acid ethyl ester (I-4a)

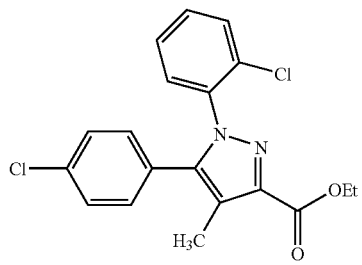

I-4a

A solution of 4-chloropropiophenone (16.9 g, 100 mmol) in diethylether (20 ml) was added to a solution of LiN(TMS)$_2$ (1 M solution in THF, 100 ml, 100 mmol) in diethylether (400 ml) at −78° C. The reaction mixture was stirred at −78 C for 0.75 hour, then diethyl oxalate (15 ml, 110 mmol) was added dropwise. The reaction mixture was slowly allowed to warm to room temperature and stir for 17 hours. The diethyl ether was removed under vacuum and the residue was diluted with diethyl ether. A light yellow solid precipitated out of solution and was collected by filtration (9.9 g, 36%). This solid, which was used without further purification, was dissolved in isopropyl alcohol (200 ml), and 2-chlorophenylhydrazine (5.9 g, 36.1 mmol) and conc. H$_2$SO$_4$ (0.4 ml) was added. The reaction mixture was heated under reflux for 17 hours. After cooling to room temperature, NaHCO$_3$ (1 g) was added. The reaction mixture was concentrated under vacuum. The residue was diluted with EtOAc and the organic solution was washed with sat'd aq NaHCO$_3$ and sat'd aq NaCl, dried, filtered, and concentrated in vacuo. The residue was triturated with cyclohexane to give I-4a as an off-white solid (9.5 g, 25%): +APCI MS (M+1) 375.0.

Preparation of Intermediate 4-Bromomethyl-1-(2-chloro-phenyl)-5-(4-chloro-phenyl)-1H-pyrazole-3-carboxylic acid ethyl ester (I-4b)

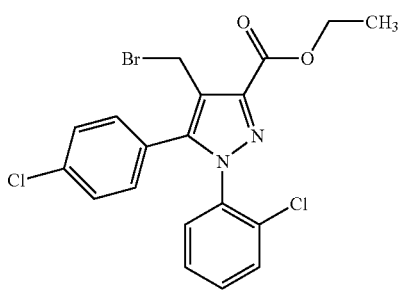

I-4b

A mixture of 1-(2-chloro-phenyl)-5-(4-chloro-phenyl)-4-methyl-1H-pyrazole-3-carboxylic acid ethyl ester I-4a (2.8 g, 7.46 mmol), N-bromosuccinimide (1.6 g, 8.95 mmol), AIBN (245 mg, 1.49 mmol) in CCl$_4$ (60 ml) was heated under reflux for 17 hours. The reaction was cooled to room temperature, filtered to remove any solids, and concentrated under vacuum. The crude residue was purified via silica gel chromatography (Flash 40) using a solvent gradient of 10% EtOAc/hexanes to 20% EtOAc/hexanes to give the desired product (I-4b) as an amorphous solid (2.2 g, 64%): +APCI MS (M+1) 455.0.

Preparation of Intermediate 1-(2-Chloro-phenyl)-5-(4-chloro-phenyl)-4-(isopropylamino-methyl)-1H-pyrazole-3-carboxylic acid ethyl ester (I-4c)

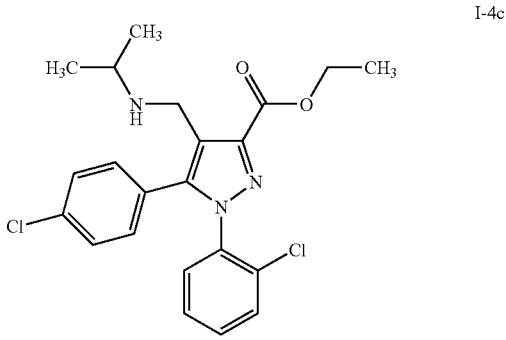

I-4c

A mixture of 4-bromomethyl-1-(2-chloro-phenyl)-5-(4-chloro-phenyl)-1H-pyrazole-3-carboxylic acid ethyl ester I-4b (200 mg, 0.44 mmol), isopropyl amine (26 mg, 0.44 mmol), K$_2$CO$_3$ (182 mg, 1.32 mmol) in CH$_3$CN (5 ml) was stirred for 17 hours at room temperature. The reaction mixture was filtered to remove insoluble material and concentrated under vacuum. The residue was diluted with EtOAc and the organic solution was washed with H$_2$O and sat'd aq. NaCl, dried, and concentrated in vacuo. The crude residue was purified on SiO$_2$-gel chromatography using a solvent gradient of 20% EtOAc/hexanes to 75% EtOAc/hexanes to give the product (I-4c) as an amorphous solid (40 mg, 21%): +APCI MS (M+1) 432.2.

Preparation of Intermediate 1-(2-Chloro-phenyl)-5-(4-chloro-phenyl)-4-(isopropylamino-methyl)-1H-pyrazole-3-carboxylic acid (I-4d)

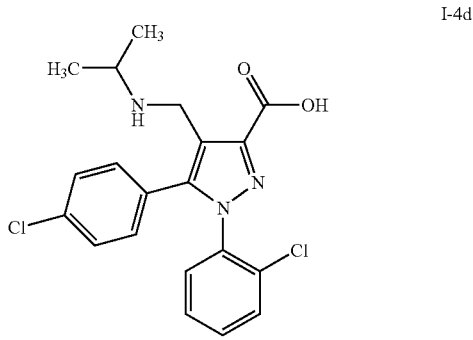

I-4d

A solution of 1-(2-chloro-phenyl)-5-(4-chloro-phenyl)-4-(isopropylamino-methyl)-1H-pyrazole-3-carboxylic acid ethyl ester I-4c (32 mg, 0.074 mmol) in a 1:4 solution of 1 M KOH/EtOH (10 ml) was stirred at 50° C. for 6 hours and at 37° C. for 72 hours. The reaction mixture was treated with conc. HCl until the pH of the solution was approximately 1 and then concentrated in vacuo. The residue was diluted with EtOH and filtered. The filtrate was concentrated under vacuum to give I-4a as a white solid (40 mg, 100%): +APCI MS (M+1) 404.1.

Preparation of Intermediate 2-Chloro-N-(4-chloro-phenyl)-benzamidine (I-5a)

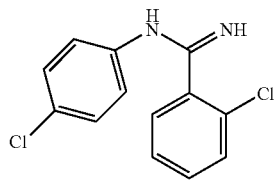

Trimethylaluminum (2 M in hexanes, 100 ml, 200 mmol) was added dropwise to a solution of 4-chloro-phenylamine (18.2 g, 143 mmol) in toluene (550 ml) under a $N_2$ atmosphere at 0° C. The reaction mixture was warmed to room temperature and stirred for 3.5 hours. A solution of 2-chlorobenzonitrile (23.6 g, 171 mmol) in toluene (140 ml) was added and the reaction mixture was heated at 80° C. for 17 hours, during which time it became homogeneous. The reaction mixture was then cooled to room temperature and poured over a slurry of silica gel in $CHCl_3$/methanol (2:1). After filtration, the filter cake was washed with a mixture of $CH_2Cl_2$/MeOH (2:1). The combined filtrates were concentrated in vacuo, and the solid yellow residue was triturated with hexanes/ether (2:1). The product I-5a (25.1 g, 66%) was used in the next reaction without further purification.

Preparation of Intermediate 1-(4-Chloro-phenyl)-2-(2-chloro-phenyl)-4-hydroxy-4,5-dihydro-1H-imidazole-4-carboxylic acid ethyl ester (I-5b)

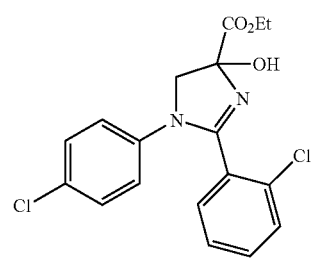

A mixture of 2-chloro-N-(4-chloro-phenyl)-benzamidine (I-5a), 25.1 g, 95 mmol) and $NaHCO_3$ (84 g, 189 mmol) in 2-propanol (473 ml) was treated with 3-bromo-2-oxo-propionic acid ethyl ester (14.3 ml, 22 g, 113 mmol). The reaction mixture was heated at 80° C. for 17 hours. After cooling to room temperature, the solvent was removed in vacuo. The residue was diluted with $CH_2Cl_2$ and the organic solution was washed with $H_2O$, dried over $MgSO_4$, and concentrated in vacuo to provide the product, 1-(4-chloro-phenyl)-2-(2-chloro-phenyl)-4-hydroxy-4,5-dihydro-1H-imidazole-4-carboxylic acid ethyl ester I-5b, as a dark red residue (36 g).

Preparation of 1-(4-Chloro-phenyl)-2-(2-chloro-phenyl)-1H-imidazole-4-carboxylic acid ethyl ester (I-5c)

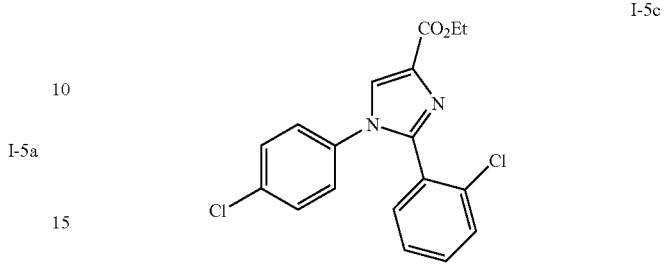

The crude 1-(4-chloro-phenyl)-2-(2-chloro-phenyl)-4-hydroxy-4,5-dihydro-1H-imidazole-4-carboxylic acid ethyl ester (I-5b, 36 g, 94.7 mmol) obtained from the previous step and p-toluenesulfonic acid monohydrate (4.5 g, 24 mmol) in toluene (630 ml) was heated under reflux for 17 hours. The reaction mixture was cooled to room temperature and concentrated in vacuo. The crude residue was taken up in $CH_2Cl_2$ and the organic solution was washed with $H_2O$, sat'd aq. $NaHCO_3$, and sat'd aq $NaCl$, dried over $MgSO_4$ and concentrated in vacuo. The crude residue was purified by plug filtration through silica gel using a gradient of 2% EtOAc/$CH_2Cl_2$ to 10% EtOAc/$CH_2Cl_2$. The fractions containing the product were concentrated, and the oily residue was diluted with 1:3 EtOAc/hexanes (200 ml). After 1 hour, a solid precipitated out of solution and was collected by filtration to provide 1-(4-chloro-phenyl)-2-(2-chloro-phenyl)-1H-imidazole-4-carboxylic acid ethyl ester I-5c (18.63 g, 69.7%).

Preparation of 5-Bromo-1-(4-chloro-phenyl)-2-(2-chloro-phenyl)-1H-imidazole-4-carboxylic acid ethyl ester (I-5d)

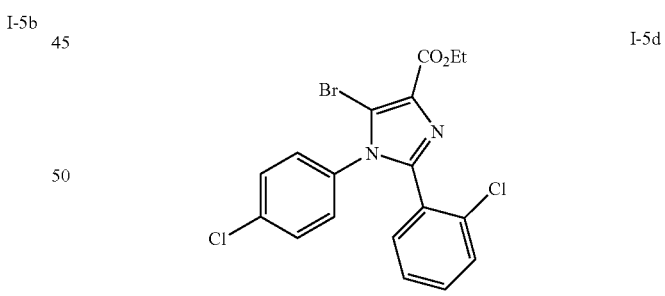

Bromine (3.6 ml, 0.07 mol) was added to a solution of 1-(4-chloro-phenyl)-2-(2-chloro-phenyl)-1H-imidazole-4-carboxylic acid ethyl ester (I-5c, 3.6 g, 0.01 mol) in glacial acetic acid (50 ml) at room temperature. The reaction mixture was stirred for 17 hours, poured over ice-water, and treated with 25% aq. NaOH until the orange solution turned yellow. The aqueous solution was extracted with $CH_2Cl_2$ (3×) and the combined extracts were dried and concentrated in vacuo to give the desired compound I-5d as an oil (4.7 g): +APCI MS (M+1) 441.1; $^1$H NMR ($CD_3Cl$) δ 1.41 (3H, t), 4.43 (2H, q), 7.08–7.12 (2H, m), 7.20–7.40 (7H, m).

Preparation of Intermediate 1-(4-Chloro-phenyl)-2-(2-chloro-phenyl)-5-formyl-1H-imidazole-4-carboxylic acid ethyl ester (I-5e)

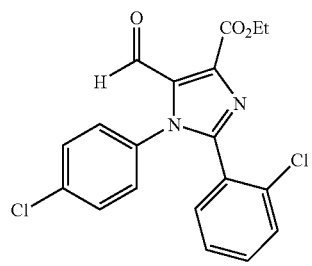

I-5e

To a solution of 5-bromo-1-(4-chloro-phenyl)-2-(2-chloro-phenyl)-1H-imidazole-4-carboxylic acid ethyl ester (I-5d, 4.4 g, 0.01 mmol) in anhydrous THF (100 ml) and under a $N_2$ atmosphere at −78° C. was slowly added tert.-butyl lithium (13 ml of 1.7 M solution in pentane, 0.22 mol). After 1 hour at −78° C., DMF (7.7 ml, 0.1 mmol) was added dropwise. The reaction mixture was stirred at −78° C. for 2.5 hours, quenched with sat'd aq. $NH_4Cl$ (10 ml), allowed to slowly warm to room temperature, and finally poured into sat'd aq. NaCl. The aqueous solution was extracted with $Et_2O$ (3×) and the combined organic extracts were dried ($Na_2SO_4$) and concentrated in vacuo. The crude residue was purified via flash chromatography using a solvent gradient of 1:3 EtOAc/hexanes to 1:1 EtOAc/hexanes to give the desired product I-5e as a pale yellow amorphous glass (2.0 g): +APCI MS (M+1) 389.2; $^1$H NMR ($CD_2Cl_2$) δ 1.41 (3H, t), 4.45 (2H, q), 7.09–7.14 (2H, m), 7.24–7.39 (7H, m), 10.50 (1H, s).

The following two intermediates were prepared using procedures analogous to those described above for the synthesis of 1-(4-chloro-phenyl)-2-(2-chloro-phenyl)-5-formyl-1H-imidazole4-carboxylic acid ethyl ester (I-5e):

2-(4-chloro-phenyl)-1-(2-fluoro-phenyl)-5-formyl-1H-imidazole-4-carboxylic acid ethyl ester (I-5e-2);

2-(4-chloro-phenyl)-1-(2-chloro-phenyl)-5-formyl-1H-imidazole-4-carboxylic acid ethyl ester (I-5e-3).

Preparation of intermediate 2-(4-Chloro-phenyl)-5-cyclopentylaminomethyl-1-(2-fluoro-phenyl)-1H-imidazole-4-carboxylic acid ethyl ester (I-5f)

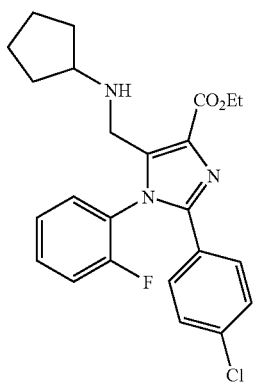

I-5f

A solution of 2-(4-chloro-phenyl)-1-(2-fluoro-phenyl)-5-formyl-1H-imidazole-4-carboxylic acid ethyl ester I-5e-2 (1000 mg, 2.68 mmol), cyclopentylamine (251 mg, 2.95 mmol), $NaBH(OAc)_3$ (796 mg, 3.76 mmol) in dichloroethane was stirred for 17 h at room temperature. The reaction was concentrated in vacuo and the residue was diluted with $CHCl_3$. The organic solution was washed with sat'd aq. $NaHCO_3$ and sat'd aq. NaCl, dried, and concentrated under vacuum. The crude residue was purified on $SiO_2$-gel (Flash 40s) using a solvent gradient of 30% EtOAc/hexanes to 80% EtOAc/hexanes to give the desired product (I-5f) as a yellow oil (680 mg, 57%): +APCI MS (M+1) 442.2.

Preparation of Intermediate 2-(4-Chloro-phenyl)-1-(2-chloro-phenyl)-5-(2-methoxy-vinyl)-1H-imidazole-4-carboxylic acid ethyl ester (I-5g)

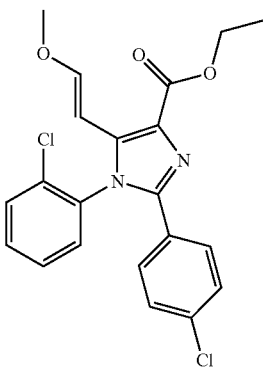

I-5g

To a solution of (methoxymethyl)triphenylphosphonium chloride (533 mg, 1.55 mmol) in THF (10 ml) at 0° C. was added lithium hexamethyldisilazide (1.55 ml, 1M solution, 1.55 mmol). The reaction mixture was stirred for 0.5 h and cooled to −78° C. A solution of 2-(4-chloro-phenyl)-1-(2-chloro-phenyl)-5-formyl-1H-imidazole-4-carboxylic acid ethyl ester I-5e (408 mg, 1.05 mmol) in THF (5 ml) was slowly added via cannula. The reaction mixture was stirred at −78° C. for 5 min, then was allowed to warm to room temperature and stir for 3 hours. The reaction mixture was quenched with $H_2O$ and diluted with EtOAc. The organic solution was separated and the aqueous layer was extracted once with EtOAc. The combined EtOAc extracts were washed with sat'd aq. NaCl, dried, and concentrated in vacuo. The crude residue was purified on 4 mm chromatotron plates using 1:1 EtOAc/hexanes to give the product (I-5g) as two isomeric compounds (148 mg, 34% and 157 mg, 36%): +APCI MS (M+1) 417.2

Preparation of Intermediate 2-(4-Chloro-phenyl)-1-(2-chloro-phenyl)-5-(2-oxo-ethyl)-1H-imidazole-4-carboxylic acid ethyl ester (I-5h)

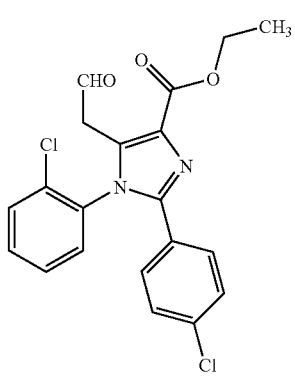

I-5h

A solution of 2-(4-chloro-phenyl)-1-(2-chloro-phenyl)-5-(2-methoxy-vinyl)-1H-imidazole-4-carboxylic acid ethyl ester I-5g (275 mg, 0.659 mmol) and H$_2$SO$_4$ (200 μl) in 5:1 THF/H$_2$O (18 ml) was heated at 70° C. for 3 hours. The reaction mixture was cooled to room temperature and treated with 1M K$_2$CO$_3$ until the pH of the reaction mixture was ~6. The aqueous solution was extracted with CH$_2$Cl$_2$ and the combined organic extracts were washed with sat'd aq. NaCl, dried, and concentrated in vacuo to give a mixture of the starting material and product (I-5h): +APCI MS (M+1) 403.3

Preparation of intermediate 2-(4-Chloro-phenyl)-1-(2-chloro-phenyl)-5-(2-cyclopentylamino-ethyl)-1H-imidazole-4-carboxylic acid ethyl ester (I-5i)

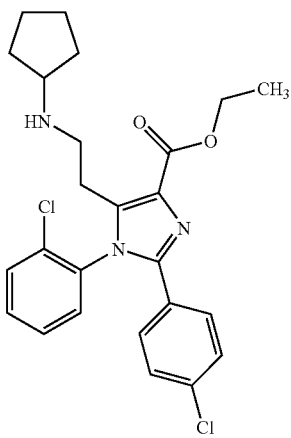

I-5i

Sodium triacetoxyborohydride (32 mg, 0.152 mmol) was added to a solution of 2-(4-chloro-phenyl)-1-(2-chloro-phenyl)-5-(2-oxo-ethyl)-1H-imidazole-4-carboxylic acid ethyl ester I-5h (34 mg, 0.084 mmol), cyclopentylamine (12 μl, 0.118 mmol), and acetic acid (5 μl, 0.09 mmol) in 1,2-dichlorethane (2 ml) at room temperature. The reaction mixture was quenched with 1N NaOH and extracted with CH$_2$Cl$_2$ (3×). The combined CH$_2$Cl$_2$ extracts were washed with sat'd aq NaCl, dried, and concentrated in vacuo. The crude residue was purified on a 1 mm chromatotron plate using 100% EtOAc to give I-5i as a colorless oil (22 mg): +APCI MS (M+1) 472.2.

Preparation of Intermediate 2-(4-Chloro-phenyl)-1-(2-chloro-phenyl)-5-(2-cyclopentylamino-ethyl)-1H-imidazole-4-carboxylic acid (I-5j)

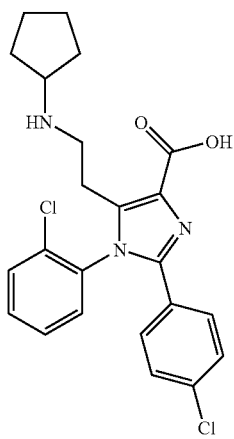

I-5j

To a solution of 2-(4-chloro-phenyl)-1-(2-chloro-phenyl)-5-(2-cyclopentylamino-ethyl)-1H-imidazole-4-carboxylic acid ethyl ester I-5i (22 mg, 0.46 mmol) in absolute EtOH (2 ml) was added 1N KOH (500 μl). The reaction mixture was heated to 85° C. for 4 hours and then was concentrated to a quarter fraction of the original volume. The pH of the solution was adjusted to approximately 3.5 using 10% HCl. The aqueous ethanolic solution was concentrated to dryness to give the I-5j as a solid (20 mg): +APCI MS (M+1) 444.4.

Preparation of Intermediate 2-(4-Chloro-phenyl)-5-cyclopentylaminomethyl-1-(2-fluoro-phenyl)-1H-imidazole-4-carboxylic acid (I-5k)

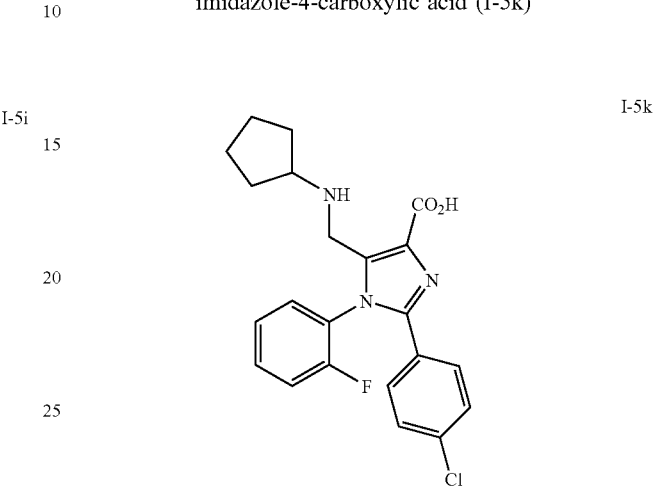

I-5k

A solution of 2-(4-chloro-phenyl)-5-cyclopentylaminomethyl-1-(2-fluoro-phenyl)-1H-imidazole-4-carboxylic acid ethyl ester I-5f (1.2 g, 2.68 mmol) in 1:2 1M KOH/THF was stirred at 55° C. for 17 hours. The reaction mixture was concentrated under vacuum and acidified to pH~1 with concentrated hydrochloric acid. The residue was slurried in EtOH and filtered to remove KCl. The filtrate was concentrated under vaccum to give I-5k as an off-white solid (1.26 g, 97%): +APCI MS (M+1) 414.0.

Example 1 illustrates the preparation of compounds of the present invention where A is nitrogen, B is carbon and X is a bond.

EXAMPLE 1

Preparation of 2-(2-Chloro-phenyl)-5-isopropyl-3-(3,4,5-trifluoro-phenyl)-4,5-dihydro-2H-pyrrolo[3,4-c]pyrazol-6-one (1A-1)

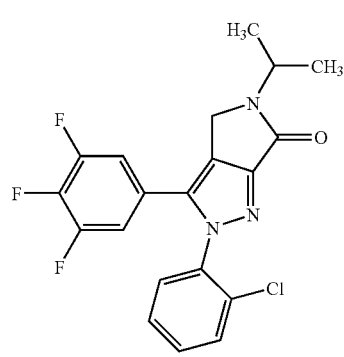

1A-1

A nitrogen-purged solution of 3-bromo-2-(2-chloro-phenyl)-5-isopropyl-4,5-dihydro-2H-pyrrolo[3,4-c]pyrazol-6- one I-1d (100 mg), cesium fluoride (85 mg), 3,4,5-trifluorophenylboronic acid (74 mg) and tetrakis(triphenylphosphine)palladium(0) (32 mg) in 1,2-dimethoxyethane (1 ml) were stirred in a sealed vial at 80° C. for 6 hours. The reaction was cooled and partitioned between ethyl acetate/water, the organic phase was dried (Na$_2$SO$_4$) and concentrated in vacuo to afford an oil. Reverse phase HPLC (gradient of 40% to 100% acetonitrile: 0.01 % aqueous ammonium hydroxide) afforded the title compound (1A-1) as an off-white foam, 19 mg. $^1$H NMR in CDCl$_3$ (ppm): δ 7.6–7.4 (m, 4H), 6.78–6.65 (m, 2H), 4.76–4.64 (m, 1H), 4.40 (br s, 2H), 1.36 (d, 6H); ms (LCMS) m/z =406.3 (M+1)$^+$.

The compounds listed in Table 1 below were prepared using procedures analogous to those described above for the synthesis of Compound 1A-1 using the appropriate starting materials which are available commercially, prepared using preparations well-known to those skilled in the art, or prepared in a manner analogous to routes described above for other intermediates.

TABLE 1

| Ex. No. | R$^0$ | R$^1$ | R$^4$ | LCMS m/z (M + 1)$^+$ |
|---|---|---|---|---|
| 1A-2 | 2-chlorophenyl | 2-chlorophenyl | —CH(CH$_3$)$_2$ | 386.3 |
| 1A-3 | 2-chlorophenyl | 4-(methoxymethyl)phenyl | —CH(CH$_3$)$_2$ | 396.4 |
| 1A-4 | 2-chlorophenyl | 2-fluorophenyl | —CH(CH$_3$)$_2$ | 370.3 |
| 1A-5 | 2-chlorophenyl | 2-methoxy-pyridyl-5-yl | —CH(CH$_3$)$_2$ | 383.4 |
| 1A-6 | 2-chlorophenyl | 3-chloro-4-fluorophenyl | —CH(CH$_3$)$_2$ | 404.2 |
| 1A-7 | 2-chlorophenyl | 4-fluoro-3-methylphenyl | —CH(CH$_3$)$_2$ | 384.3 |
| 1A-8 | 2-chlorophenyl | vinyl | —CH(CH$_3$)$_2$ | 302.3 |
| 1A-9 | 2-chlorophenyl | 4-(trifluoromethyl)phenyl | 2,2,2-trifluoroethyl | 460.4 |
| 1A-10 | 2-chlorophenyl | 4-(trifluoromethyl)phenyl | isopropyl | 420.4 |
| 1A-11 | 2-chlorophenyl | 4-chlorophenyl | ethyl | 372.4 |
| 1A-12 | 2-chlorophenyl | 2-chlorophenyl | isopropyl | 386.3 |
| 1A-13 | 2-chlorophenyl | 4-(methoxymethyl)phenyl | isopropyl | 396.4 |
| 1A-14 | 2-chlorophenyl | 2-fluorophenyl | isopropyl | 370.3 |
| 1A-15 | 2-chlorophenyl | 4-chlorophenyl | 2-fluoroethyl | 390.3 |
| 1A-16 | 2-chlorophenyl | 4-chlorophenyl | 2,2-difluoroethyl | 408.1 |
| 1A-17 | 2-chlorophenyl | 4-chlorophenyl | 2,2,2-trifluoroethyl | 426.3 |
| 1A-18 | 2-chlorophenyl | 4-ethoxyphenyl | t-butyl | 410.4 |
| 1A-19 | 2-chlorophenyl | 4-ethoxyphenyl | i-butyl | 410.4 |
| 1A-20 | 2-chlorophenyl | 4-ethoxyphenyl | ethyl | 382.4 |
| 1A-21 | 2-chlorophenyl | 4-ethoxyphenyl | isopropyl | 396.4 |
| 1A-22 | 2-chlorophenyl | 4-ethoxyphenyl | 2,2,2-trifluoroethyl | 436.4 |
| 1A-23 | 2-chlorophenyl | 4-ethylphenyl | t-butyl | 394.5 |
| 1A-24 | 2-chlorophenyl | 4-ethylphenyl | i-butyl | 394.5 |
| 1A-25 | 2-chlorophenyl | 4-ethylphenyl | ethyl | 366.4 |
| 1A-26 | 2-chlorophenyl | 4-ethylphenyl | isopropyl | 380.4 |
| 1A-27 | 2-chlorophenyl | 4-ethylphenyl | 2,2,2-trifluoroethyl | 420.4 |
| 1A-28 | 2-chlorophenyl | 4-ethylphenyl | 2,2-difluoropropyl | 416.5 |
| 1A-29 | 2-chlorophenyl | 4-isopropoxyphenyl | t-butyl | 424.3 |
| 1A-30 | 2-chlorophenyl | 4-isopropoxyphenyl | i-butyl | 424.3 |
| 1A-31 | 2-chlorophenyl | 4-isopropoxyphenyl | ethyl | 396.2 |
| 1A-32 | 2-chlorophenyl | 4-isopropoxyphenyl | isopropyl | 410.2 |
| 1A-33 | 2-chlorophenyl | 4-isopropoxyphenyl | 2,2,2-trifluoroethyl | 450.2 |
| 1A-34 | 2-chlorophenyl | 4-isopropoxyphenyl | 2,2-difluoropropyl | 446.3 |
| 1A-35 | 2-chlorophenyl | 4-t-butylphenyl | 2,2,2-trifluoroethyl | 448.5 |

TABLE 1-continued

| Ex. No. | R⁰ | R¹ | R⁴ | LCMS m/z (M + 1)⁺ |
|---|---|---|---|---|
| 1A-36 | 2-chlorophenyl | 4-t-butylphenyl | 2,2-difluoropropyl | 444.5 |
| 1A-37 | 2-chlorophenyl | 4-i-propylphenyl | 2,2,2-trifluoroethyl | 434.5 |
| 1A-38 | 2-chlorophenyl | 4-i-propylphenyl | 2,2-difluoropropyl | 430.5 |

Preparation of 2-(2-Chloro-phenyl)-3-[2-(4-chloro-phenyl)-vinyl]-5-isopropyl-4,5-dihydro-2H-pyrrolo[3,4-c]pyrazol-6-one (1A-39)

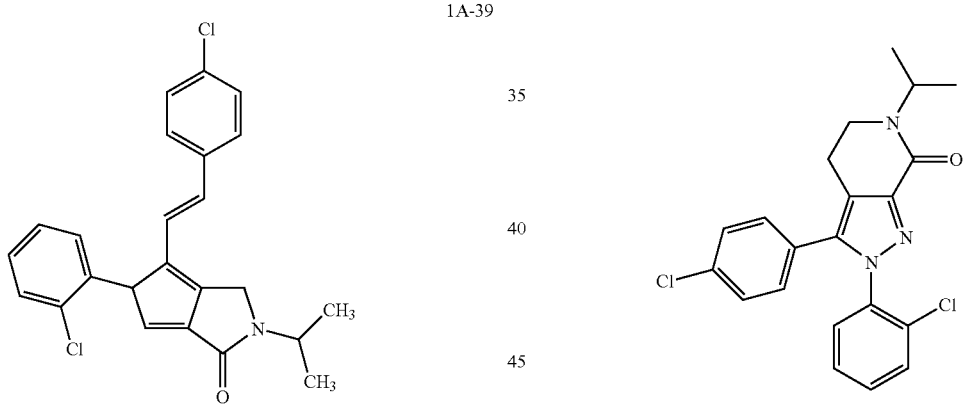

To a stirred solution of 2-(2-chloro-phenyl)-5-isopropyl-3-vinyl-4,5-dihydro-2H-pyrrolo[3,4-c]pyrazol-6-one 1A-8 (42 mg), palladium acetate (3 mg) and 4-chloroiodobenzene (300 mg) were stirred for 18 hours. The reaction was concentrated and chromatographed on silica gel (gradient 30% to 60% ethyl acetate/hexanes) to afford the title compound (1A-39), 44 mg. ¹H NMR in d₆-DMSO (ppm): δ 7.78 (d, 1H), 7.63–7.38 (m, 5H), 7.13 (d, 1H), 6.61 (d, 1H), 4.62 (s, 2H), 4.40 (m, 1H), 1.23 (d, 6H); ms (LCMS) m/z=412.3 (M+1)⁺.

Example 2 illustrates the preparation of compounds of the present invention where A is nitrogen, B is carbon and X is —C(R²ᵃ)(R²ᵇ)—.

EXAMPLE 2

Preparation of 3-(4-chloro-phenyl)-2-(2-chloro-phenyl)-6-isopropyl-2,4,5,6-tetrahydro-pyrazolo [3,4-c] pyridin-7-one (2A-1)

To a stirred solution of I-3b (157 mg), isopropylamine (66 μl), acetic acid (27 μl) in 1,2-dichloroethane (0.5 ml) was added sodium triacetoxyborohydride (124 mg). After 1.5 hours, the reaction was diluted into ethyl acetate, washed with saturated aqueous sodium bicarbonate, brine, dried (Na₂SO₄), and concentrated in vacuo to afford a golden foam, which was taken onto the next step without further purification.

The product of the above step and 1 N aqueous sodium hydroxide (2.5 ml) were heated at 50° C. for 2.5 hours. The reaction solution was cooled, acidified to pH~2 with concentrated hydrochloric acid, and concentrated in vacuo. The resulting solid residue was slurried with ethanol (10 ml), filtered, the solids were washed with ethanol, and the combined filtrates concentrated in vacuo to afford a white solid, which was taken on to the next step without further purification.

To a stirred solution of the above solid prepared in the above step, triethylamine (0.2 ml) in dichloromethane (3 ml) was added 1-propane-phosphoric acid cyclic anhydride (0.34 ml of 50% solution in ethyl acetate) and the resulting solution was stirred for 2 hours. The reaction mixture was diluted with ethyl acetate, washed with 1 N hydrochloric acid, saturated aqueous sodium bicarbonate, brine, and dried ($Na_2SO_4$) to afford a golden oil. Silica gel chromatography (60% ethyl acetate/hexanes) afforded the title compound (2A-1) as a white solid, 103 mg. $^1$H NMR in $CDCl_3$ (ppm): δ 7.50–7.23 (m, 6H), 7.03 (d, 2H), 5.17 (m, 1H), 3.57 (m, 2H), 2.84 (br s, 2H), 1.20 (d, 6H); ms (LCMS) m/z=400.3 $(M+1)^+$.

The compounds listed in Table 2 below were prepared using procedures analogous to those described above for the synthesis of Compound 2A-1 using the appropriate starting materials which are available commercially, prepared using preparations well-known to those skilled in the art, or prepared in a manner analogous to routes described above for other intermediates.

TABLE 2

| Ex. No. | $R^0$ | $R^1$ | $R^4$ | LCMS m/z $(M + 1)^+$ |
|---|---|---|---|---|
| 2A-2 | 2-chlorophenyl | 4-chlorophenyl | 2,2,2-trifluoroethyl | 440.2 |
| 2A-3 | 2-chlorophenyl | 4-chlorophenyl | 2,2-difluoroethyl | 422.3 |
| 2A-4 | 2-chlorophenyl | 4-chlorophenyl | 2-fluoroethyl | 404.3 |
| 2A-5 | 2-chlorophenyl | 4-(trifluoromethyl)phenyl | isopropyl | 434.4 |
| 2A-6 | 2-chlorophenyl | 4-chlorophenyl | ethyl | 386.4 |
| 2A-7 | 2-chlorophenyl | 4-chlorophenyl |  | 426.4 |
| 2A-8 | 2-chlorophenyl | 4-chlorophenyl | 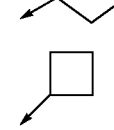 | 412.4 |
| 2A-9 | 2-chlorophenyl | 4-chlorophenyl | t-butyl | 414.4 |
| 2A-10 | 2-chlorophenyl | 4-chlorophenyl | i-butyl | 414.4 |
| 2A-11 | 2-chlorophenyl | 4-chlorophenyl | 2,2-difluoropropyl | 436.3 |
| 2A-12 | 2-chlorophenyl | 4-chlorophenyl | 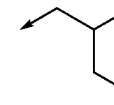 | 454.5 |
| 2A-13 | 2-chlorophenyl | 4-chlorophenyl | 2-methoxy-2-methylpropyl | 444.4 |
| 2A-14 | 2-chlorophenyl | 4-ethylphenyl | 2,2-difluoropropyl | 430.5 |
| 2A-15 | 2-chlorophenyl | 4-ethylphenyl | isopropyl | 394.5 |
| 2A-16 | 2-chlorophenyl | 4-ethylphenyl | t-butyl | 408.5 |
| 2A-17 | 2-chlorophenyl | 4-ethylphenyl | i-butyl | 408.4 |
| 2A-18 | 2-chlorophenyl | 4-ethylphenyl | 2,2,2-trifluoroethyl | 434.4 |
| 2A-19 | 2-chlorophenyl | 4-ethylphenyl | ethyl | 380.4 |
| 2A-20 | 2-chlorophenyl | 4-isopropylphenyl | 2,2-difluoropropyl | 444.5 |
| 2A-21 | 2-chlorophenyl | 4-isopropylphenyl | 2,2,2-trifluoroethyl | 448.5 |
| 2A-22 | 2-methylphenyl | 4-chlorophenyl | 2,2,2-trifluoroethyl | 420.4 |
| 2A-23 | 2-methylphenyl | 4-chlorophenyl | 2,2-difluoropropyl | 416.4 |

EXAMPLE 3

Preparation of 3-(4-Chloro-phenyl)-2-(2-chloro-phenyl)-5-isopropyl-4,5-dihydro-2H-pyrrolo[3,4-c]pyrazol-6-one (3A-1)

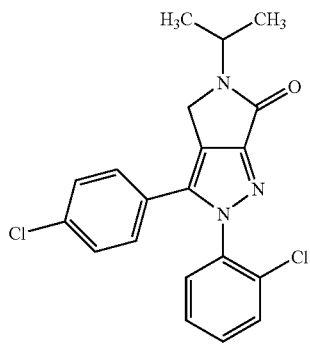

3A-1

A mixture of 1-(2-chloro-phenyl)-5-(4-chloro-phenyl)-4-(isopropylamino-methyl)-1H-pyrazole-3-carboxylic acid I4d (40 mg, 0.074 mmol), EDC (28 mg, 0.148 mmol), HOAt (20 mg, 0.148 mmol), and triethylamine (0.02 ml, 0.148 mmol) in $CH_2Cl_2$ (10 ml) was stirred at room temperature for 17 hours. The reaction mixture was washed with sat'd aq $NaHCO_3$, sat'd aq NaCl, dried and concentrated in vacuo. The crude residue was diluted with cyclohexane and stirred for 17 hours. A solid precipitated out of solution and was collected by filtration to give 3A-1 (11 mg, 38%): +APCI MS (M+1) 386.1; $^1$H NMR ($CDCl_3$) δ 7.50–7.38 (m, 4H), 7.26 (d, 2H, J=9.6 Hz), 7.06 (d, 2H), 4.69 (m, 1H), 1.3 (d, 6H, J=6.65 Hz).

The compounds listed in Table 3 below were prepared using procedures analogous to those described above for the synthesis of Compound 3A-1 using the appropriate starting materials which are available commercially, prepared using preparations well-known to those skilled in the art, or prepared in a manner analogous to routes described above for other intermediates.

TABLE 3

| Ex. No. | $R^0$ | $R^1$ | $R^{3a}$ | $R^{3b}$ | $R^4$ | +APCI MS (M + 1) |
|---|---|---|---|---|---|---|
| 3A-2 | 2-chloro-phenyl | 4-methoxy-phenyl | H | H | cyclopentyl | 408.2 |
| 3A-3 | 2-chloro-phenyl | 4-methoxy-phenyl | H | H | cyclohexyl | 422.4 |
| 3A-4 | 2-chloro-phenyl | 4-chloro-phenyl | H | H | tert-butyl | 400.0 |
| 3A-5 | 2-chloro-phenyl | 4-chloro-phenyl | H | H | cyclobutyl | 398.2 |
| 3A-6 | 2-chloro-phenyl | 4-chloro-phenyl | H | H | cyclopentyl | 412.3 |
| 3A-7 | 2,4-dichloro-phenyl | 4-chloro-phenyl | H | H | isopropyl | 420.0 |
| 3A-8 | 2,4-dichloro-phenyl | 4-chloro-phenyl | H | H | tert-butyl | 434.1 |

TABLE 3-continued

| Ex. No. | R⁰ | R¹ | R³ᵃ | R³ᵇ | R⁴ | +APCI MS (M + 1) |
|---|---|---|---|---|---|---|
| 3A-9 | 4-chloro-phenyl | 2-chloro-phenyl | H | H |  | 386.1 |
| 3A-10 | 4-chloro-phenyl | 2-chloro-phenyl | H | H |  | 412.4 |
| 3A-11 | 4-chloro-phenyl | 2-chloro-phenyl | H | H |  | 426.4 |
| 3A-12 | 4-chloro-phenyl | 2-chloro-phenyl | H | H |  | 438.1 |
| 3A-13 | 4-chloro-phenyl | 2-fluoro-phenyl | H | H |  | 396.4 |
| 3A-14 | 4-chloro-phenyl | 2-fluoro-phenyl | H | H | 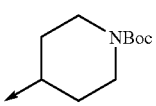 | 410.5 |
| 3A-15 | 4-chloro-phenyl | 2-chloro-phenyl | H | H | 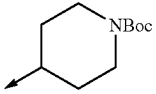 | 427.3 |
| 3A-16 | 2-chloro-phenyl | 4-chloro-phenyl | H | H | 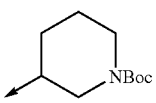 | 427.3 (M + 1 − Boc) |
| 3A-17 | 4-chloro-phenyl | 2-chloro-phenyl | H | H | 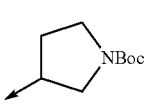 | 527.1 |
| 3A-18 | 4-chloro-phenyl | 2-chloro-phenyl | H | H |  | 513.1 |

Example 4 illustrates the preparation of compounds of the present invention where A is carbon, B is nitrogen (imidazole derivatives), and X is a bond.

EXAMPLE 4

Preparation of 2-(4-Chloro-phenyl)-5-cyclopentyl-1-(2-fluoro-phenyl)-5 6-dihydro-1H-pyrrolo[3,4-d]imidazol-4-one (4A-1)

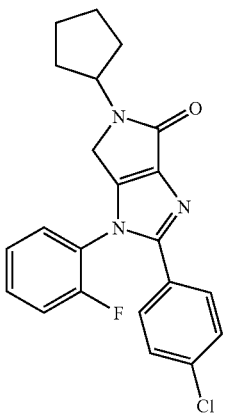

4A-1

A mixture of 2-(4-chloro-phenyl)-5-cyclopentylaminomethyl-1-(2-fluoro-phenyl)-1H-imidazole-4-carboxylic acid I-5k (1.2 g, 2.59 mmol), EDC (994 mg, 5.18 mmol), HOAt (704 mg, 5.18 mmol), and triethylamine (1.1 ml, 7.76 mmol) in $CH_2Cl_2$ (200 ml) was stirred for 17 hours at room temperature. The reaction mixture was washed with sat'd aq $NaHCO_3$ and sat'd aq. NaCl, dried and concentrated in vacuo. The crude residue was purified on $SiO_2$-gel using a solvent gradient of 30% EtOAc/hexanes to 60% EtOAc/hexanes to give 4A-1 as a white solid (752 mg, 73%): +APCI MS (M+1) 396.2; $^1$H NMR ($CDCl_3$): δ 7.61–7.59 (m, 2H), 7.42–7.37 (m, 6H), 4.60 (m, 1H), 4.50 (s, 2H), 2.0 (m, 2H), 1.8–1.65 (m, 6H).

The compounds listed in Table 4 below were prepared using procedures analogous to those described above for the synthesis of Compound 4A-1 using the appropriate starting materials which are available commercially, prepared using preparations well-known to those skilled in the art, or prepared in a manner analogous to routes described above for other intermediates. The compounds listed below were isolated initially as their free base and then converted to its corresponding hydrochloride salt prior to in vivo testing (if tested in vivo).

TABLE 4

| Ex. No. | $R^0$ | $R^1$ | R | +ES MS (M + 1) |
|---|---|---|---|---|
| 4A-2 | 4-chlorophenyl | 2,4-dichlorophenyl | cyclopentyl | 446.0 |
| 4A-3 | 4-chlorophenyl | 2,4-dichlorophenyl | cyclohexyl | 460.0 |
| 4A-4 | 4-chlorophenyl | 2,4-dichlorophenyl | —$CH_2CF_3$ | 460.0 |
| 4A-5 | 4-chlorophenyl | 2-chlorophenyl | isopropyl | 386.3 |
| 4A-6 | 4-chlorophenyl | 2-chlorophenyl | cyclopentyl | 412.2 |
| 4A-7 | 4-chlorophenyl | 2-chlorophenyl | cyclohexyl | 426.0 |
| 4A-8 | 4-chlorophenyl | 2-fluorophenyl | cyclohexyl | 410.2 |
| 4A-9 | 4-chlorophenyl | 2-fluorophenyl | cyclohexylmethyl | 424.3 |
| 4A-10 | 4-fluorophenyl | 2-fluorophenyl | cyclopentyl | 380.2 |
| 4A-11 | 4-fluorophenyl | 2-chlorophenyl | cyclopentyl | 396.2 |
| 4A-12 | 2-chlorophenyl | 4-chlorophenyl | cyclopentyl | 412.2 |
| 4A-13 | 2-chlorophenyl | 4-chlorophenyl | cyclohexyl | 426.2 |
| 4A-14 | 2,4-dichlorophenyl | 4-chlorophenyl | cyclohexyl | 460.2 |

Example 5 illustrates the preparation of compounds of the present invention where A is carbon, B is nitrogen, and X is —C($R^{2a}$)($R^{2b}$)—.

EXAMPLE 5

Preparation of 2-(4-Chloro-phenyl)-1-(2-chloro-phenyl)-5-cyclopentyl-1,5,6,7-tetrahydro-imidazo[4,5-c]pyridin-4-one (5A-1)

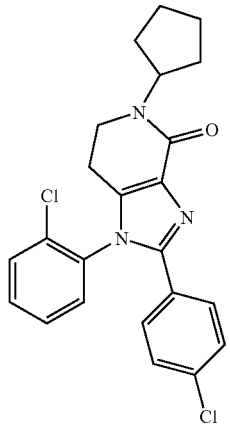

5A-1

A mixture of 2-(4-chloro-phenyl)-1-(2-chloro-phenyl)-5-(2-cyclopentylamino-ethyl-1H-imidazole-4-carboxylic acid I-5j (20 mg, 0.046 mmol), EDC (19 mg, 0.1 mmol), HOAt (13 mg, 0.1 mmol), and triethylamine (14 μl, 0.1 mmol) in 1,2-dichloroethane (20 ml) was stirred for 17 hours at room temperature. The reaction mixture was washed with sat'd aq NaHCO$_3$ and the aqueous bicarbonate solution was back extracted once with CH$_2$Cl$_2$. The combined CH$_2$Cl$_2$ extracts were dried and concentrated in vacuo. The residue was dissolved in diethyl ether (1 ml) and several drops of 4M HCl in dioxane were added. The organic solution was decanted and additional ether was added. The mixture was stirred for several minutes and the solvent decanted again. The residue was dried under vacuum to give the desired produce 5A-1 as a colorless solid: +APCI MS (M+1) 426.3; $^1$H NMR (CDCl$_3$): δ 7.62–7.57 (m, 1H), 7.53–7.47 (m, 1H), 7.44–7.39 (m, 1H), 7.37–7.33 (m, 2H), 7.32–7.28 (m, 1H), 7.24–7.19 (m, 2H), 5.16–5.06 (m,1H), 3.56–3.50 (m, 2H), 3.26–3.17 (m, 2H), 2.71–2.56 (m, 2H), 1.92–1.83 (m, 2H), 1.76–1.46 (m, 4H).

Example 6 illustrates the preparation of compounds of the present invention where A is nitrogen, B is carbon, X is a bond, and R$^{3a}$, R$^{3b}$ are hydrogen, alkyl, and arylalkyl.

EXAMPLE 6

Preparation of 3-(4-Chloro-phenyl)-2-(2-chloro-phenyl)-5-isopropyl-4-methyl-4,5-dihydro-2H-pyrrolo[3,4-c]pyrazol-6-one (6A-1)

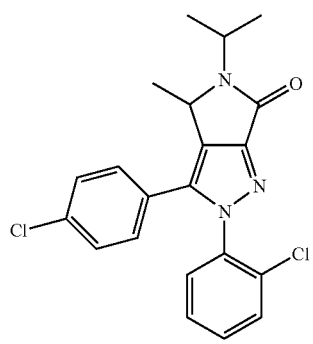

6A-1

To a solution of 3-(4-chloro-phenyl)-2-(2-chloro-phenyl)-5-isopropyl-4,5-dihydro-2H-pyrrolo[3,4-c]pyrazol-6-one 3A-1 (19 mg, 0.05 mmol) in THF (0.5 ml) at −78° C. was added LiHMDSi (55 μl, 0.055 mmol). A deep blue-black solution was formed. The reaction mixture was stirred for 0.17 hour and then iodomethane (4.4 μl, 0.07 mmol) was added dropwise. The reaction mixture was stirred at −78° C. for 0.25 h (until a yellow color formed) and at room temperature for 2 hours, quenched with sat'd aq NH$_4$Cl, and extracted with EtOAc. The organic solution was washed with sat'd aq NaCl, dried, and concentrated in vacuo. The residue was purified on 1 mm chromatotron plates using a 1:1 EtOAc/hexane solution to give 6A-1 as a white solid (3.2 mg, 14%); +ES MS (M+1) 400.3; $^1$H NMR (CDCl$_3$): δ 7.4–7.3 (m, 4H), 7.28–7.24 (m, 2H), 7.1-7.06 (m, 2H), 4.84–4.77 (m, 1H), 4.37–4.27 (m, 1H), 1.48–1.4 (m, 9H).

The compounds in Table 6 below were prepared using procedures analogous to those described above for the synthesis of Compound 6A-1 using the appropriate starting materials which are available commercially, prepared using preparations well-known to those skilled in the art, or prepared in a manner analogous to routes described above for other intermediates.

TABLE 6

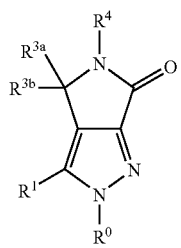

| Ex. No. | R$^0$ | R$^1$ | R$^{3a}$ | R$^{3b}$ | R$^4$ | +ES MS (M + H) |
|---|---|---|---|---|---|---|
| 6A-2 | 2-chloro-phenyl | 4-chloro-phenyl | benzyl | H | isopropyl | 476.3 |

TABLE 6-continued

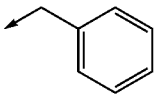

| Ex. No. | R⁰ | R¹ | R³ᵃ | R³ᵇ | R⁴ | +ES MS (M + H) |
|---|---|---|---|---|---|---|
| 6A-3 | 2-chloro-phenyl | 4-chloro-phenyl | 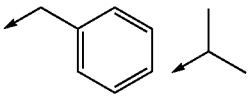 |  | | 566.4 |

Example 7 illustrates the preparation of compounds of the present invention where A is nitrogen, B is carbon, X is a bond, and R⁴ is pyrrolidin-3-yl, piperidin-3-yl, piperidin-4-yl.

EXAMPLE 7

Preparation of 3-(4-Chloro-phenyl)-2-(2-chloro-phenyl)-5-(1-isopropyl-piperidin-4-yl)-4,5-dihydro-2H-pyrrolo[3,4-c]pyrazol-6-one (7A-1)

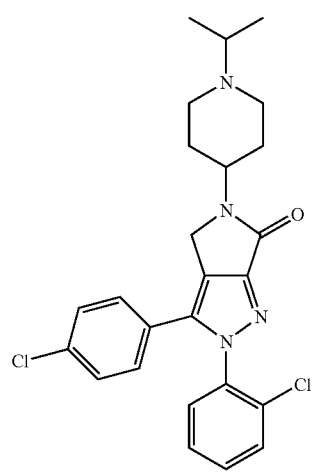

7A-1

A solution of 4-[3-(4-chloro-phenyl)-2-(2-chloro-phenyl)-6-oxo-2,6-dihydro4H-pyrrolo[3,4-c]pyrazol-5-yl]-piperidine-1-carboxylic acid tert-butyl ester 3A-17 (80 mg, 0.152 mmol) in 1:5 conc HCl/EtOH (6 ml) was stirred at room temperature for 2 hours. The reaction mixture was concentrated in vacuo to give a white solid.

A mixture of the product obtained from the preceding step (30 mg, 0.065 mmol), 2-bromopropane (24 mg, 0.194 mmol), K₂CO₃ (45 mg, 0.323 mmol) in DMF (2 ml) was stirred at room temperature for 17 hours. The reaction mixture was diluted with EtOAc and washed with H₂O and sat'd aq NaCl, dried, and concentrated in vacuo. The crude residue was azeotroped once with heptane to remove any DMF and purified via SiO₂-gel chromatography using 5% Et₂NH/EtOAc to give an oil. ¹H NMR (CDCl₃): δ 7.62–7.45 (m, 4H), 7.39–7.32 (d, 2H), 7.23–7.2 (d, 2H), 4.60 (s, 2H), 4.18 (m, 1H), 3.10–3.03 (m, 1H), 1.96–1.90 (m, 4H), 1.30–1.25 (m, 4H), 1.09–1.07 (d, 6H).

The product from the above reaction was stirred in 4M HCl/dioxane (1 mL) for 0.25 hour and concentrated under vacuum to give 7A-1 as an amorphous solid (2 mg, 6%).

The compounds in Table 7 below were prepared using procedures analogous to those described above for the synthesis of Compound 7A-1 using the appropriate starting materials which are available commercially, prepared using preparations well-known to those skilled in the art, or prepared in a manner analogous to routes described above for other intermediates. The compounds listed below were generally isolated as the free base and then converted to their corresponding hydrochloride salts prior to in vivo testing (if tested in vivo).

TABLE 7

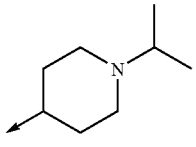

| Ex. No. | R⁰ | R¹ | R³ᵃ | R³ᵇ | R⁴ | +ES MS (M + H) |
|---|---|---|---|---|---|---|
| 7A-2 | 4-chloro-phenyl | 2-chloro-phenyl | H | H | 1-isopropyl-piperidin-4-yl | 469.2 |
| 7A-3 | 4-chloro-phenyl | 2-chloro-phenyl | H | H | 1-ethyl-piperidin-4-yl | 455.2 |
| 7A-4 | 4-chloro-phenyl | 2-chloro-phenyl | H | H | 1-isopropyl-piperidin-3-yl | 469.1 |
| 7A-5 | 4-chloro-phenyl | 2-chloro-phenyl | H | H | 1-ethyl-piperidin-3-yl | 455.1 |
| 7A-6 | 4-chloro-phenyl | 2-chloro-phenyl | H | H | 1-isopropyl-pyrrolidin-3-yl | 455.3 |

Example 8 illustrates the preparation of compounds of the present invention having Formula (II) or (IV).

EXAMPLE 8

Preparation of 3-(4-chloro-phenyl)-2-(2-chloro-phenyl)-5-isopropyl-2,4,5,6-tetrahydro-pyrrolo[3,4-c]pyrazole (8A-1)

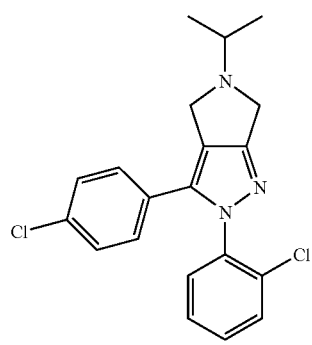

8A-1

A solution of 3-(4-chloro-phenyl)-2-(2-chloro-phenyl)-5-isopropyl-4,5-dihydro-2H-pyrrolo[3,4-c]pyrazol-6-one 3A-1 (7 mg, 0.018 mmol) and BH₃THF (166 ml, 166 mmol) was stirred at room temperature for 1 hour and at 50° C. for 17 hours. After the reaction mixture was cooled to room temperature, MeOH (5 ml) was added. The reaction mixture was heated under reflux for 2 h, cooled to room temperature, and concentrated in vacuo. The residue was diluted with 4 M HCl/dioxanes (1 ml) and concentrated under vacuum. The residue was dissolved in CH₂Cl₂ and hexanes were added to precipitate 8A-1 as a colorless solid (2 mg, 27%): +APCI MS (M+H) 372.5; ¹H NMR (CD₃OD): δ 7.59–7.43 (m, 4H), 7.38 (d, 2H), 7.20 (d, 2H), 4.80–4.65 (m, 2H), 3.91–3.82 (m, 1H), 3.68–3.55 (m, 2H), 1.52 (d, 6H).

The compounds in Table 8 below were prepared using procedures analogous to those described above for the synthesis of Compound 8A-1 using the appropriate starting materials which are available commercially, prepared using preparations well-known to those skilled in the art, or prepared in a manner analogous to routes described above for other intermediates. The compounds listed below were generally isolated as the free base and then converted to their corresponding hydrochloride salts prior to in vivo testing (if tested in vivo).

TABLE 8

| Ex. No. | R⁰ | R¹ | R⁴ | MS (MH)⁺ |
|---|---|---|---|---|
| 8A-2 | 4-chlorophenyl | 2-fluorophenyl | cyclohexyl | 396.5 |
| 8A-3 | 2,4-dichlorophenyl | 4-chlorophenyl | cyclopentyl | 434.4 |

Pharmacological Testing

The utility of the compounds of the present invention in the practice of the instant invention can be evidenced by activity in at least one of the protocols described hereinbelow. The following acronyms are used in the protocols described below.

BSA—bovine serum albumin
DMSO—dimethylsulfoxide
EDTA—ethylenediamine tetracetic acid
PBS—phosphate-buffered saline
EGTA—ethylene glycol-bis(β-aminoethyl ether) N,N,N',N'-tetraacetic acid
GDP—guanosine diphosphate
sc—subcutaneous
po—orally
ip—intraperitoneal
icv—intra cerebro ventricular
iv—intravenous

[³H]SR141716A—radiolabeled N-(piperidin-1-yl)-5-(4-chlorophenyl)-1-(2,4-dichlorophenyl)-4-methyl-1H-pyrazole-3-carboxamide hydrochloride available from Amersham Biosciences, Piscataway, N.J.

[³H]CP-55940—radiolabled 5-(1,1-dimethylheptyl)-2-[5-hydroxy-2-(3-hydroxypropyl-cyclohexyl]-phenol available from NEN Life Science Products, Boston, Mass.

AM251—N-(piperidin-1-yl)-1-(2,4-dichlorophenyl)-5-(4-iodophenyl)-4-methyl-1H-pyrazole-3-carboxamide available from Tocris™, Ellisville, Mo.

All of the compounds listed in the Example section above were tested in the CB-1 receptor binding assay below. The compounds provided a range of binding activities from 0.6 nM-2500 nM.

Those compounds having an activity <20 nM were then tested in the CB-1 GTPγ [³⁵S] Binding Assay and the CB-2 binding assay described below in the Biological Binding Assays section. Selected compounds were then tested in vivo using one or more of the functional assays described in the Biological Functional Assays section below.

In Vitro Biological Assays

Bioassay systems for determining the CB-1 and CB-2 binding properties and pharmacological activity of cannabinoid receptor ligands are described by Roger G. Pertwee in "Pharmacology of Cannabinoid Receptor Ligands" Current Medicinal Chemistry, 6, 635–664 (1999) and in WO 92/02640 (U.S. application Ser. No. 07/564,075 filed Aug. 8, 1990, incorporated herein by reference).

The following assays were designed to detect compounds that inhibit the binding of [³H] SR141716A (selective radiolabeled CB-1 ligand) and [³H] 5-(1,1-dimethylheptyl)-2-[5-hydroxy-2-(3-hydroxypropyl)-cyclohexyl]-phenol; radiolabeled CB-1/CB-2 ligand) to their respective receptors.

Rat CB-1 Receptor Binding Protocol

PelFreeze brains (available from Pel Freeze Biologicals, Rogers, Ark.) were cut up and placed in tissue preparation buffer (5 mM Tris HCl, pH=7.4 and 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 nM Tris, pH=7.4, 5 mM $MgCl_2$, and 1 mM EDTA) per brain used. A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [³H] SR141716A was diluted in a ligand buffer (0.5% BSA plus TME) and 25 μl were added to the plate. A BCA protein assay was used to determine the appropriate tissue concentration and then 200 μl of rat brain tissue at the appropriate concentration was added to the plate. The plates were covered and placed in an incubator at 20° C. for 60 minutes. At the end of the incubation period 250 μl of stop buffer (5% BSA plus TME) was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

Human CB-1 Receptor Binding Protocol

Human embryonic kidney 293 (HEK 293) cells transfected with the CB-1 receptor cDNA (obtained from Dr. Debra Kendall, University of Connecticut) were harvested in homogenization buffer (10 mM EDTA, 10 mM EGTA, 10 mM Na Bicarbonate, protease inhibitors; pH=7.4), and homogenized with a Dounce Homogenizer. The homogenate was then spun at 1,000×g for 5 minutes at 4° C. The supernatant was recovered and centrifuged at 25,000×G for 20 minutes at 4° C. The pellet was then re-suspended in 10 ml of homogenization buffer and re-spun at 25,000×G for 20 minutes at 4° C. The final pellet was re-suspended in 1 ml of TME (25 mM Tris buffer (pH=7.4) containing 5 mM $MgCl_2$ and 1 mM EDTA). A protein assay was performed and 200 μl of tissue totaling 20 μg was added to the assay.

The test compounds were diluted in drug buffer (0.5% BSA, 10% DMSO and TME) and then 25 μl were added to a deep well polypropylene plate. [³H] SR141716A was diluted in a ligand buffer (0.5% BSA plus TME) and 25 μl were added to the plate. The plates were covered and placed in an incubator at 30° C. for 60 minutes. At the end of the incubation period 250 μl of stop buffer (5% BSA plus TME)

was added to the reaction plate. The plates were then harvested by Skatron onto GF/B filtermats presoaked in BSA (5 mg/ml) plus TME. Each filter was washed twice. The filters were dried overnight. In the morning the filters were counted on a Wallac Betaplate™ counter (available from PerkinElmer Life Sciences™, Boston, Mass.).

CB-2 Receptor Binding Protocol

Chinese hamster ovary-K1 (CHO-K1) cells transfected with CB-2 cDNA (obtained from Dr. Debra Kendall, University of Connecticut) were harvested in tissue preparation buffer (5 mM Tris-HCl buffer (pH=7.4) containing 2 mM EDTA), polytroned at high speed and kept on ice for 15 minutes. The homogenate was then spun at 1,000×g for 5 minutes at 4° C. The supernatant was recovered and centrifuged at 100,000×G for 1 hour at 4° C. The pellet was then re-suspended in 25 ml of TME (25 mM Tris buffer (pH=7.4) containing 5 mM $MgCl_2$ and 1 mM EDTA) per brain used. A protein assay was performed and 200 μl of tissue totaling 10 μg was added to the assay.

The test compounds were diluted in drug buffer (0.5% BSA, 10% DMSO, and 80.5% TME) and then 25 μl were added to the deep well polypropylene plate. [$^3$H] 5-(1,1-Dimethyl-heptyl)-2-[5-hydroxy-2-(3-hydroxy-propyl)-cyclohexyl]-phenol was diluted a ligand buffer (0.5% BSA and 99.5% TME) and then 25 μl were added to each well at a concentration of 1 nM. A BCA protein assay was used to determine the appropriate tissue concentration and 200 μl of the tissue at the appropriate concentration was added to the plate. The plates were covered and placed in an incubator at 30° C. for 60 minutes. At the end of the incubation period 250 μl of stop buffer (5% BSA plus TME) was added to the reaction plate. The plates were then harvested by Skatron format onto GF/B filtermats presoaked in BSA (5 mg/ml) plus TME. Each filter was washed twice. The filters were dried overnight. The filters were then counted on the Wallac Betaplate™ counter.

CB-1 GTPγ [$^{35}$S]Binding Assay

Membranes were prepared from CHO-K1 cells stably transfected with the human CB-1 receptor cDNA. Membranes were prepared from cells as described by Bass et al, in "Identification and characterization of novel somatostatin antagonists," *Molecular Pharmacology*, 50, 709–715 (1996). GTPγ [$^{35}$S] binding assays were performed in a 96 well FlashPlate™ format in duplicate using 100 μM GTPγ [$^{35}$S] and 10 μg membrane per well in assay buffer composed of 50 mM Tris HCl, pH 7.4, 3 mM $MgCl_2$, pH 7.4, 10 mM $MgCl_2$, 20 mM EGTA, 100 mM NaCl, 30 μM GDP, 0.1 % bovine serum albumin and the following protease inhibitors: 100 μg/ml bacitracin, 100 μg/ml benzamidine, 5 μg/ml aprotinin, 5 μg/ml leupeptin. The assay mix was then incubated with increasing concentrations of antagonist ($10^{-10}$ M to $10^{-5}$ M) for 10 minutes and challenged with the cannabinoid agonist 5-(1,1-dimethyl-heptyl)-2-[5-hydroxy-2-(3-hydroxy-propyl)-cyclohexyl]-phenol (10 μM). Assays were performed at 30° C. for one hour. The FlashPlates™ were then centrifuged at 2000×g for 10 minutes. Stimulation of GTPγ[$^{35}$S] binding was then quantified using a Wallac Microbeta. $EC_{50}$ calculations done using Prism™ by Graphpad.

Inverse agonism was measured in the absense of agonist.

CB-1 FLIPR-based Functional Assay Protocol

CHO-K1 cells co-transfected with the human CB-1 receptor cDNA (obtained from Dr. Debra Kendall, University of Connecticut) and the promiscuous G-protein G16 were used for this assay. Cells were plated 48 hours in advance at 12500 cells per well on collagen coated 384 well black clear assay plates. Cells were incubated for one hour with 4 μM Fluo-4 AM (Molecular Probes) in DMEM (Gibco) containing 2.5 mM probenicid and pluronic acid (0.04%). The plates were then washed 3 times with HEPES-buffered saline (containing probenicid; 2.5 mM) to remove excess dye. After 20 min the plates were added to the FLIPR individually and fluorescence levels was continuously monitored over an 80 s period. Compound additions were made simultaneously to all 384 wells after 20 s of baseline. Assays were performed in triplicate and 6 point concentration-response curves generated. Antagonist compounds were subsequently challenged with 3 μM WIN 55,212-2 (agonist). Data were analyzed using Graph Pad Prism.

Detection of Inverse Agonists

The following cyclic-AMP assay protocol using intact cells was used to determine inverse agonist activity.

Cells were plated into a 96-well plate at a plating density of 10,000–14,000 cells per well at a concentration of 100 μl per well. The plates were incubated for 24 hours in a 37° C. incubator. The media was removed and media lacking serum (100 μl) was added. The plates were then incubated for 18 hours at 37° C.

Serum free medium containing 1 mM IBMX was added to each well followed by 10 μl of test compound (1:10 stock solution (25 mM compound in DMSO) into 50% DMSO/PBS) diluted 10× in PBS with 0.1 % BSA. After incubating for 20 minutes at 37° C., 2 μM of Forskolin was added and then incubated for an additional 20 minutes at 37° C. The media was removed, 100 μl of 0.01N HCl was added and then incubated for 20 minutes at room temperature. Cell lysate (75 μl) along with 25 μl of assay buffer (supplied in FlashPlate™ cAMP assay kit available from NEN Life Science Products Boston, Mass.) into a Flashplate. cAMP standards and cAMP tracer were added following the kit's protocol. The flashplate was then incubated for 18 hours at 4° C. The content of the wells were aspirated and counted in a Scintillation counter.

In Vivo Biological Assays

Cannabinoid agoinists such as $\Delta^9$-tetrahydrocannabinol ($\Delta^9$-THC) and 5-(1,1-dimethyl-heptyl)-2-[5-hydroxy-2-(3-hydroxy-propyl)-cyclohexyl]-phenol have been shown to affect four characteristic behaviors in mice, collectively known as the Tetrad. For a description of these behaviors see: Smith, P. B., et al. in "The pharmacological activity of anandamide, a putative endogenous cannabinoid, in mice." *J. Pharmacol. Exp. Ther.*, 270(1), 219–227 (1994) and Wiley, J., et al. in "Discriminative stimulus effects of anandamide in rats," *Eur. J. Pharmacol.*, 276(1–2), 49–54 (1995). Reversal of these activities in the Locomotor Activity, Catalepsy, Hypothermia, and Hot Plate assays described below provides a screen for in vivo activity of CB-1 antagonists.

All data is presented as % reversal from agonist alone using the following formula: (5-(1,1-dimethyl-heptyl)-2-[5-hydroxy-2-(3-hydroxy-propyl)-cyclohexyl]-phenol/agonist-vehicle/agonist)/(vehicle/veicle-vehicle/agonist). Negative numbers indicate a potentiation of the agonist activity or non-antagonist activity. Positive numbers indicate a reversal of activity for that particular test.

Locomotor Activity

Male ICR mice (n=6) (17–19 g, Charles River Laboratories, Inc., Wilmington, Mass.) were pre-treated with test compound (sc, po, ip, or icv). Fifteen minutes later, the mice were challenged with 5-(1,1-dimethyl-heptyl)-2-[5-hydroxy-2-(3-hydroxy-propyl)-cyclohexyl]-phenol (sc). Twenty-five minutes after the agonist injection, the mice were placed in clear acrylic cages (431.8 cm×20.9 cm×20.3 cm) containing clean wood shavings. The subjects were allowed to explore surroundings for a total of about 5 minutes and the activity was recorded by infrared motion detectors (available from Coulbourn Instruments™, Allentown, Pa.) that were placed on top of the cages. The data was computer collected and expressed as "movement units."

Catalepsy

Male ICR mice (n=6)(17–19 g upon arrival) were pre-treated with test compound (sc, po, ip or icv). Fifteen minutes later, the mice were challenged with 5-(1,1-dimethyl-heptyl)-2-[5-hydroxy-2-(3-hydroxy-propyl)-cyclohexyl]-phenol (sc). Ninety minutes post injection, the mice were placed on a 6.5 cm steel ring attached to a ring stand at a height of about 12 inches. The ring was mounted in a horizontal orientation and the mouse was suspended in the gap of the ring with fore- and hind-paws gripping the perimeter. The duration that the mouse remained completely motionless (except for respiratory movements) was recorded over a 3-minute period.

The data were presented as a percent immobility rating. The rating was calculated by dividing the number of seconds the mouse remains motionless by the total time of the observation period and multiplying the result by 100. A percent reversal from the agonist was then calculated.

Hypothermia

Male ICR mice (n=5) (17–19 g upon arrival) were pre-treated with test compounds (sc, po, ip or icv). Fifteen minutes later, mice were challenged with the cannabinoid agonist 5-(1,1-dimethyl-heptyl)-2-[5-hydroxy-2-(3-hydroxy-propyl)-cyclohexyl]-phenol (sc). Sixty-five minutes post agonist injection, rectal body temperatures were taken. This was done by inserting a small thermostat probe approximately 2–2.5 cm into the rectum. Temperatures were recorded to the nearest tenth of a degree

Hot Plate

Male ICR mice (n=7) (17–19 g upon arrival) are pre-treated with test compounds (sc, po, ip or iv). Fifteen minutes later, mice were challenged with a cannabinoid agonist 5-(1,1-dimethyl-heptyl)-2-[5-hydroxy-2-(3-hydroxy-propyl)-cyclohexyl]-phenol (sc). Forty-five minutes later, each mouse was tested for reversal of analgesia using a standard hot plate meter (Columbus Instruments). The hot plate was 10"×10"×0.75" with a surrounding clear acrylic wall. Latency to kick, lick or flick hindpaw or jump from the platform was recorded to the nearest tenth of a second. The timer was experimenter activated and each test had a 40 second cut off. Data were presented as a percent reversal of the agonist induced analgesia.

Food Intake

The following screen was used to evaluate the efficacy of test compounds for inhibiting food intake in Sprague-Dawley rats after an overnight fast.

Male Sprague-Dawley rats were obtained from Charles River Laboratories, Inc. (Wilmington, Mass.). The rats were individually housed and fed powdered chow. They were maintained on a 12 hour light/dark cycle and received food and water ad libitum. The animals were acclimated to the vivarium for a period of one week before testing was conducted. Testing was completed during the light portion of the cycle.

To conduct the food intake efficacy screen, rats were transferred to individual test cages without food the afternoon prior to testing, and the rats were fasted overnight. After the overnight fast, rats were dosed the following morning with vehicle or test compounds. A known antagonist was dosed (3 mg/kg) as a positive control, and a control group received vehicle alone (no compound). The test compounds were dosed at ranges between 0.1 and 100 mg/kg depending upon the compound. The standard vehicle was 0.5% (w/v) methylcellulose in water and the standard route of administration was oral. However, different vehicles and routes of administration were used to accommodate various compounds when required. Food was provided to the rats 30 minutes after dosing and the Oxymax automated food intake system (Columbus Instruments, Columbus, Ohio) was started. Individual rat food intake was recorded continuously at 10-minute intervals for a period of two hours. When required, food intake was recorded manually using an electronic scale; food was weighed every 30 minutes after food was provided up to four hours after food was provided. Compound efficacy was determined by comparing the food intake pattern of compound-treated rats to vehicle and the standard positive control.

Alcohol Intake

The following protocol evaluates the effects of alcohol intake in alcohol preferring (P) female rats (bred at Indiana University) with an extensive drinking history. The following references provide detailed descriptions of P rats: Li ,T.-K., et al., "Indiana selection studies on alcohol related behaviors" in *Development of Animal Models as Pharmacogenetic Tools* (eds McClearn C. E., Deitrich R. A. and Erwin V. G.), Research Monograph 6, 171–192 (1981) NIAAA, ADAMHA, Rockville, Md.; Lumeng, L, et al., "New strains of rats with alcohol preference and nonpreference" *Alcohol And Aldehyde Metabolizing Systems*, 3, Academic Press, N.Y., 537–544 (1977); and Lumeng, L, et al., "Different sensitivities to ethanol in alcohol-preferring and -nonpreferring rats," *Pharmacol, Biochem Behav.*, 16, 125–130 (1982).

Female rats were given 2 hours of access to alcohol (10% v/v and water, 2-bottle choice) daily at the onset of the dark cycle. The rats were maintained on a reverse cycle to facilitate experimenter interactions. The animals were initially assigned to four groups equated for alcohol intakes: Group 1—vehicle (n =8); Group 2—positive control (e.g. 5.6 mg/kg AM251; n =8); Group 3—low dose test compound (n =8); and Group 4—high dose of test compound (n =8). Test compounds were generally mixed into a vehicle of 30% (w/v) β-cyclodextrin in distilled water at a volume of 1–2 ml/kg. Vehicle injections were given to all groups for the first two days of the experiment. This was followed by 2 days of drug injections (to the appropriate groups) and a final day of vehicle injections. On the drug injection days, drugs were given sc 30 minutes prior to a 2-hour alcohol access period. Alcohol intake for all animals was measured during the test period and a comparison was made between drug and vehicle-treated animals to determine effects of the compounds on alcohol drinking behavior.

Additional drinking studies were done utilizing female C57BI/6 mice (Charles River). Several studies have shown that this strain of mice will readily consume alcohol with little to no manipulation required (Middaugh et al., "Ethanol Consumption by C57BL/6 Mice: Influence of Gender and Procedural Variables" *Alcohol*, 17 (3), 175–183, 1999; Le et al., "Alcohol Consumption by C57BL/6, BALA/c, and DBA/2 Mice in a Limited Access Paradigm" *Pharmacology Biochemistry and Behavior*, 47, 375–378, 1994).

For our purposes, upon arrival (17–19 g) mice were individually housed and given unlimited access to powdered rat chow, water and a 10% (w/v) alcohol solution. After 2–3 weeks of unlimited access, water was restricted for 20 hours and alcohol was restricted to only 2 hours access daily. This was done in a manner that the access period was the last 2 hours of the dark part of the light cycle.

Once drinking behavior stabilized, testing commenced. Mice were considered stable when the average alcohol consumption for 3 days was ±20% of the average for all 3 days. Day 1 of test consisted of all mice receiving vehicle injection (sc or ip). Thirty to 120 minutes post injection access was given to alcohol and water. Alcohol consumption for that day was calculated (g/kg) and groups were assigned (n=7–10) so that all groups had equivocal alcohol intake. On day 2 and 3, mice were injected with vehicle or drug and the same protocol as the previous day was followed. Day 4 was wash out and no injections were given. Data was analyzed using repeated measures ANOVA. Change in water or alcohol consumption was compared back to vehicle for each day of the test. Positive results would be interpreted as a compound that was able to significantly reduce alcohol consumption while having no effect on water Oxygen Consumption Methods:

Whole body oxygen consumption is measured using an indirect calorimeter (Oxymax from Columbus Instruments, Columbus, Ohio) in male Sprague Dawley rats (if another rat strain or female rats are used, it will be specified). Rats (300–380 g body weight) are placed in the calorimeter chambers and the chambers are placed in activity monitors. These studies are done during the light cycle. Prior to the measurement of oxygen consumption, the rats are fed standard chow ad libitum. During the measurement of oxygen consumption, food is not available. Basal pre-dose oxygen consumption and ambulatory activity are measured every 10 minutes for 2.5 to 3 hours. At the end of the basal pre-dosing period, the chambers are opened and the animals are administered a single dose of compound (the usual dose range is 0.001 to 10 mg/kg) by oral gavage (or other route of administration as specified, i.e. s.c., i.p., i.v.). Drugs are prepared in methylcellulose, water or other specified vehicle (examples include PEG400, 30% beta-cyclo dextran and propylene glycol). Oxygen consumption and ambulatory activity are measured every 10 minutes for an additional 1–6 hours post-dosing.

The Oxymax calorimeter software calculates the oxygen consumption (ml/kg/h) based on the flow rate of air through the chambers and difference in oxygen content at inlet and output ports. The activity monitors have 15 infrared light beams spaced one inch apart on each axis, ambulatory activity is recorded when two consecutive beams are broken and the results are recorded as counts.

Resting oxygen consumption, during pre—and post-dosing, is calculated by averaging the 10-min $O_2$ consumption values, excluding periods of high ambulatory activity (ambulatory activity count >100) and excluding the first 5 values of the pre-dose period and the first value from the post-dose period. Change in oxygen consumption is reported as percent and is calculated by dividing the post-dosing resting oxygen consumption by the pre-dose oxygen consumption*100. Experiments will typically be done with n=4–6 rats and results reported are mean +/–SEM. Interpretation:

An increase in oxygen consumption of >10% is considered a positive result. Historically, vehicle-treated rats have no change in oxygen consumption from pre-dose basal.

What is claimed is:
1. A compound of Formula (I) or (II)

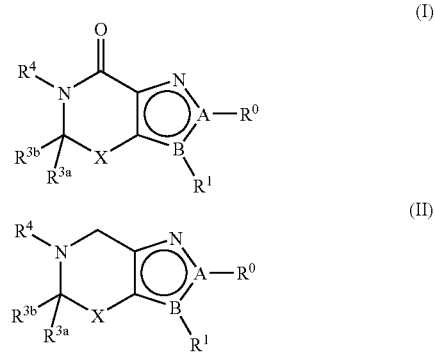

wherein
A is nitrogen and B is carbon;
$R^0$ is 2-chlorophenyl, 2-fluorophenyl, 2,4-dichlorophenyl, 2-fluoro-4-chlorophenol, 2-chloro-4-fluorophenyl, or 2,4-difluorophenyl;
$R^1$ is 4-chlorophenyl, 4-cyanophenyl, or 4-fluorophenyl;
X is —$C(R^{2a})(R^{2b})$, where $R^{2a}$ and $R^{2b}$ are each independently hydrogen, $(C_1–C_4)$alkyl, or halo-substituted $(C_1–C_4)$alkyl;
$R^{3a}$ and $R^{3b}$ are each independently hydrogen, $(C_1–C_4)$ alkyl, or halo-substituted $(C_1–C_4)$alkyl; and
$R^4$ is a chemical moiety selected from the group consisting of $(C_1–C_8)$alkyl, aryl, heteroaryl, aryl$(C_1–C_4)$alkyl, a 3- to 8-membered partially or fully saturated carbocyclic ring(s), heteroaryl$(C_1–C_3)$alkyl, 5–6 membered lactone, 5- to 6-membered lactam, and a 3- to 8-membered partially or fully saturated heterocycle, where said chemical moiety is optionally substituted with one or more substituents;
a pharmaceutically acceptable salt thereof, a prodrug of said compound or said salt, or a solvate or hydrate of said compound, said salt or said prodrug.
2. The compound of claim 1 wherein $R^4$ is a chemical moiety selected from the group consisting of $(C_1–C_8)$alkyl, aryl$(C_1–C_4)$alkyl, 3- to 6-membered partially or fully saturated carbocyclic ring(s), and 3- to 8-membered partially or fully saturated heterocycle, where said chemical moiety is optionally substituted with one or more substituents;
a pharmaceutically acceptable salt thereof, or a solvate or hydrate of said compound or said salt.
3. The compound of claim 2 wherein $R^4$ is $(C_1–C_8)$alkyl, halo-substituted $(C_1–C_8)$alkyl, cyclopentyl, cyclohexyl, piperidin-1-yl, pyrrolidin-1-yl, or morpholin-1-yl;
a pharmaceutically acceptable salt thereof, or a solvate or hydrate of said compound or said salt.

4. The compound of claim 1, 2 or 3 wherein said compound is a compound of Formula (I);
   a pharmaceutically acceptable salt thereof, or a solvate or hydrate of said compound or said salt.

5. The compound of claim 4 wherein $R^{2a}$ and $R^{2b}$ are hydrogen;
   a pharmaceutically acceptable salt thereof, or a solvate or hydrate of said compound or said salt.

6. The compound of claim 1 selected from the group consisting of
   3-(4-chloro-phenyl)-2-(2-chloro-phenyl)-6-isopropyl-2,4,5,6-tetrahydro-pyrazolo[3,4-c]pyridin-7-one;
   3-(4-chloro-phenyl)-2-(2-chloro-phenyl)-6-(2,2,2-trifluoro-ethyl)-2,4,5,6-tetrahydro-pyrazolo[3,4-c]pyridin-7-one;
   3-(4-chloro-phenyl)-2-(2-chloro-phenyl)-6-(2,2-difluoro-ethyl)-2,4,5,6-tetrahydro-pyrazolo[3,4-c]pyridin-7-one; and
   3-(4-chloro-phenyl)-2-(2-chloro-phenyl )-6-(2-fluoro-ethyl )-2,4,5,6-tetrahydro-pyrazolo[3,4-c]pyrid in-7-one;
   or a solvate or hydrate of said compound.

7. The compound of claim 1, 2 or 3 wherein said compound is a compound of Formula (II);
   a pharmaceutically acceptable salt thereof, or a solvate or hydrate of said compound or said salt.

8. A compound of Formula (III) or (IV)

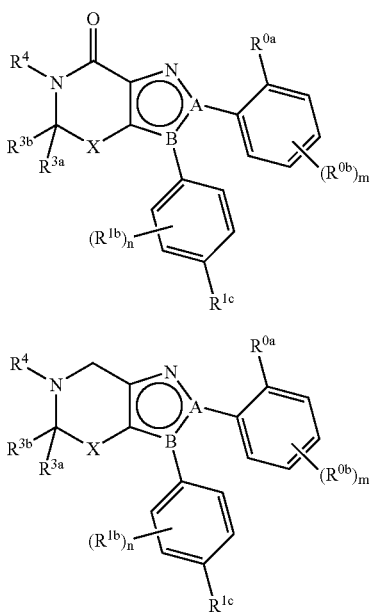

wherein
   A is nitrogen and B is carbon; $R^{0a}$, $R^{0b}$, $R^{1c}$ and $R^{1b}$ are each independently halo, $(C_1-C_4)$alkoxy, $(C_1-C_4)$alkyl, halo-substituted $(C_1-C_4)$alkyl, or cyano;
   n and m are each independently 0, 1 or 2;
   X is $-C(R^{2a})(R^{2b})$, where $R^{2a}$ and $R^{2b}$ are each independently hydrogen, $(C_1-C_4)$alkyl, or halo-substituted $(C_1-C_4)$alkyl;
   $R^{3a}$ and $R^{3b}$ are each independently hydrogen, $(C_1-C_4)$alkyl, or halo-substituted $(C_1-C_4)$alkyl; and
   $R^4$ is a chemical moiety selected from the group consisting of $(C_1-C_8)$alkyl, aryl, heteroaryl, aryl$(C_1-C_4)$alkyl, a 3- to 8-membered partially or fully saturated carbocyclic ring(s), heteroaryl$(C_1-C_3)$alkyl, 5–6 membered lactone, 5- to 6-membered lactam, and a 3- to 8-membered partially or fully saturated heterocycle, where said chemical moiety is optionally substituted with one or more substituents,
   a pharmaceutically acceptable salt thereof, a solvate or hydrate of said compound or said salt.

9. The compound of claim 8 wherein $R^4$ is a chemical moiety selected from the group consisting of $(C_1-C_8)$alkyl, aryl$(C_1-C_4)$alkyl, 3- to 8-membered partially or fully saturated carbocyclic ring(s), and 3- to 8-membered partially or fully saturated heterocycle, where said chemical moiety is optionally substituted with one or more substituents;
   a pharmaceutically acceptable salt thereof, or a solvate or hydrate of said compound or said salt.

10. The compound of claim 9 wherein $R^4$ is $(C_1-C_8)$alkyl, halo-substituted $(C_1-C_8)$alkyl, cyclopentyl, cyclohexyl, piperidin-1-yl, pyrrolidin-1-yl, or morpholin-1-yl;
    a pharmaceutically acceptable salt thereof, or a solvate or hydrate of said compound or said salt.

11. The compound of claim 10 wherein $R^4$ is halo-substituted $(C_1-C_8)$alkyl;
    a pharmaceutically acceptable salt thereof, or a solvate or hydrate of said compound or said salt.

12. The compound of claim 8, 9, 10 or 11 wherein said compound is a compound of Formula (III);
    a pharmaceutically acceptable salt thereof, a solvate or hydrate of said compound or said salt.

13. The compound of claim 12 wherein $R^{2a}$ and $R^{2b}$ are hydrogen;
    a pharmaceutically acceptable salt thereof, or a solvate or hydrate of said compound or said salt.

14. The compound of claim 8, 9, 10 or 11 wherein said compound is a compound of Formula (IV);
    a pharmaceutically acceptable salt thereof, or a solvate or hydrate of said compound or said salt.

15. The compound of claim 14 wherein $R^{2a}$ and $R^{2b}$ are hydrogen;
    a pharmaceutically acceptable salt thereof, or a solvate or hydrate of said compound or said salt.

16. A pharmaceutical composition comprising (1) a compound of claim 1, or a solvate or hydrate of said compound or said salt; and (2) a pharmaceutically acceptable excipient, diluent, or carrier.

17. A compound having the following structure

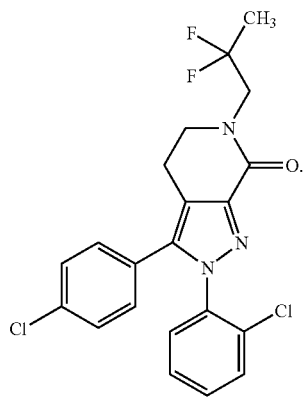

* * * * *